(12) United States Patent
Weller et al.

(10) Patent No.: US 8,007,505 B2
(45) Date of Patent: *Aug. 30, 2011

(54) SYSTEM FOR TISSUE APPROXIMATION AND FIXATION

(75) Inventors: Gary Weller, Los Gatos, CA (US); Jamy Gannoe, Redwood City, CA (US); Craig Gerbi, Mountain View, CA (US); Douglas S. Sutton, Pacifica, CA (US); Andrew H. Hancock, Fremont, CA (US); Gilbert Mata, Jr., Tracy, CA (US)

(73) Assignee: Ethicon Eado-Surgery, Inc., Cincinnati, OH (US)

( * ) Notice: Subject to any disclaimer, the term of this patent is extended or adjusted under 35 U.S.C. 154(b) by 1151 days.

This patent is subject to a terminal disclaimer.

(21) Appl. No.: 11/499,349

(22) Filed: Aug. 3, 2006

(65) Prior Publication Data
US 2006/0271076 A1 Nov. 30, 2006

Related U.S. Application Data

(63) Continuation of application No. 10/686,326, filed on Oct. 14, 2003, now Pat. No. 7,097,650.

(51) Int. Cl.
*A61B 17/08* (2006.01)
*A61B 17/10* (2006.01)
*A61B 17/04* (2006.01)
(52) U.S. Cl. .............. 606/153; 606/142; 227/175.1
(58) Field of Classification Search .......... 606/153, 606/219, 142; 227/175.1, 176.1, 179.1
See application file for complete search history.

(56) References Cited

U.S. PATENT DOCUMENTS 2,108,206 A 2/1938 Meeker
2,508,690 A 7/1948 Schmerl
(Continued)

FOREIGN PATENT DOCUMENTS

EP 0 137 878 A1 4/1985
(Continued)

OTHER PUBLICATIONS

Benjamin, S.B., et al., *A Double-Blind Cross Over Study of the Garren-Edwards anti-Obesity Bubble* Abstract Submitted to A/S/ G/E/ 1987, Georgetown University Hospital and Fairfax Hospital, Washington, D.C. and Fairfax, VA.

(Continued)

*Primary Examiner* — Julian W Woo
(74) *Attorney, Agent, or Firm* — Nutter McClennen & Fish LLP

(57) ABSTRACT

A system for tissue approximation and fixation is described herein. The devices are advanced in a minimally invasive manner within a patient's body to create one or several divisions or plications within a hollow body organ. The system comprises a tissue acquisition and folding device and a tissue stapling or fixation device, each of which is used together as a system. The acquisition device is used to approximate tissue regions from within the hollow body organ and the stapling device is advanced through a main lumen defined through the acquisition device and is used to affix the approximated tissue. The stapling device is keyed to maintain its rotational orientation relative to the acquisition device as well as to provide the user positional information of the stapling device. The acquisition device is also configured to provide lateral stability to the stapling device prior to the stapling device being clamped onto tissue.

7 Claims, 40 Drawing Sheets

U.S. PATENT DOCUMENTS

| | | |
|---|---|---|
| 3,372,443 A | 3/1968 | Daddona, Jr. |
| 3,395,710 A | 8/1968 | Stratton et al. |
| 3,844,289 A | 10/1974 | Noiles |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,131,379 A | 7/1992 | Sewell, Jr. |
| 5,156,609 A | 10/1992 | Nakao et al. |
| 5,160,343 A | 11/1992 | Brancel et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |

| | | | | | | |
|---|---|---|---|---|---|---|
| 5,887,594 | A | 3/1999 | LoCicero, III | 6,579,301 B1 | 6/2003 | Bales et al. |
| 5,888,196 | A | 3/1999 | Bonutti | 6,592,596 B1 | 7/2003 | Geitz |
| 5,897,534 | A | 4/1999 | Heim et al. | 6,605,037 B1 | 8/2003 | Moll et al. |
| 5,897,562 | A | 4/1999 | Bolanos et al. | 6,626,899 B2 | 9/2003 | Houser et al. |
| 5,904,147 | A | 5/1999 | Conlan et al. | 6,632,227 B2 | 10/2003 | Adams |
| 5,906,625 | A | 5/1999 | Bito et al. | 6,641,593 B1 | 11/2003 | Schaller et al. |
| 5,910,105 | A | 6/1999 | Swain et al. | 6,656,194 B1 | 12/2003 | Gannoe et al. |
| 5,910,149 | A | 6/1999 | Kuzmak | 6,663,598 B1 | 12/2003 | Carrillo, Jr. et al. |
| 5,921,993 | A | 7/1999 | Yoon | 6,663,639 B1 | 12/2003 | Laufer et al. |
| 5,927,284 | A | 7/1999 | Borst et al. | 6,663,640 B2 | 12/2003 | Kortenbach |
| 5,928,264 | A | 7/1999 | Sugarbaker et al. | 6,675,809 B2 | 1/2004 | Stack et al. |
| 5,935,107 | A | 8/1999 | Taylor et al. | 6,682,520 B2 | 1/2004 | Ingenito |
| 5,938,669 | A | 8/1999 | Klaiber et al. | 6,689,062 B1 | 2/2004 | Mesallum |
| 5,947,983 | A | 9/1999 | Solar et al. | 6,692,485 B1 | 2/2004 | Brock et al. |
| 5,964,772 | A | 10/1999 | Bolduc et al. | 6,716,222 B2 | 4/2004 | McAlister et al. |
| 5,964,782 | A | 10/1999 | Lafontaine et al. | 6,733,512 B2 | 5/2004 | McGhan |
| 5,972,001 | A | 10/1999 | Yoon | 6,736,822 B2 | 5/2004 | McClellan et al. |
| 5,972,002 | A | 10/1999 | Bark et al. | 6,740,098 B2 | 5/2004 | Abrams et al. |
| 5,976,161 | A | 11/1999 | Kirsch et al. | 6,740,121 B2 | 5/2004 | Geitz |
| 5,980,537 | A | 11/1999 | Ouchi | 6,746,460 B2 | 6/2004 | Gannoe et al. |
| 5,993,464 | A | 11/1999 | Knodel | 6,746,489 B2 | 6/2004 | Dua et al. |
| 5,993,473 | A | 11/1999 | Chan et al. | 6,754,536 B2 | 6/2004 | Swoyer et al. |
| 6,015,378 | A | 1/2000 | Borst et al. | 6,755,849 B1 | 6/2004 | Gowda et al. |
| 6,030,364 | A | 2/2000 | Durgin et al. | 6,755,869 B2 | 6/2004 | Geitz |
| 6,030,392 | A | 2/2000 | Dakov | 6,756,364 B2 | 6/2004 | Barbier et al. |
| 6,042,538 | A | 3/2000 | Puskas | 6,764,518 B2 | 7/2004 | Godin |
| 6,044,847 | A | 4/2000 | Carter et al. | 6,773,440 B2 | 8/2004 | Gannoe et al. |
| 6,067,991 | A | 5/2000 | Forsell | 6,773,441 B1 | 8/2004 | Laufer et al. |
| 6,074,343 | A | 6/2000 | Nathanson et al. | 6,786,898 B2 | 9/2004 | Guenst |
| 6,083,241 | A | 7/2000 | Longo et al. | 6,790,214 B2 | 9/2004 | Kraemer et al. |
| 6,086,600 | A | 7/2000 | Kortenbach | 6,802,868 B2 | 10/2004 | Silverman et al. |
| 6,113,609 | A | 9/2000 | Adams | 6,821,285 B2 | 11/2004 | Laufer et al. |
| 6,119,913 | A | 9/2000 | Adams et al. | 6,835,199 B2 | 12/2004 | McGuckin, Jr. et al. |
| 6,120,513 | A | 9/2000 | Bailey et al. | 6,835,200 B2 | 12/2004 | Laufer et al. |
| 6,136,006 | A | 10/2000 | Johnson et al. | 6,837,848 B2 | 1/2005 | Bonner et al. |
| 6,149,660 | A | 11/2000 | Laufer et al. | 6,840,423 B2 | 1/2005 | Adams et al. |
| 6,159,146 | A | 12/2000 | El Gazayerli | 6,845,776 B2 | 1/2005 | Stack et al. |
| 6,159,195 | A | 12/2000 | Ha et al. | 6,866,663 B2 | 3/2005 | Edwards et al. |
| 6,165,183 | A | 12/2000 | Kuehn et al. | 6,896,682 B1 | 5/2005 | McClellan et al. |
| 6,179,195 | B1 | 1/2001 | Adams et al. | 6,926,722 B2 | 8/2005 | Geitz |
| 6,186,942 | B1 | 2/2001 | Sullivan et al. | 6,966,919 B2 | 11/2005 | Sixto, Jr. et al. |
| 6,186,985 | B1 | 2/2001 | Snow | 6,981,978 B2 | 1/2006 | Gannoe |
| 6,197,022 | B1 | 3/2001 | Baker | 6,991,643 B2 | 1/2006 | Saadat |
| 6,200,318 | B1 | 3/2001 | Har-Shai et al. | 6,994,715 B2 | 2/2006 | Gannoe et al. |
| 6,206,822 | B1 | 3/2001 | Foley et al. | 7,020,531 B1 | 3/2006 | Colliou et al. |
| 6,206,893 | B1 | 3/2001 | Klein et al. | 7,025,791 B2 | 4/2006 | Levine et al. |
| 6,224,614 | B1 | 5/2001 | Yoon | 7,033,373 B2 | 4/2006 | de al Torre et al. |
| 6,231,561 | B1 | 5/2001 | Frazier et al. | 7,033,378 B2 | 4/2006 | Smith et al. |
| 6,248,058 | B1 | 6/2001 | Silverman et al. | 7,033,384 B2 | 4/2006 | Gannoe et al. |
| 6,254,642 | B1 | 7/2001 | Taylor | 7,037,343 B2 | 5/2006 | Imran |
| 6,273,897 | B1 | 8/2001 | Dalessandro et al. | 7,037,344 B2 | 5/2006 | Kagan et al. |
| 6,279,809 | B1 | 8/2001 | Nicolo | 7,063,715 B2 | 6/2006 | Onuki et al. |
| 6,290,674 | B1 | 9/2001 | Roue et al. | 7,083,629 B2 | 8/2006 | Weller et al. |
| 6,293,923 | B1 | 9/2001 | Yachia et al. | 7,083,630 B2 | 8/2006 | DeVries et al. |
| 6,302,917 | B1 | 10/2001 | Dua et al. | 7,087,011 B2 | 8/2006 | Cabiri et al. |
| 6,312,437 | B1 | 11/2001 | Kortenbach | 7,097,650 B2 * | 8/2006 | Weller et al. .................. 606/153 |
| 6,328,689 | B1 | 12/2001 | Gonzalez et al. | 7,125,403 B2 | 10/2006 | Julian et al. |
| 6,338,345 | B1 | 1/2002 | Johnson et al. | 7,220,237 B2 | 5/2007 | Gannoe et al. |
| 6,352,543 | B1 | 3/2002 | Cole | 2001/0014800 A1 | 8/2001 | Frazier et al. |
| 6,358,197 | B1 | 3/2002 | Silverman et al. | 2001/0020190 A1 | 9/2001 | Taylor |
| 6,379,366 | B1 | 4/2002 | Fleischman et al. | 2001/0037127 A1 | 11/2001 | De Hoyos Garza |
| 6,387,104 | B1 | 5/2002 | Pugsley, Jr. et al. | 2002/0022851 A1 | 2/2002 | Kalloo et al. |
| 6,398,795 | B1 | 6/2002 | McAlister et al. | 2002/0035361 A1 | 3/2002 | Houser et al. |
| 6,416,535 | B1 | 7/2002 | Lazarus | 2002/0040226 A1 | 4/2002 | Laufer et al. |
| 6,423,087 | B1 | 7/2002 | Sawada | 2002/0047036 A1 | 4/2002 | Sullivan et al. |
| 6,432,040 | B1 | 8/2002 | Meah | 2002/0058967 A1 | 5/2002 | Jervis |
| 6,447,533 | B1 | 9/2002 | Adams | 2002/0072761 A1 | 6/2002 | Abrams et al. |
| 6,460,543 | B1 | 10/2002 | Forsell | 2002/0077661 A1 | 6/2002 | Saadat |
| 6,475,136 | B1 | 11/2002 | Forsell | 2002/0078967 A1 | 6/2002 | Sixto, Jr. et al. |
| 6,491,707 | B2 | 12/2002 | Makower et al. | 2002/0082621 A1 | 6/2002 | Schurr et al. |
| 6,494,888 | B1 | 12/2002 | Laufer et al. | 2002/0143346 A1 | 10/2002 | McGuckin, Jr. et al. |
| 6,506,196 | B1 | 1/2003 | Laufer | 2002/0165589 A1 | 11/2002 | Imran et al. |
| 6,535,764 | B2 | 3/2003 | Imran et al. | 2002/0183768 A1 | 12/2002 | Deem et al. |
| 6,540,789 | B1 | 4/2003 | Silverman et al. | 2002/0193816 A1 | 12/2002 | Laufer et al. |
| 6,551,310 | B1 | 4/2003 | Ganz et al. | 2003/0040804 A1 | 2/2003 | Stack et al. |
| 6,554,844 | B2 | 4/2003 | Lee et al. | 2003/0040808 A1 | 2/2003 | Stack et al. |
| 6,558,400 | B2 | 5/2003 | Deem et al. | 2003/0065340 A1 | 4/2003 | Geitz |
| 6,561,969 | B2 | 5/2003 | Frazier et al. | 2003/0065359 A1 | 4/2003 | Weller et al. |
| 6,572,629 | B2 | 6/2003 | Kalloo et al. | 2003/0093117 A1 | 5/2003 | Saadat |

| | | |
|---|---|---|
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0127491 A1 | 7/2003 | Adams et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0194157 A1 | 9/2004 | Meguid |
| 2004/0194790 A1 | 10/2004 | Laufer et al. |
| 2004/0210243 A1 | 10/2004 | Gannoe et al. |
| 2004/0215180 A1 | 10/2004 | Starkebaum et al. |
| 2004/0220682 A1 | 11/2004 | Levine et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0249362 A1 | 12/2004 | Levine et al. |
| 2005/0010162 A1 | 1/2005 | Utley et al. |
| 2005/0021681 A1 | 1/2005 | Oommen |
| 2005/0033328 A1 | 2/2005 | Laufer et al. |
| 2005/0038415 A1 | 2/2005 | Rohr et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0192599 A1 | 9/2005 | Demarais |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0228415 A1 | 10/2005 | Gertner |
| 2005/0228504 A1 | 10/2005 | Demarais |
| 2005/0256533 A1 | 11/2005 | Roth et al. |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0122462 A1 | 6/2006 | Roth et al. |
| 2006/0142787 A1 | 6/2006 | Weller et al. |
| 2006/0151568 A1 | 7/2006 | Weller et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | WO 94/18893 A1 | 9/1994 |
| WO | 9915086 A1 | 4/1999 |
| WO | WO 99/17662 A1 | 4/1999 |
| WO | 9922649 A2 | 5/1999 |
| WO | WO 99/53827 A1 | 10/1999 |
| WO | WO 00/32137 A1 | 6/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO-02/24080 A2 | 3/2002 |
| WO | WO 02/24080 A2 | 3/2002 |
| WO | WO 02/35980 A2 | 5/2002 |
| WO | WO 02/39880 A2 | 5/2002 |
| WO | WO-02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | 2004004542 A2 | 1/2004 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO-2004/019788 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |

| | | |
|---|---|---|
| WO | WO 2005/023118 A1 | 3/2005 |
| WO | WO 2005/037152 A1 | 4/2005 |
| WO | WO-2005/040010 A2 | 5/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., Small Intestinal Obturation Secondary to Obturation by a Garren Gastric Bubble, *The American Journal of Gastroenterology*, vol. 82, No. 1, pp. 51-53, 1987.

Büchler, M.W., M.D. et al., A Technique for Gastroplasty As A Substitute For The Esophagus: Fundus Rotation Gastroplasty, *Journal of the American College of Surgeons*, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D.[1], et al., Gastro-Clip® Gastroplasty: A Very Long-Term Complication, *Obesity Surgery*, 14, © FD-Communications Inc., 2004.

Clark, Charlene, R.N., The Gastric Bubble: Medicine, Magic or Mania? *SGA Journal*, vol. 9, No. 2, pp. 45-47, Fall 1986.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

DeMeester, Tom T., M.D., Evolving Concepts of Reflux: The Ups and Downs of the LES, *Canadian Journal of Gastroenterology*, vol. 16, No. 5, pp. 327-331, 2002.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Filipi, Charles J. M.D., et al., Transoral, Flexible Endoscopic Suturing for Treatment Of GERD: A Multicenter Trial, *Gastrointestinal Endoscopy*, vol. 53, No. 4, pp. 416-422, 2001.

Gray, Henry, R.R.S., *Anatomy of the Human Body*, The Digestive System, Thirtieth American Edition, pp. 1466-1467 (Undated).

Guidant, Internet, AXIUS™ Vacuum 2 Stabilizer Systems, Internet Website—www.guidant.com/products/axius_vacuum.shtml, 8 pages, visited May 27, 2003.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.com/viewarticle/423508_print_pp. 1-20, Medscape General Medicine 4(1), 2003 © 2002 Medscape, downloaded Oct. 9, 2006.

Hepworth, Clive C. FRCS et al., Mechanical Endoscopic Methods of Haemostasis for Bleeding Peptic Ulcers: A Review, *Bailliere's Clinical Gastroenterology*, vol. 14, No. 3 pp. 467-476, 2000.

Ikeda, Y. et al., New Suturing Device For Transanal Endoscopic Microsurgery, *Blackwell Science Ltd*. p. 1290, 1997.

Johnson & Johnson Gateways^SM Endopath 3mm, 5mm and 10 mm Diameter Endoscopic Instruments, Internet Website—www.inigateway.com/home.ihtml?loc=USENG&page=viewContent&parentId-0900..., 3 pages, visited May 29, 2003.

Kirby, Donald F., Incomplete Small Bowel Obstruction by the Garren-Edwards Gastric Bubble Necessitating Surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Power Medical Interventions Digital and Wireless Medical Technology, Product Innovation: SurgASSIST™, Internet Website—www/pmi2.com/access_flexibility.asp, 6 pages, visited May 29, 2003.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., An Endoscopic Sewing Machine, *Gastrointestinal Endoscopy*, vol. 32, No. 1 pp. 36-38 1986.

Swain, C. Paul, M.D., Endoscopic Sewing And Stapling Machines, *Endoscopy* pp. 205-210, © Georg Thieme Verlag Stuttgart, New York, 1997.

Swain, C. Paul, M.D. et al., An Endoscopic Stapling Device: The Development Of A New Flexible Endoscopically Controlled Device For Placing Multiple Transmural Staples In Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall,, vol. 13 No. 1, pp. 97-108, 1999.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

Supplementary European Search Report dated May 19, 2010.

Davenport, H.W. (1971). Physiology of the Digestive Tract, Third Edition, Year Book Medical Publishers, Inc.: Chicago, IL, pp. 9-10 (Table of Contents Only).

Endo Gia* Universal, Single UseStapler and Endo GIA Roticulator*, (2000). Brochure, 8 pages.

Snowden Pencer, Diamon-Flex Angled Snake Retractor (class 1, 878.4800), Appendix F.f. No later than Oct. 16, 2006 (submitted in U.S. Appl. No. 11/107,382).

U.S. Appl. No. 60/234,360, filed Sep. 22, 2000, Schurr. cited by other.

* cited by examiner

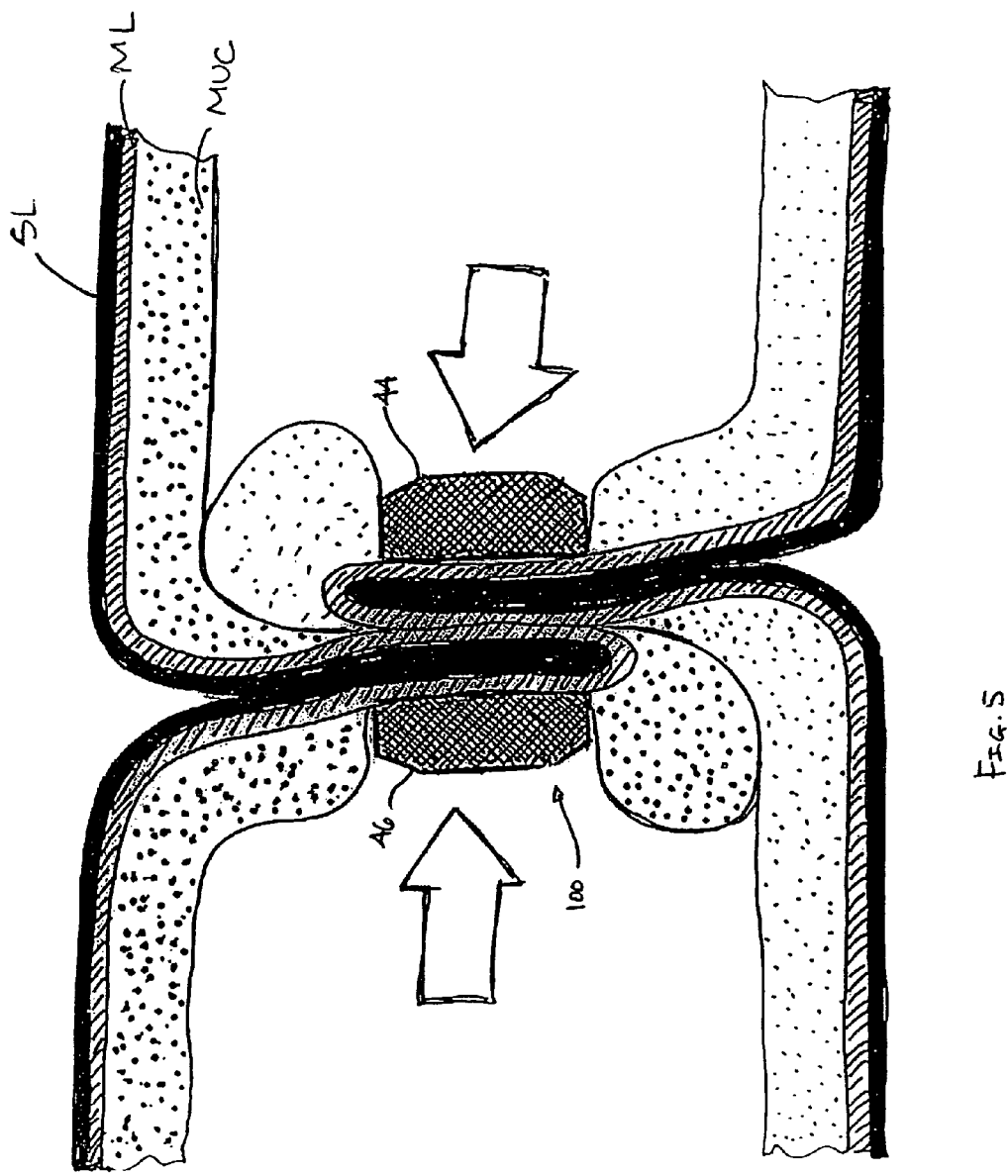

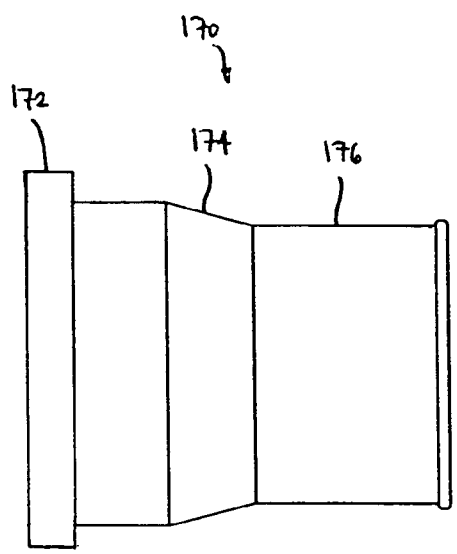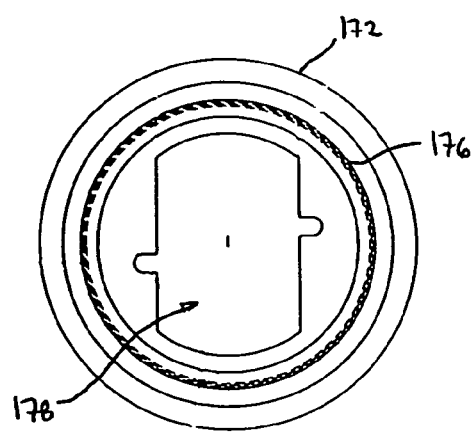
Fig. 8A                    Fig. 8B
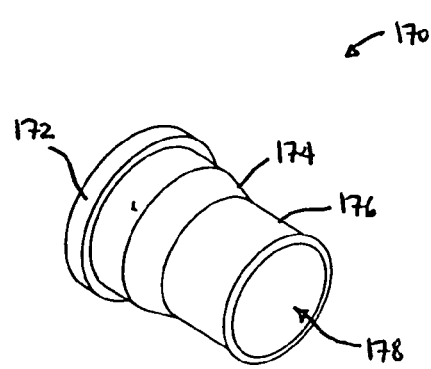
Fig. 8C

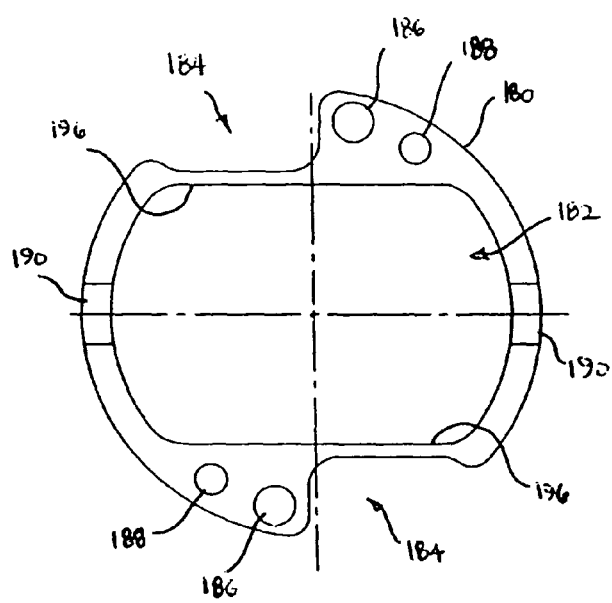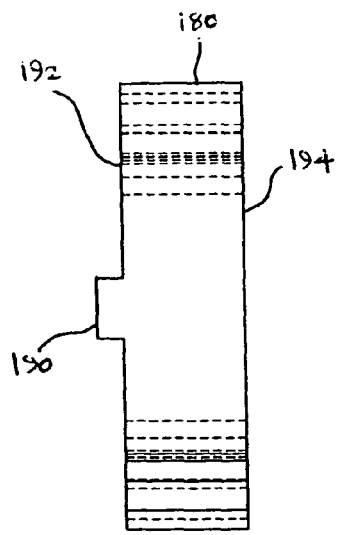
FIG. 9A      FIG. 9B
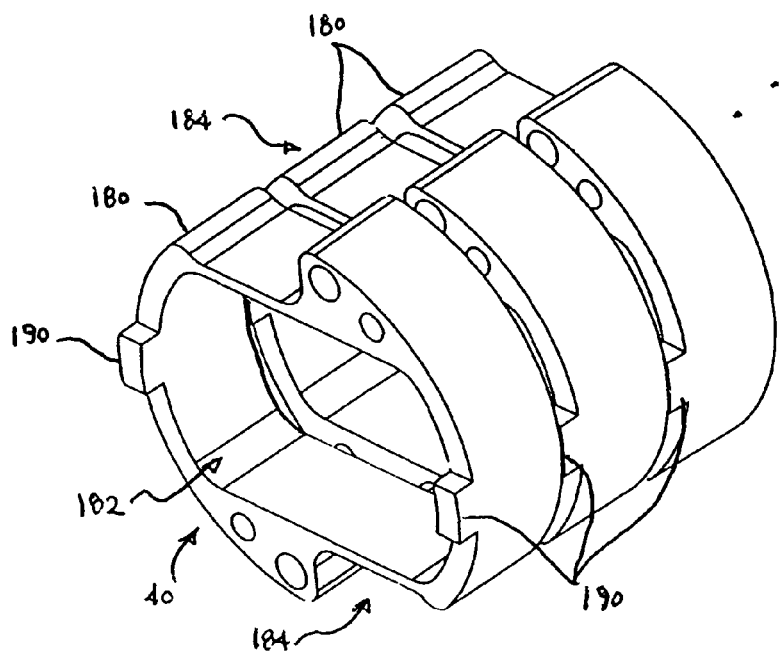
FIG. 9C

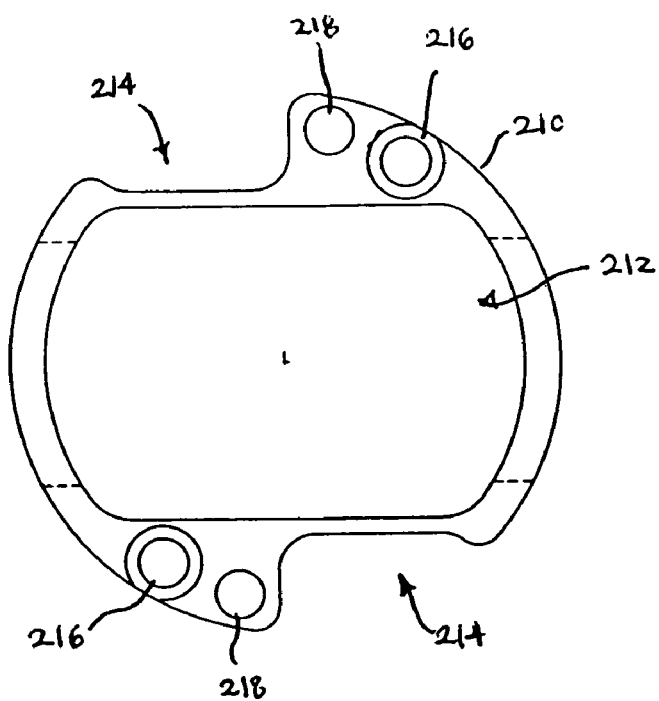
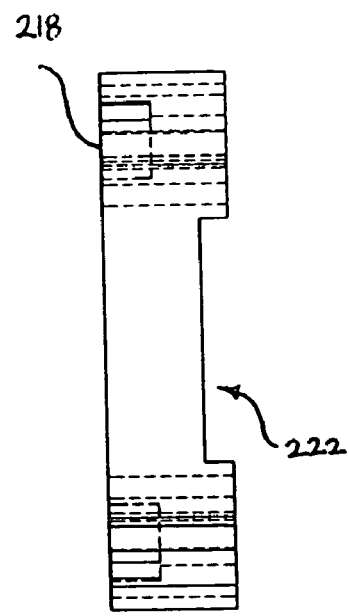
FIG. 10A        FIG. 10B
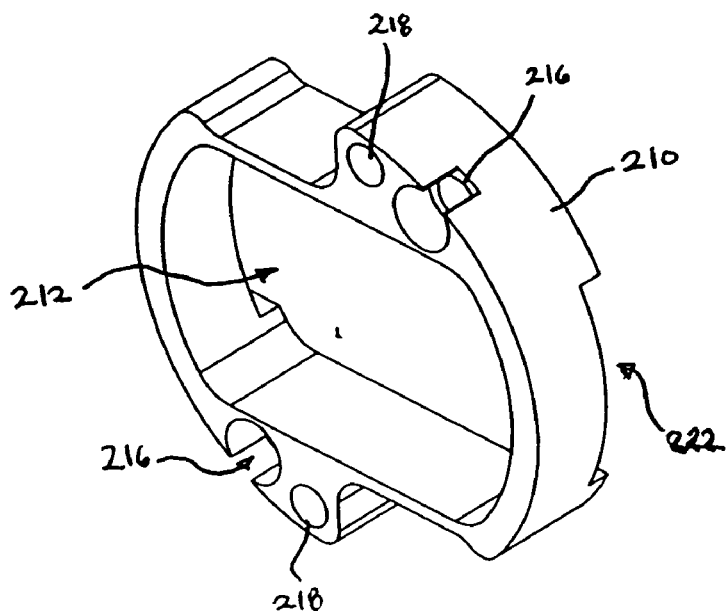
FIG. 10C

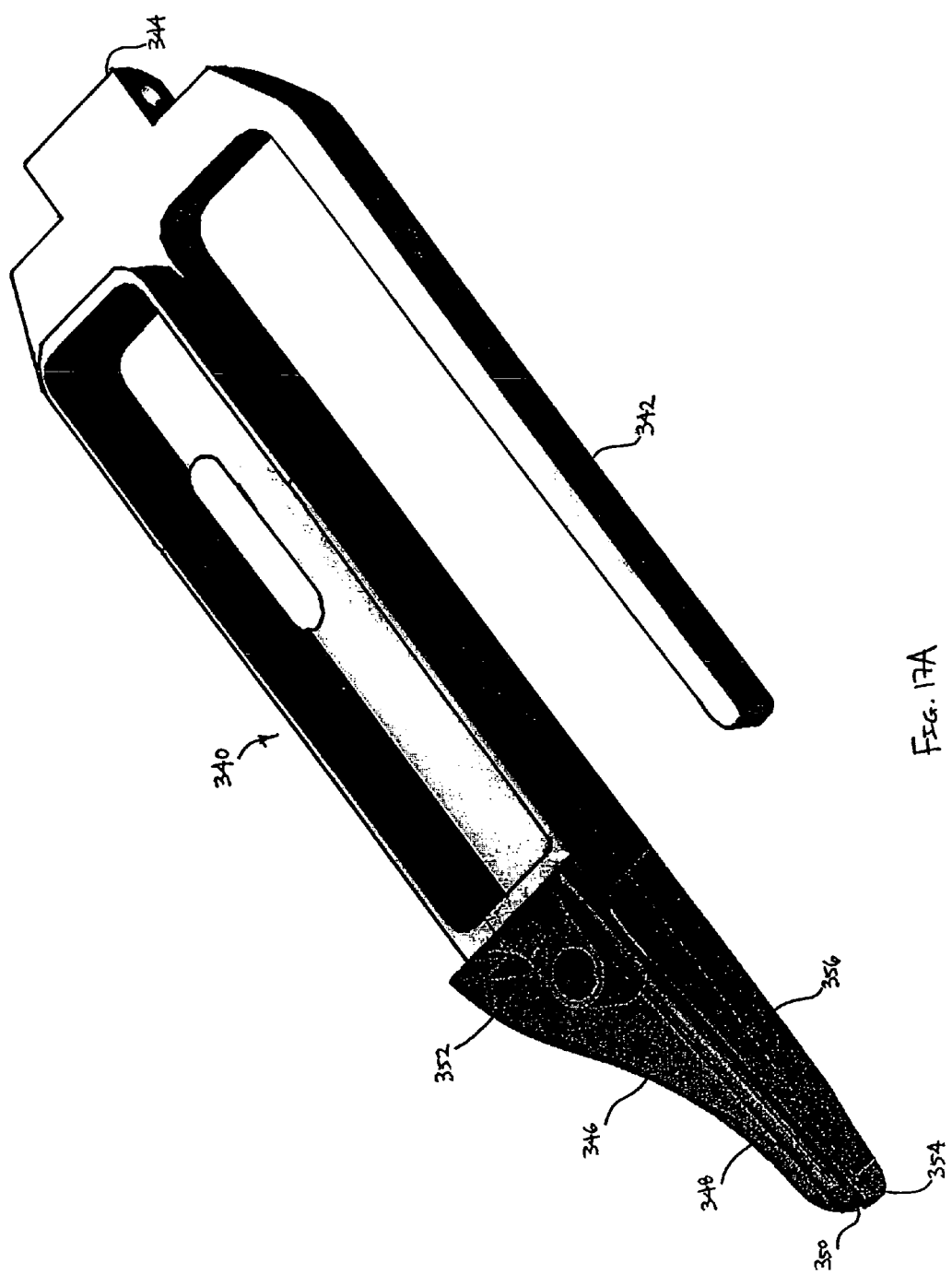

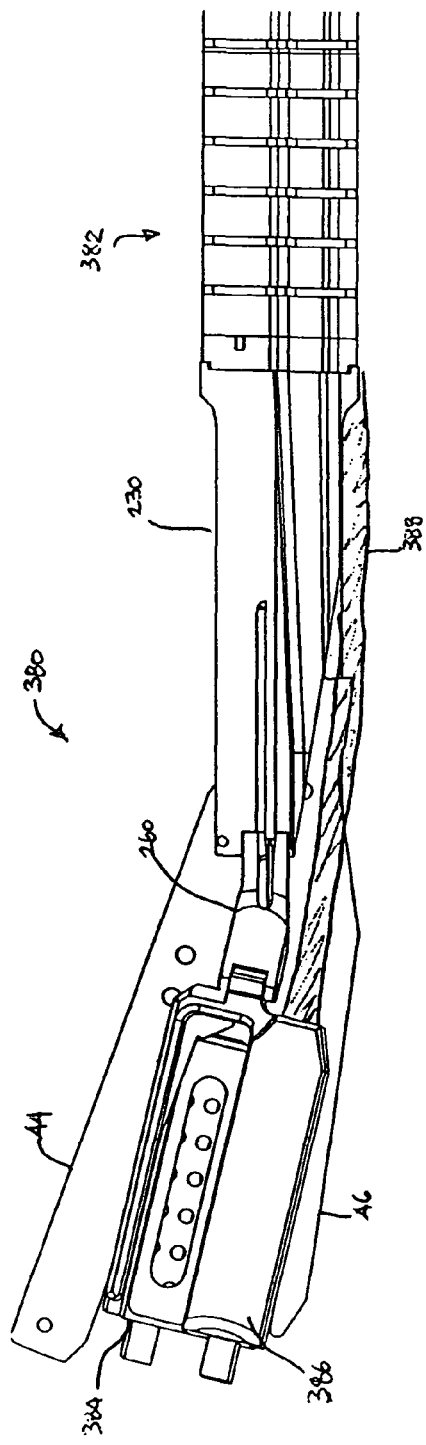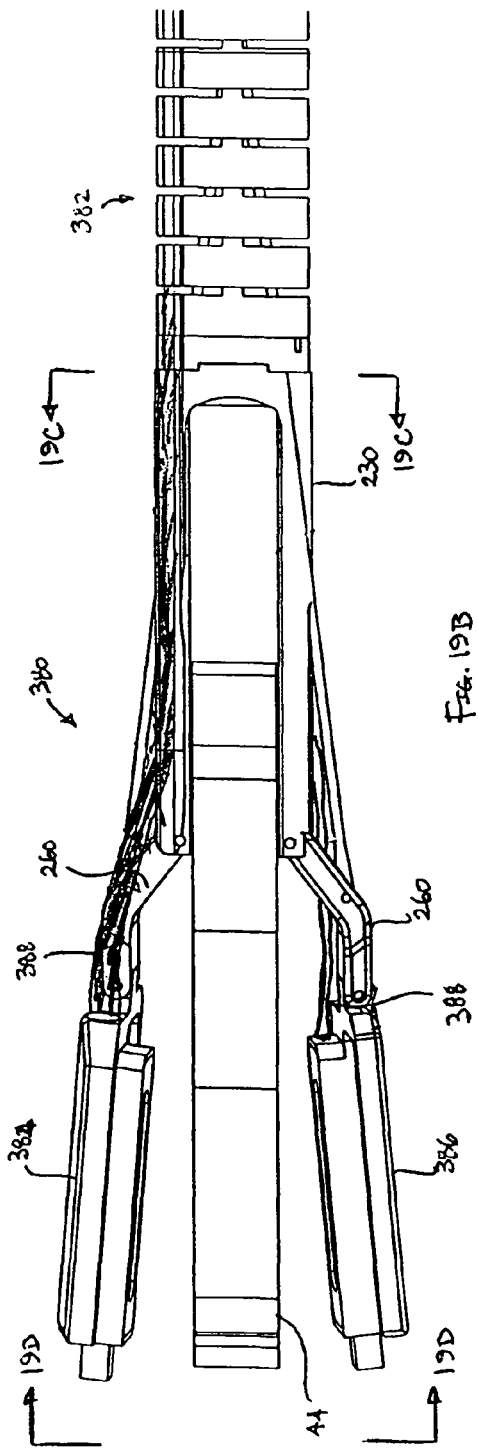
Fig. 19A
Fig. 19B

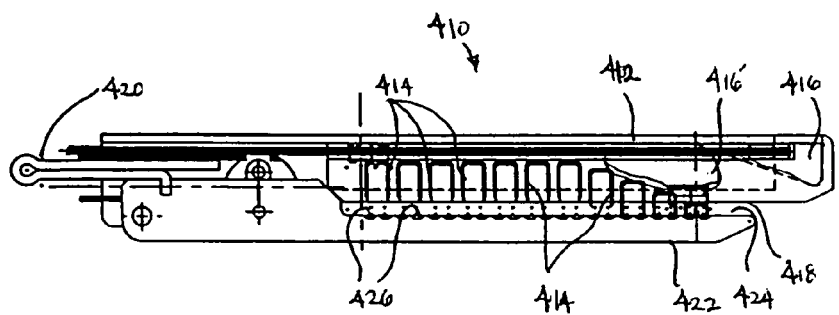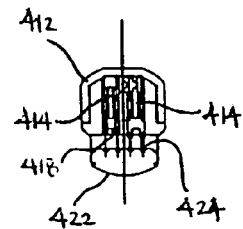
FIG. 22A  FIG. 22B
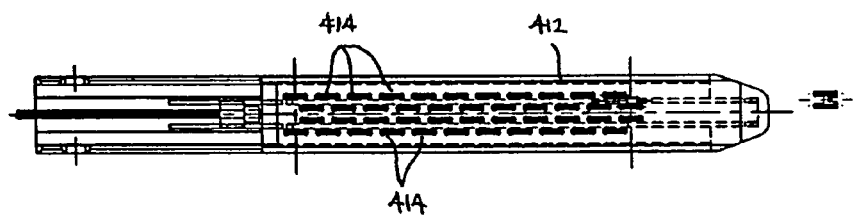
FIG. 22C
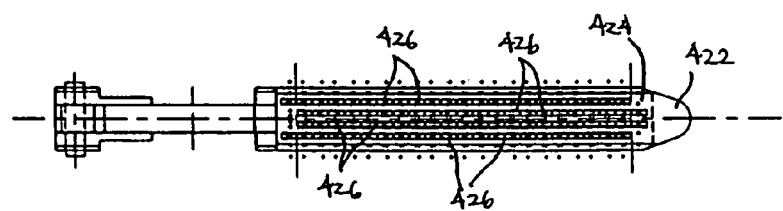
FIG. 22D

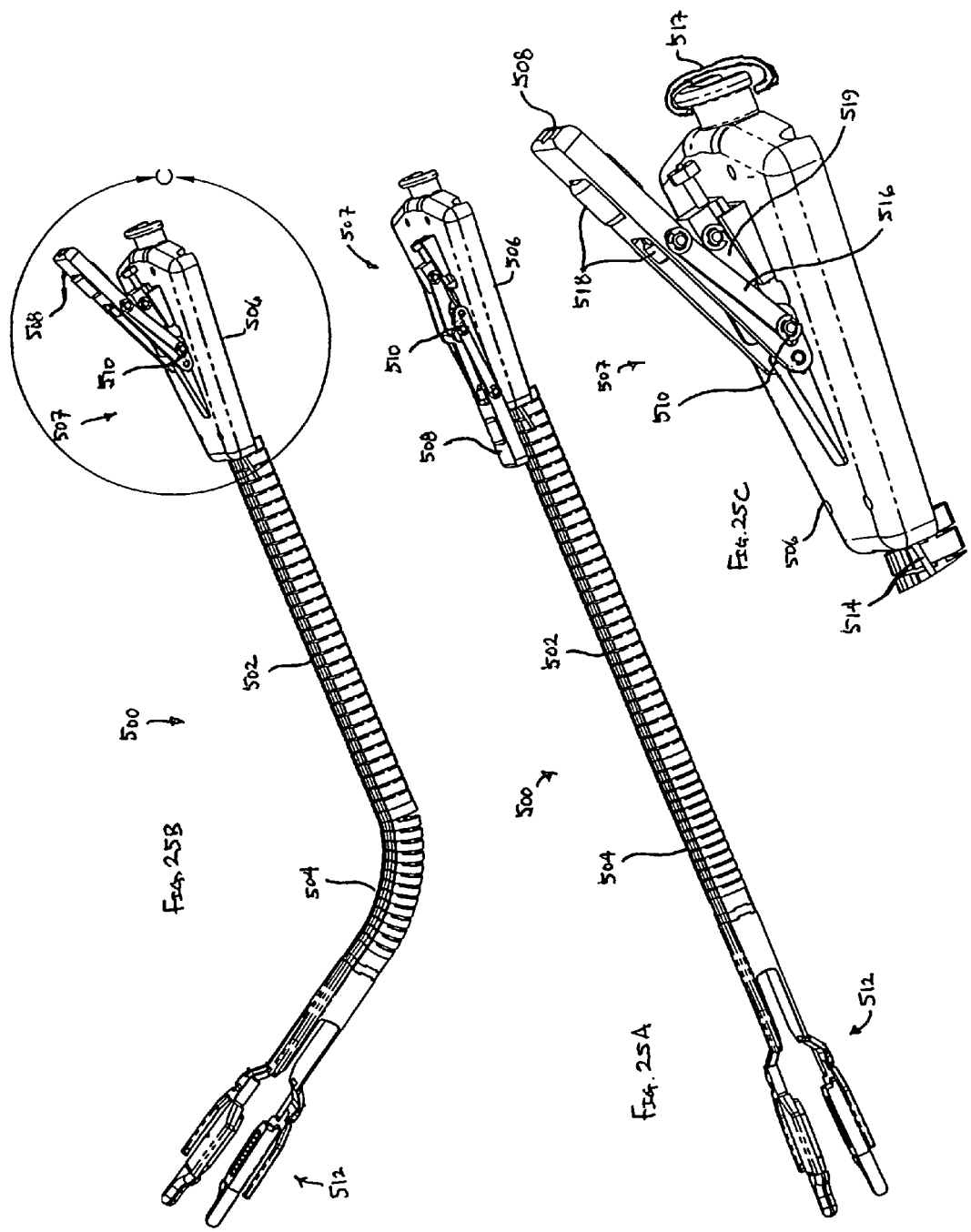

SYSTEM FOR TISSUE APPROXIMATION AND FIXATION

This application is a continuation of U.S. Ser. No. 10/686,326 filed Oct. 14, 2003 now U.S. Pat. No. 7,097,650, the contents of which are incorporated herein by reference.

FIELD OF THE INVENTION

The present invention relates generally to medical apparatus and methods. More particularly, it relates to devices and methods for approximating portions of a hollow body organ, particularly a stomach, intestine, or other region of the gastrointestinal tract, while affixing the tissue.

BACKGROUND OF THE INVENTION

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Typically, these stomach reduction procedures are performed surgically through an open incision and staples or sutures are applied externally to the stomach or hollow body organ. Such procedures can also be performed laparoscopically, through the use of smaller incisions, or ports, through trocars and other specialized devices. In the case of laparoscopic banding, an adjustable band is placed around the proximal section of the stomach reaching from the lesser curve of the stomach around to the greater curve, thereby creating a constriction or "waist" in a vertical manner between the esophagus and the pylorus. During a VBG, a small pouch (approximately 20 cc in volume) is constructed by forming a vertical partition from the gastroesophageal junction to midway down the lesser curvature of the stomach by externally applying staples, and optionally dividing or resecting a portion of the stomach, followed by creation of a stoma at the outlet of the partition to prevent dilation of the outlet channel and restrict intake. In a Roux-En-Y gastric bypass, the stomach is surgically divided into a smaller upper pouch connected to the esophageal inflow, and a lower portion, detached from the upper pouch but still connected to the intestinal tract for purposes of secreting digestive juices. A resected portion of the small intestine is then anastomosed using an end-to-side anastomosis to the upper pouch, thereby bypassing the majority of the intestine and reducing absorption of caloric intake and causing rapid "dumping" of highly caloric or "junk foods".

Although the outcome of these stomach reduction surgeries leads to patient weight loss because patients are physically forced to eat less due to the reduced size of their stomach, several limitations exist due to the invasiveness of the procedures, including time, use of general anesthesia, time and pain associated with the healing of the incisions, and other complications attendant to major surgery. In addition, these procedures are only available to a small segment of the obese population (morbid obesity, Body Mass Index≧40) due to their complications, leaving patients who are considered obese or moderately obese with few, if any, interventional options.

In addition to surgical procedures, certain tools exist for approximating or otherwise securing tissue such as the stapling devices used in the above-described surgical procedures and others such as in the treatment of gastroesophageal reflux disease (GERD). These devices include the GIA® device (Gastrointestinal Anastomosis device manufactured by Ethicon Endosurgery, Inc. and a similar product by USSC), and certain clamping and stapling devices as described in U.S. Pat. Nos. 5,403,326; 5,571,116; 5,676,674; 5,897,562; 6,494,888; and 6,506,196 for methods and devices for fundoplication of the stomach to the esophagus for the treatment of gastroesophageal reflux disease (GERD). In addition, certain tools, such as those described in U.S. Pat. Nos. 5,788,715 and 5,947,983, detail an endoscopic suturing device that is inserted through an endoscope and placed at the site where the esophagus and the stomach meet. Vacuum is then applied to acquire the adjacent tissue, and a series of stitches are placed to create a pleat in the sphincter to reduce the backflow of acid from the stomach up through the esophagus. These devices can also be used transorally for the endoscopic treatment of esophageal varices (dilated blood vessels within the wall of the esophagus).

There is a need for improved devices and procedures. In addition, because of the invasiveness of most of the surgeries used to treat obesity and other gastric disorders such as GERD, and the limited success of others, there remains a need for improved devices and methods for more effective, less invasive hollow organ restriction procedures.

BRIEF SUMMARY OF THE INVENTION

A system for tissue approximation and fixation is described which may be used to approximate tissue regions from within a hollow body organ, such as the stomach, esophageal junction, and other portions of the gastrointestinal tract. Generally, the devices of the system may be advanced in a minimally invasive manner within a patient's body, e.g., transorally, endoscopically, percutaneously, etc., to create one or several divisions or plications within the hollow body organ. Examples of placing and/or creating divisions or plications may be seen in further detail in U.S. Pat. No. 6,558,400; U.S. patent application Ser. No. 10/188,547 filed Jul. 2, 2002; and U.S. patent application Ser. No. 10/417,790 filed Apr. 16, 2003, each of which is incorporated herein by reference in its entirety. The system may comprise at least a tissue acquisition and folding device and a tissue stapling or fixation device, each of which may be used together as a single system.

The folder assembly may generally comprise, in part, a pod assembly which may be used to initially acquire and approximate the tissue to be folded. The pod assembly may comprise a first pod member and a second pod member, each of which may be independently articulatable to form a first compact configuration and a second larger, expanded configuration. Each of the pod members may be connected to respective first and second actuation rods on the distal end of a yoke member, which connects the pod members to an elongate working body or shaft. The working body itself may be comprised of a plurality of aligned link members which are adapted to provide some flexibility to the working body and which defines a main lumen throughout a length of the working body as well as through the handle connected to a proximal end of the working body. Moreover, the working body may be covered by a sheath or a covering to enhance the lubricity of the shaft as well as to maintain the interior of the working body clear from body fluids and debris and seal the shaft to allow insufflation of the target organ. Various materials may be utilized for the sheath including various plastics, elastomers, latex, polyurethane, thermoplastics, e.g., PTFE, silicone, PVC, FEP, Tecoflex®, Pebax®, etc., so long as they are preferably biocompatible.

One or both of the pod members may additionally define a vacuum chamber or opening into which the tissue may be drawn within. The opening of the vacuum chamber may be slotted along a direction parallel to a longitudinal axis of the working body; alternatively, the opening may be defined a variety of shapes, e.g., oval, elliptical, etc., and furthermore may be offset such that it is defined transverse to the longitudinal axis of the working body. Adjacent to and preferably parallel with the vacuum chamber is a tensioning arm or member, which may have a length equal to that of the vacuum chamber. Alternatively, a length of the tensioning member may be less than or greater than that of vacuum chamber. The distal end of each pod member may have a flexible and/or atraumatic tip such as a blunt, rounded, or "bullet" tip, made from any number of polymers to facilitate the guidance of the pod assembly into the hollow body organ without damaging tissue along the way.

A guidewire may optionally be used with the folder assembly during initial deployment and positioning within the hollow body organ in a manner similar to a catheter for guiding the pod assembly to a predetermined position. The use of the guidewire may assist in initial placement of the device transorally, and it can also be exchanged through a lumen in the tip of one or both of the pod tips. Both of the first and second pod members may each be adapted to pivot on respective hinge members such that in a first compact configuration, the first and second pod members are immediately adjacent to one another. When desirably positioned within the hollow body organ, a vacuum force may be applied within one or both of the pod members such that tissue begins to enter within one or both of the vacuum chambers or openings. To assist in placement of the device, various indicators may be used. For instance, one or several indicators may be located directly on the device or indicators may be utilized with the device in relation to anatomical structures or landmarks. In one example, an orientation marker may be placed at a point on the distal portion of the device that is visible endoscopically and can be adjusted relative to structures such as the "z-line" of the gastroesophageal, i.e., the place where a change in color of the tissue from whitish (esophagus) to a salmon color (stomach) occurs delineating what is referred to as the squamocolumnar junction, i.e., the point where the lining changes from esophageal (squamous) to stomach (columnar). Then, in moving to a second expanded configuration, one or both of the first pod member and/or the second pod member may be translated via actuation rods into opposing radial directions from one another such that the opposing areas of tissue are approximated to create an overlap region. Once this overlap region has been desirably created, the fixation assembly may be advanced distally through the main lumen of the folder assembly and positioned upon exiting the main lumen to become clamped directly over the overlapped tissue. It is also within the scope of this disclosure to actuate the pods simultaneously, serially or singularly where only one fold of tissue is manipulated and fastened.

Vacuum tubes may be routed through the length, or a partial length, of the working body for communication with the pod assembly. The proximal ends of the vacuum tubes may be connected to one or more vacuum pumps. Furthermore, the vacuum tubes may utilize braided materials, e.g., stainless steel or superelastic materials such as Nickel-Titanium alloy, integrated throughout to prevent kinking or pinching of the tubes.

The fixation assembly comprises, in part, a manipulatable stapler assembly connected via a flexible shaft to a stapler handle. The stapler assembly itself generally comprises a staple cartridge housing within which one or more staples are housed. A corresponding anvil is positioned in apposition to the staple cartridge housing and may be used to provide a staple closure surface when tissue to be affixed is adequately positioned between the staple cartridge housing and the anvil. With the stapler assembly connected at the distal end of a flexible shaft, a handle is connected at the proximal end of the shaft. The handle itself may allow the surgeon or user to hold and manipulate the fixation assembly while articulating the stapler assembly between an open and closed configuration. Moreover, the configuration of the handle allows the surgeon or user to actuate the stapler assembly as well as deploy the staples from the staple cartridge housing.

In use, the fixation assembly may be advanced within the folder assembly main lumen with the fixation assembly configured in a closed configuration. To maintain an orientation, i.e., rotational stability, of the fixation assembly relative to the folder assembly and the approximated tissue, the fixation assembly may be configured to have a shape which is keyed to a cross-sectional area of the folder assembly main lumen. The keyed configuration helps to ensure that as the fixation assembly is advanced through the folder assembly, that the stapler assembly is optimally positioned to be clamped over the tissue for fixation.

When the stapler assembly is advanced and has exited the main lumen of the working body, the staple cartridge housing may be actuated into an open configuration when positioned between distally extending arm members of a yoke to receive the tissue folded between the pod members. The yoke arm members are configured such that when the stapler assembly is positioned therebetween, the stapler assembly is prevented from rotating or bending out of alignment for tissue affixation, i.e., the lateral stability of the stapler assembly is maintained relative to the yoke and the tissue. The stapler assembly may then be advanced distally over the folded tissue and clamped onto the tissue for deploying the staples. To avoid damaging tissue surrounding the pod assembly, one or several insertion indicators may be defined along a portion of flexible shaft of the fixation assembly, preferably near a proximal end of the shaft, to aid the user in knowing when the stapler assembly may be safely articulated while the fixation assembly is positioned within the working body, i.e., the longitudinal stability of the stapler assembly is maintained relative to the folder assembly. The indicators may be configured to align with a proximal end of the folder handle to correspondingly indicate, e.g., a position of the fixation assembly relative to the folder assembly when the stapler assembly may be opened, and/or how far distally the fixation assembly may be advanced relative to the folder assembly to engage the folded tissue, and when the devices are in a "safe to clamp" mode (e.g., in position around the tissue). Such positional indicators may utilize mechanical features, such as a stop or detent. In addition, the stapler assembly jaws my be spring-loaded open to assist insertion.

BRIEF DESCRIPTION OF THE DRAWINGS

FIG. 5 shows an example of a cross-sectional side view of the tissue overlap where a stapler assembly has been articulated and clamped onto the tissue overlap.

FIGS. 8A to 8C show side, end, and perspective views, respectively, of a link which may serve as a transitional link between the folder handle and the working body.

FIGS. 9A to 9C show side, end, and perspective views, respectively, of one variation of links which may be used to form at least part of the working body.

FIGS. 10A to 10C show side, end, and perspective views, respectively, of one variation of an end link which may be used as a terminal link of the working body.

FIG. 17A shows a perspective view of one variation of the pod assembly with the top cover and optional basket insert removed for clarity.

FIGS. 19A and 19B show side and top views, respectively, of another variation of the pod assembly where an angled pod assembly may be mounted on a distal end of the working body.

FIGS. 22A to 22C show cross-sectional side, front, and top views, respectively, of one variation of stapler assembly.

FIG. 22D shows a top view of the anvil of the stapler assembly.

FIGS. 25A and 25B show perspective views of another variation of the approximation device having an actively or passively curved working body.

FIG. 25C shows a detail view of the actuation handle of the device in FIGS. 25A and 25B.

DETAILED DESCRIPTION OF THE INVENTION

A system for tissue approximation and fixation is described which may be utilized for approximating tissue regions from within a hollow body organ, such as the stomach, esophageal junction, and other portions of the gastrointestinal tract. The system may be advanced within a body through a variety of methods, e.g., transorally, transanally, endoscopically, percutaneously, etc., to create one or several divisions or plications within the hollow body organ. At least two devices may be utilized as part of the system, a tissue acquisition and folding system and a tissue stapling or fixation system, although it is contemplated that both devices can be integrated into a single mechanism. Each of these devices may be configured to efficiently operate with one another to provide optimal methods and devices for at least acquiring, approximating, and stapling regions of tissue from within the hollow body organ in a minimally invasive manner.

Figure 1:
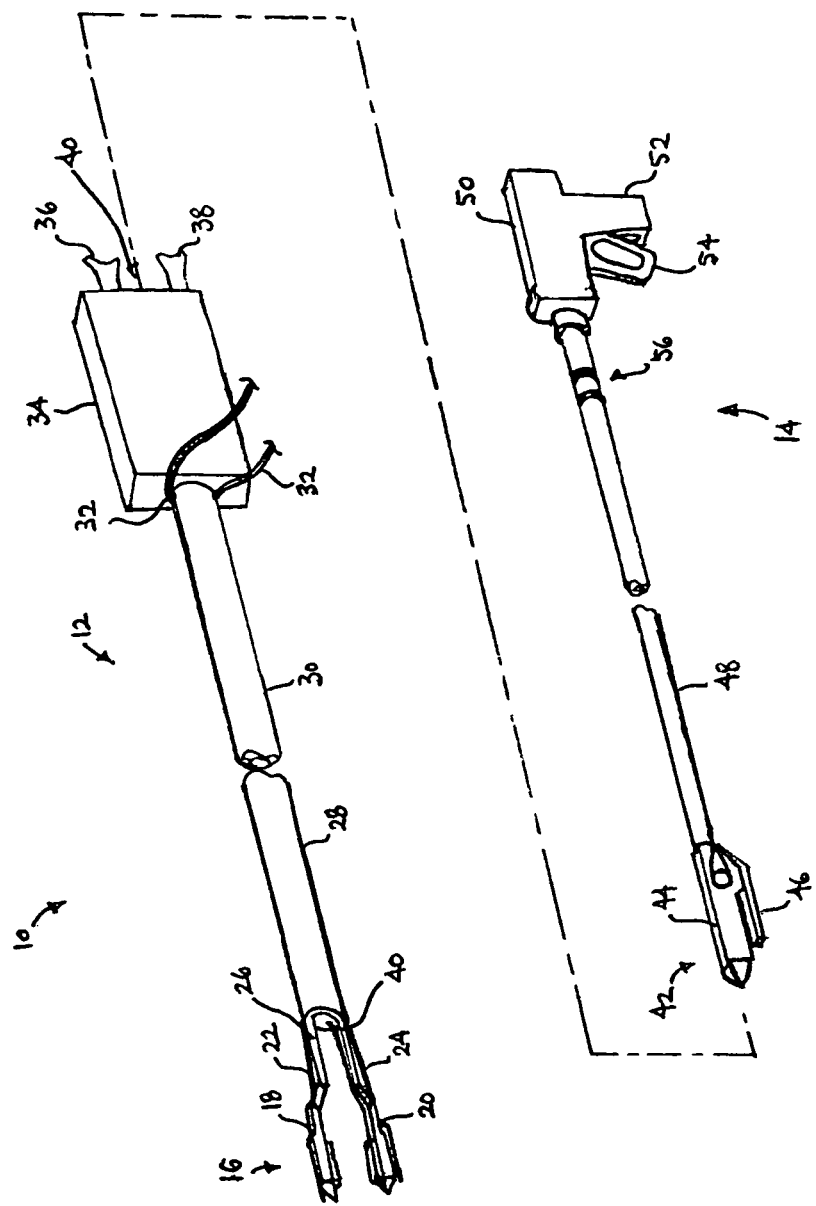
FIG. 1 shows a perspective view of a tissue folding and fixation assembly which may be advanced within a hollow body organ to reconfigure the tissue from within.

Turning now to the figures, the system will first be described generally in which one variation of system 10 is shown in FIG. 1, which illustrates a perspective view of folder assembly 12 and fixation assembly 14. Folder assembly 12, which is described below in greater detail, may be comprised generally of pod assembly 16, which may be used to initially acquire and approximate the tissue to be folded. Pod assembly 16 may have a first pod member 18 and a second pod member 20, each of which may be independently articulatable to form a first compact configuration and a second larger, expanded configuration. Each of first and second pod members 18, 20 may be connected to respective first and second actuation rods 22, 24 on the distal end of a yoke member 26, as described in further detail below.

Pod assembly 16 may be located at the distal end of working body 28 which may be configured as a flexible shaft having one or several lumens defined through the length of the working body 28. The working body 28 may be covered by a sheath or covering 30 to enhance the lubricity of the shaft as well as to maintain the interior of the body 28 clear from body fluids and debris and provide a seal to allow insufflation of the target organ. Various materials may be utilized for sheath 30 including various plastics, elastomers, latex, polyurethane, thermoplastics, e.g., PTFE, FEP, silicone, PVC, Tecoflex®, Pebax®, etc., so long as they are preferably biocompatible.

A number of vacuum tubes 32 may also be routed through the length, or a partial length, of the working body 28 to pod assembly 16. The figure shows vacuum tubes 32 entering the working body 28 at its proximal end. Alternatively, vacuum tubes 32 may enter working body 28 at some distal point along the length of body 28 or vacuum tubes 32 may enter working body 28 through handle 34. In either case, vacuum tubes 32 may be positioned within one or several lumens defined through working body 28 and placed in fluid communication with respective first and second pod members 18, 20 to facilitate in vacuum actuation of tissue, as further described below. The proximal ends of vacuum tubes 32 may be connected to one or more vacuum pumps (not shown). Furthermore, vacuum tubes 32 may utilize braided materials, e.g., stainless steel, superelastic materials such as Nickel-Titanium alloy, integrated throughout to prevent kinking or pinching of the tubes 32. Such vacuum tubes 32 may also accommodate insertion of a snare or grasper type device that can be inserted once tissue is acquired to mechanically grasp the invaginated tissue, depending on the type of tissue manipulation desired. An example of a "gooseneck" snare by Microvena, Inc. which may be used with the vacuum tubes 32 is described in further detail in U.S. Pat. No. 5,171,233, which is incorporated herein by reference in its entirety.

The proximal end of working body 28 is operatively connected to handle 34. Also connected to handle 34 are first and second actuators 36, 38 which may be used to actuate first and second pod members 18, 20, respectively, from the first compact configuration to the second larger, expanded configuration. Each actuator 36, 38 may be actuated individually to control a corresponding pod member independently of the other pod member or may be actuated simultaneously, as described later herein. Main lumen 40 may be defined throughout the length of working body 28 and through handle 34 such that fixation assembly 14 may be advanced and withdrawn through the folder assembly 12. Fixation assembly 14 comprises, in part, stapler assembly 42 connected via flexible shaft 48 to a stapler handle 50. Stapler assembly 42 generally comprises staple cartridge 44, within which one or more staples are housed. Stapler assembly 42 may also have an optional tapered distal end to facilitate insertion of the device into or past tissue, as described in further detail below. Anvil 46 is in apposition to staple cartridge 44 and is used to provide a staple closure surface when tissue to be affixed is adequately positioned between staple cartridge 44 and anvil 46. With stapler assembly 42 connected at the distal end of flexible shaft 48, handle 50 is connected at the proximal end of shaft 48. Handle 50 may generally comprise a housing and grip 52 in apposition to actuation handle 54. Handle 50 allows for the surgeon or user to hold and manipulate fixation assembly 14 with grip 52 while articulating stapler assembly 42 between an open and close configuration via actuation handle 54. Moreover, the configuration of handle 50 allows the surgeon or user to articulate stapler assembly 42.

When fixation assembly 14 is advanced within folder assembly 12, stapler assembly 42 is preferably in a closed configuration. When stapler assembly 42 has exited working body 28, staple cartridge 44 may be articulated into an open configuration when positioned between yoke 26 to receive the tissue folded between pod members 18, 20. Stapler assembly 42 may then be advanced distally over the folded tissue and clamped close over the tissue for deploying the staples. To avoid damaging tissue surrounding pod assembly 16 and to facilitate proper stapling, one or several insertion indicator(s) 56 may be defined along a portion of flexible shaft 48 preferably near a proximal end of shaft 48, to aid the user in knowing when stapler assembly 42 may be safely articulated while fixation assembly 14 is positioned within working body 28. Indicators 56 may be configured to align with a proximal end of folder handle 34 to correspondingly indicate, e.g., a position of fixation assembly 14 relative to folder assembly 10 when stapler assembly 42 may be opened, and/or how far distally fixation assembly 14 may be advanced relative to folder assembly 10 to engage the folded tissue, etc. In addition to visual indicators, a mechanical indication, such as a stop or detent may be employed to give the operator a tactile indication of "safe to open" and "safe to clamp" device positions.

Figure 2A:
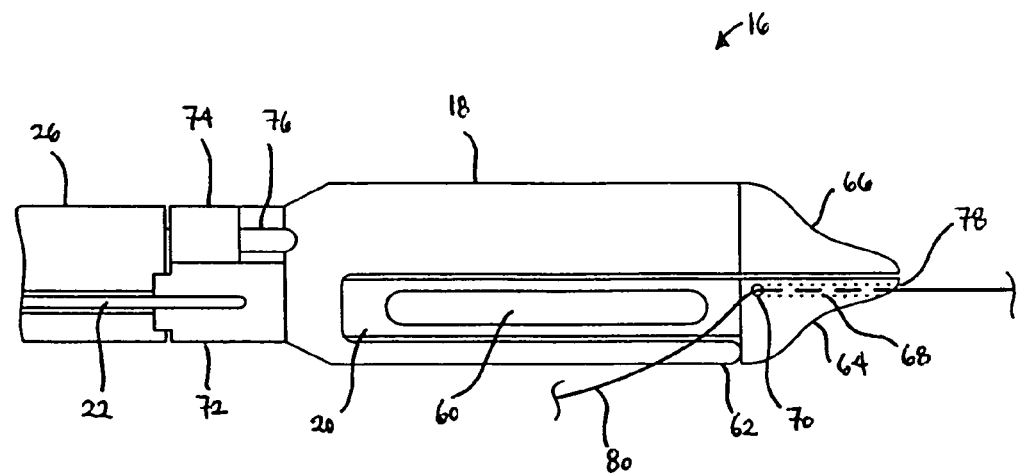
FIGS. 2A and 2B show side and top views, respectively, of a pod assembly which may be used to manipulate tissue.
Figure 2B:
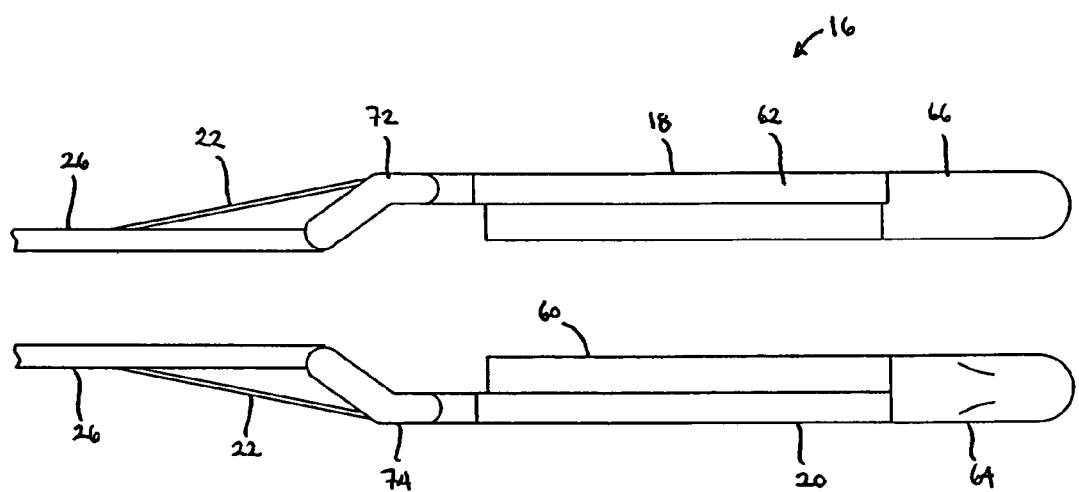

A brief description of the pod assembly 16 will be given in order to describe how the tissue may be manipulated by the devices described herein. A more detailed description will be given below. Side and top views of one variation of pod assembly 16 is shown in FIGS. 2A and 2B, respectively. Pod members 18, 20 may each be comprised of a vacuum chamber or opening 60 into which tissue may be drawn therewithin. A vacuum tube 76 may be seen in FIG. 2A leading to first pod member 18. The opening of vacuum chamber 60 may be slotted along a direction parallel to a longitudinal axis of the working body 28, or may be transverse to the parallel axis; alternatively, the opening may be defined a variety of shapes, e.g., oval, elliptical, etc. Adjacent to and preferably parallel with vacuum chamber 60 is tensioning arm or member 62, which may have a length equal to that of vacuum chamber 60. Alternatively, a length of tensioning member 62 may be less than or greater than that of vacuum chamber 60. The distal end of each pod member may have a flexible and/or atraumatic tip 64, 66 made from any number of polymers to facilitate the guidance of pod assembly 16 into the hollow body organ without damaging tissue along the way.

A guidewire may optionally be used with the folder assembly 12 during initial deployment and positioning within the hollow body organ in a manner similar to a catheter for guiding pod assembly 16 to a predetermined position. Accordingly, an optional guidewire lumen may be defined in one or both atraumatic tips 64, 66; as seen in tip 64, guidewire lumen 68 may be defined therein with guidewire 80 extending through from proximal guidewire opening 70 to distal guidewire opening 78. Proximal and distal guidewire openings 70, 78, respectively, may both be defined on, e.g., atraumatic tip 64, to enable exchange of the guidewire through one or both tips; however, guidewire openings 70, 78 may also be defined on other regions of pod members 18, 20 depending upon the type of exchange capability desired.

Both first and second pod members 18, 20 may each be adapted to pivot on respective hinge members 72, 74 such that in a first compact configuration, first and second pod members 18, 20 may be immediately adjacent to one another. As shown, first pod member 18 has a corresponding tensioning member 62 aligned adjacent to member 18 and second pod member 20 has a corresponding tensioning member 90 also aligned adjacent to member 20. In moving to a second expanded configuration, pod member 18 with tensioning member 62 and pod member 20 with tensioning member 90 may be translated via actuation rods 22 into opposing radial directions from one another relative to yoke 26, as shown in FIG. 2B.

Figure 2C:
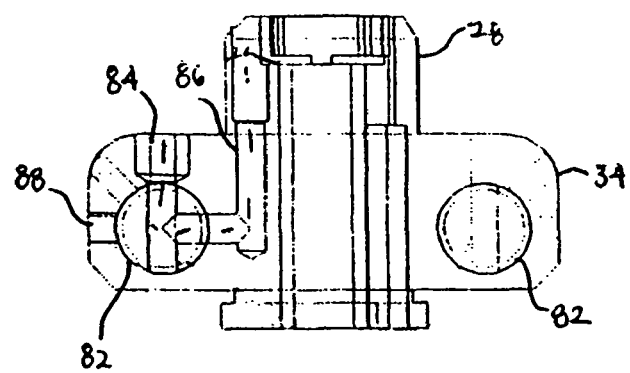
FIGS. 2C to 2E show cross-sectional side views of rotatable valves which may be used control the vacuum force within the device.
Figure 2D:
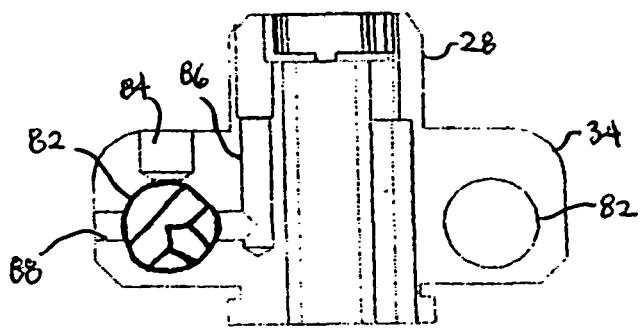
Figure 2E:
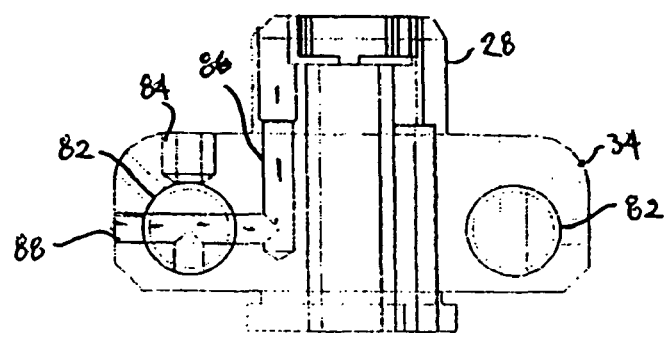

The vacuum force which may be used to draw in the tissue may be controlled through a number of various methods. One variation is illustrated in FIGS. 2C to 2E, which show how valves 82 may be integrated into handle 34 for controlling the vacuum force. As seen in the cross-sectional side view of FIG. 2C, valve 82 may be configured to rotate and align such that vacuum lumen 84 comes into fluid communication with lumen 86, which leads to working body 28. Vacuum lumen 84 may be connected to a vacuum control unit (not shown), e.g., a standard luer assembly (QOSINA, model #99720), to allow for air to be drawn through lumen 86 and create the vacuum at the distally-located pod members. FIG. 2D shows how valve 82 may be rotated by some degree, e.g., 45° relative to a longitudinal axis of handle 34, such that the vacuum force is no longer in fluid communication with lumen 86. FIG. 2E shows how valve 82 may be further rotated, e.g., 90° relative to a longitudinal axis of handle 34, such that lumen 86 is in fluid communication with venting lumen 88 to allow for venting of the assembly. A second valve, as shown, may be integrated in handle 34 to allow for the independent control of the vacuum force in the second pod member. Each of the vacuum lumens 84 may be fluidly connected to a common or independent vacuum pump. Moreover, rather than having two independently controllable valves 82, a single valve 82 may be utilized to control the vacuum force in both pod members, depending upon the desired results. The above variations are intended to be illustrative and are not intended to be limiting in their scope of the disclosure in the various possible configurations and methods available for controlling the vacuum force.

Figure 3A:
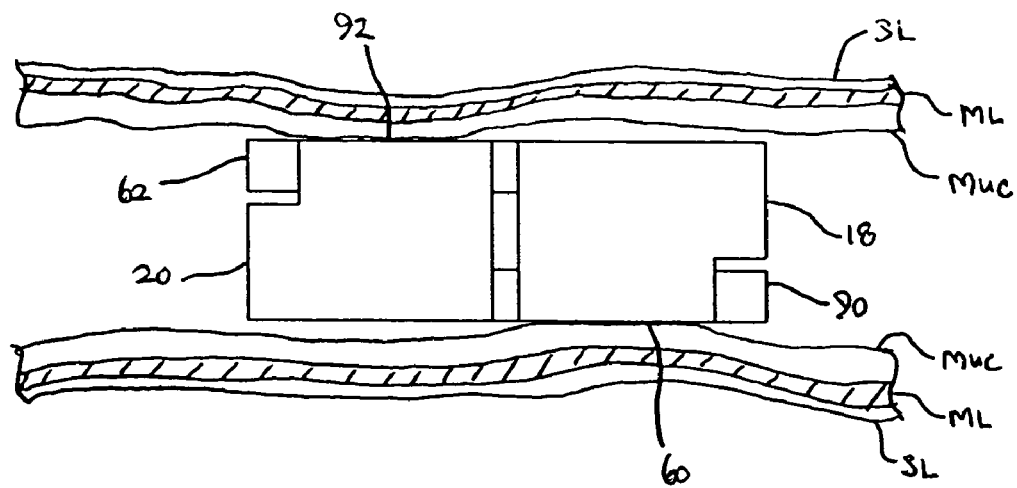
FIGS. 3A and 3B show an end view of a pod assembly which has been translated with respect to one another while adhering tissue.
Figure 3B:
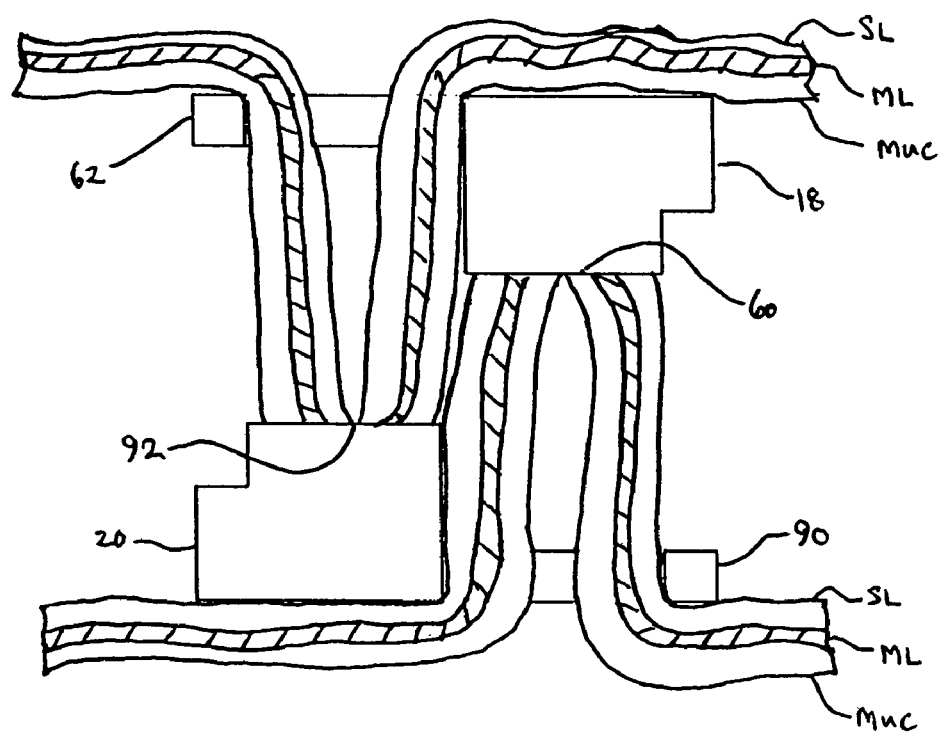

FIGS. 3A and 3B show the movement of pod members 18, 20 relative to one another in reconfiguring the surrounding tissue. FIG. 3A shows an end view of pod members 18, 20 which have been advanced while in a closed configuration into, e.g., a stomach, and positioned adjacent to a region of interior tissue to be reconfigured. When desirably positioned, a vacuum force may be applied within one or both pod members 18, 20 such that tissue begins to enter within one or both of the vacuum chambers or openings 60, 92.

The different linings of the stomach, which include the mucosal layer MUC, muscular layer ML, and serosal layer SL, are shown in cross-section. The vacuum force may be applied such that at least the mucosal layer MUC of opposing portions of tissue, e.g., an anterior wall AW and posterior wall PW, are drawn into vacuum chambers 60, 92 and the tissue is sufficiently adhered to the pod members 18, 20. While the vacuum force is applied, pod members 18, 20 may be translated away from one another in opposing direction such that the adhered tissue is drawn between each pod member 18, 20 and respective tensioning member 62, 90 such that at least two adjacent folds of tissue are created to form an overlap region of tissue, as shown in FIG. 3B. Alternatively, rather than having both pod members 18, 20 move opposite to one another, one pod member may be held stationary while the other pod member is translated radially. In addition, it may be desirable to acquire tissue and translate a first pod, and subsequently acquire tissue and translate a second pod as a separate step to enhance tissue acquisition and positioning. After the tissue has been acquired through any of the methods described above, the device may be curved or manipulated, as described in further detail below. The tissue may then be affixed through one of the methods as described herein.

Figure 3C:
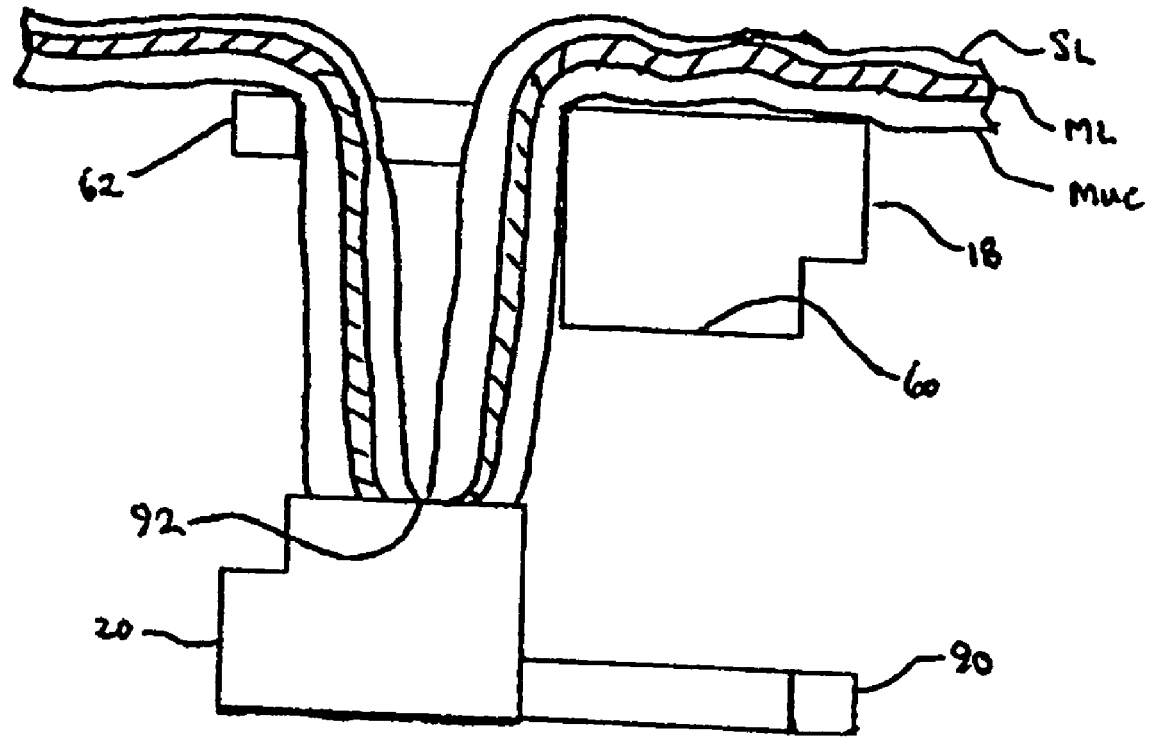
FIG. 3C shows an end view of a pod assembly in which a single pod member has been actuated with tissue adhered thereto.

Similarly, it may be desirable to actuate only one pod and tensioning member to acquire a single, longitudinal fold, for use in treatments such as GERD or to exclude certain portions of the wall of the body organ. Examples of other treatments are described in further detail in co-pending U.S. patent application Ser. No. 10/417,790, which has been incorporated by reference above. Accordingly, similar to the tissue acquisition in FIG. 3B, FIG. 3C shows how the device may be utilized for acquiring and tensioning a single layer of tissue. In such an acquisition, the vacuum force may be simply shut or turned off in one of the pod members, in this case, pod member 18 while the vacuum force in pod member 20 may remain activated.

Figure 4:
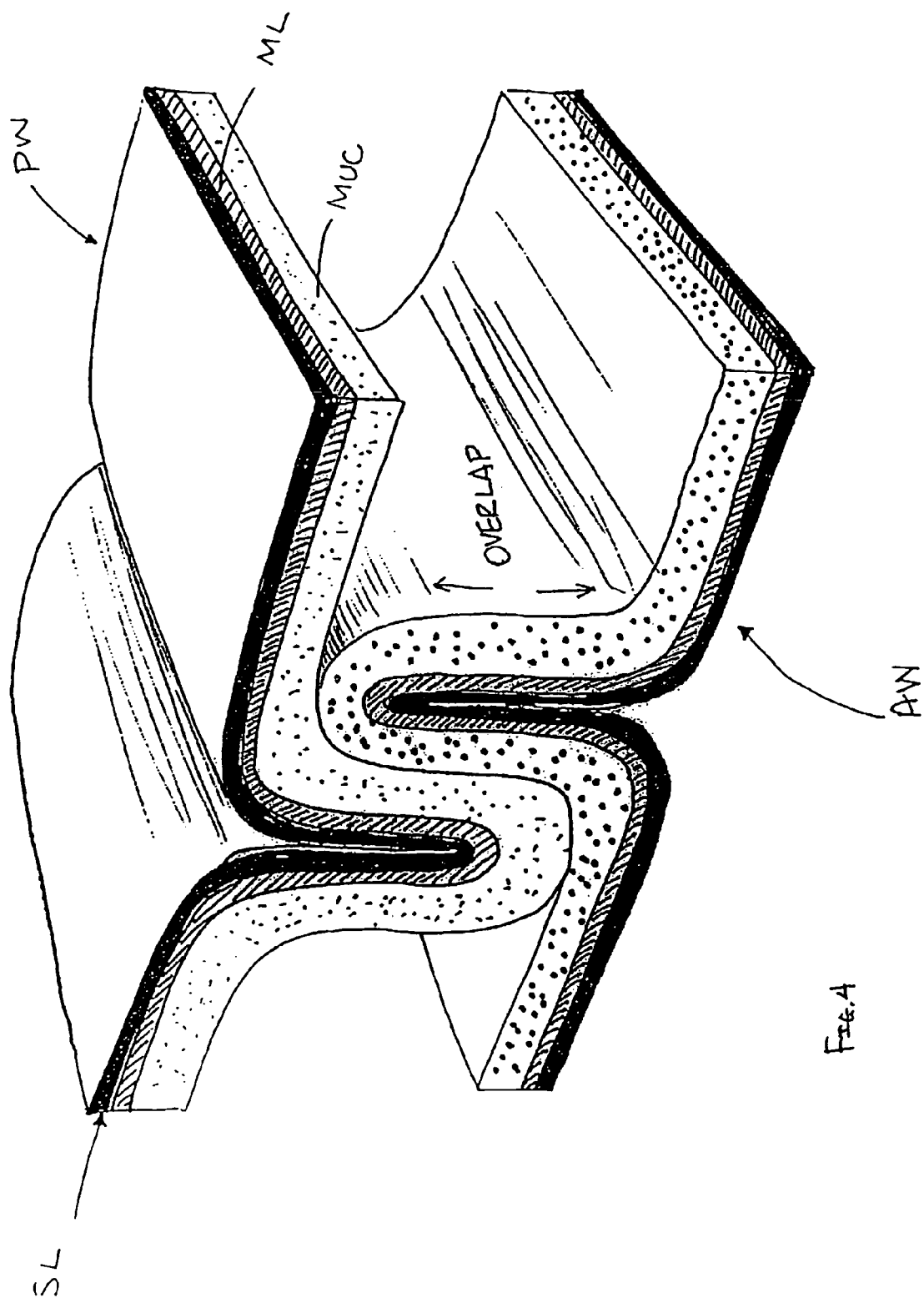
FIG. 4 shows a representative illustration of the tissue overlap which is created by the translated pod assembly.

FIG. 4 shows a representative illustration of the tissue overlap which is created by the devices, as described herein. The devices are removed for clarity to better illustrate the tissue overlap formation. FIG. 5 shows an example of a cross-sectional side view of tissue overlap 100 where staple cartridge 44 and anvil 46 have been articulated and clamped onto overlap 100 for stapling. When the tissue overlap 100 is created by folder assembly 12, overlap 100 preferably includes an overlap of at least the muscular layer ML and serosal layer SL to ensure a secure anchoring platform for the staples or fasteners to maintain the durability of the tissue overlap 100. A more detailed discussion may be found in U.S. patent application Ser. No. 10/188,547 filed Jul. 2, 2002 and entitled "Method And Device For Use In Tissue Approximation And Fixation", which is incorporated herein by reference in its entirety.

Folder Assembly

Figure 6A:
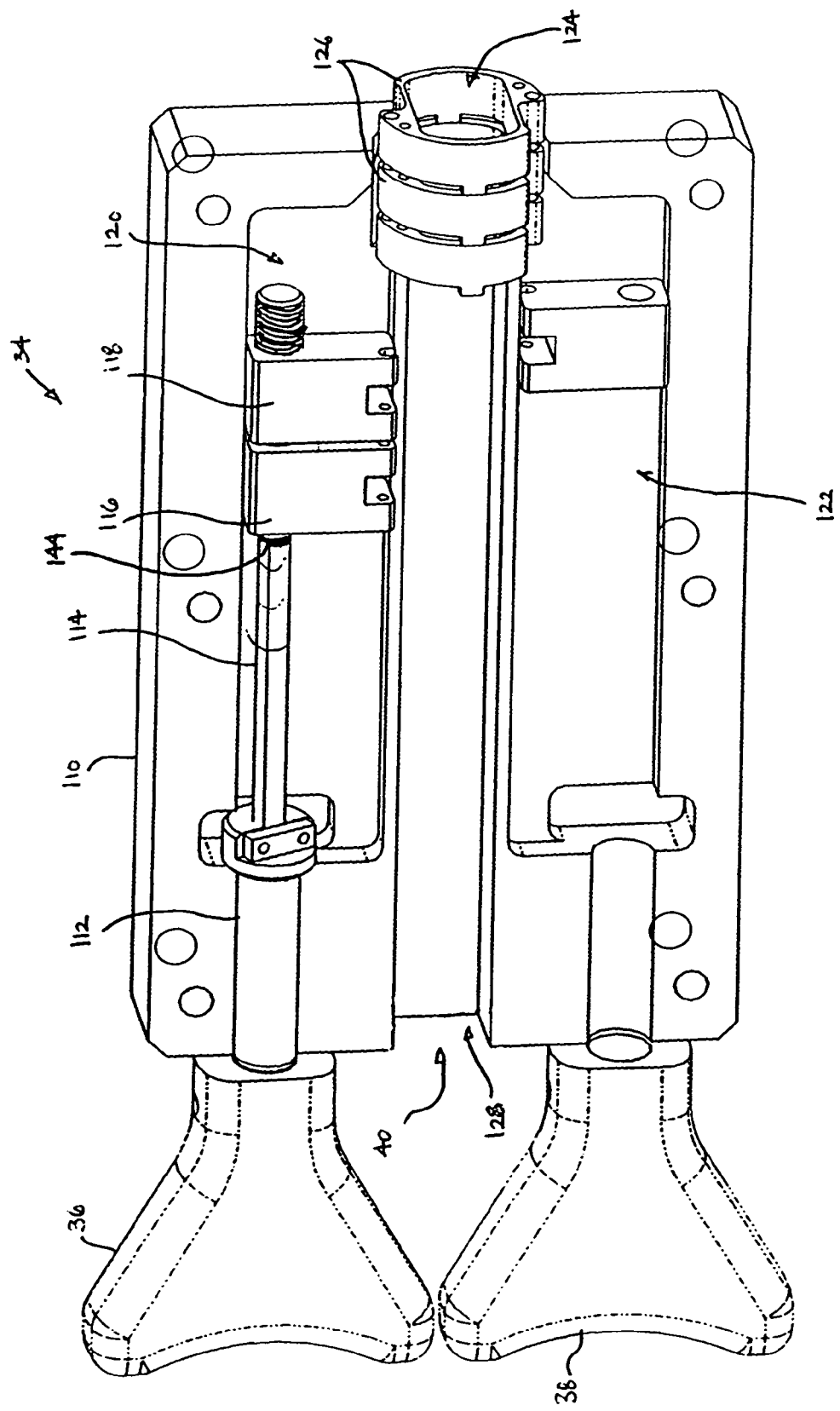
FIG. 6A shows a partial assembly of the handle for the folder assembly.

Folder assembly 12 may typically comprise a handle 34 at a proximal end of the assembly 12, as described above. Handle 34 may comprise housing 110 which may enclose a pod actuation assembly within. FIG. 6A shows a partial assembly of handle 34 to illustrate the internal mechanisms. As described above, first actuator 36 may be used to manipulate first pod member 18 from a first configuration to a second configuration. Pod manipulation may be achieved, in part, by having first actuator 36 connected via shaft 112 to transmit a torquing force to threaded carriage shaft 114. The carriage shaft 114 is preferably free-floating, i.e., can translate longitudinally inside the shaft 112. Proximal mount 116 may be free to rotate about the carriage shaft 114, but it is preferably constrained to inhibit translation of mount 116 relative to the carriage shaft 114. Distal mount 118 may be slidingly positioned over carriage shaft 114, typically by a threaded connection. This threaded connection maintains a fixed relative distance between the mounts so that the mounts and the carriage shaft 114 may translate longitudinally as a unit. Proximal mount 116 and distal mount 118 may be anchored to the proximal ends of the actuation rod and tubing member, which houses the actuation rod, as described further below. Each mount 116, 118 and shaft 112 may be configured to be free-floating, i.e., translate longitudinally unconstrained, inside of shaft 112 within first actuation channel 120 to accommodate the lateral movement of working body 28 and the subsequent translational movement of the proximal ends of actuation rods within housing 110. Stop 144, e.g., a ring or shoulder defined upon shaft 114, may be positioned proximally of mount 116 to prevent the longitudinal movement of mount 116 along shaft 114. Mounts 116, 118, however, may be configured to maintain a fixed distance relative to one another when longitudinally translated as a unit. Corresponding mounts may be configured to translate along a second shaft (not shown) within second actuation channel 122 for a second actuation rod. Mounts 116, 118 may thus translate as a unit until actuator 36 is rotated.

The handle mechanism 34 helps to ensure that relative or unwanted movement of the pods during flexing of the shaft of the folder in minimized or eliminated. Additionally, tubes 136, as further described below, function so that the shaft of the device is not loaded during actuation. These tubes 136 help to support the actuation load, but still allow sufficient shaft flexibility.

Figure 6B:
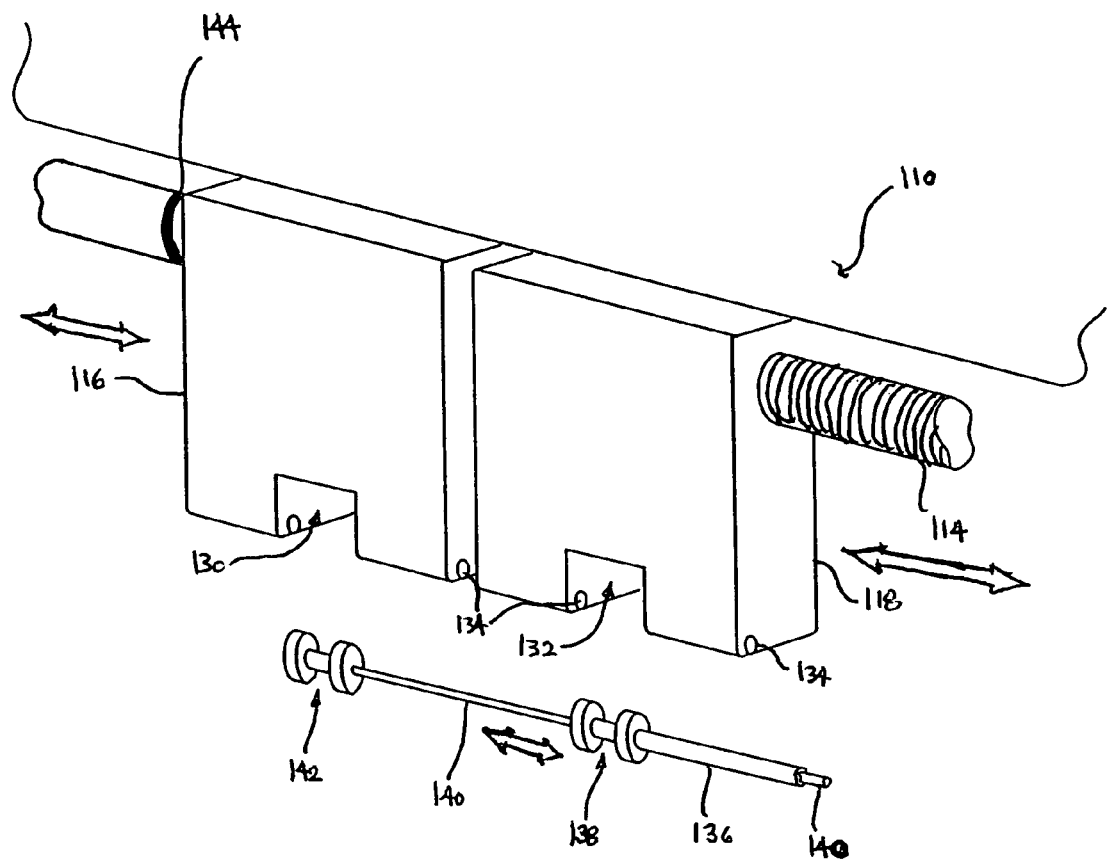
FIG. 6B shows a detail view of an exploded assembly of anchoring mounts and a proximal portion of an actuation rod assembly.

As shown in FIG. 6B, which is a detail view of an exploded assembly of mounts 116, 118 and their corresponding actuation rod assembly. Proximal mount 116 may have a rod anchoring region 130 defined along one side and distal mount 118 may have tubing anchoring region 132 defined along one side and collinearly with rod anchoring region 130. Actuation rod 140 may be slidingly positioned within tubing member 136 and configured to slide longitudinally therewithin when translated relative to tubing member 136 for actuating a pod member. Actuation rod 140 may be anchored to proximal mount 116 by securely positioning actuation rod anchor 142 within anchoring region 130. Likewise, tubing member 136 may be anchored to distal mount 118 by positioning tubing anchor 138 within tubing anchoring region 132. Each mount 116, 118 may have collinearly defined openings 134 to accommodate rod tubing 136 and actuation rod 140 when they are secured within anchoring regions 130, 132. As actuator 36 is rotated, carriage shaft 114 is rotated about its longitudinal axis to urge mount 118 towards or away from mount 116, as shown by the arrows, depending upon which direction carriage shaft 114 is rotated. When mounts 116, 118 are urged towards one another, actuation rod 140 is forced to slide distally within and relative to tubing 136 to urge the pod member, e.g., into its expanded configuration. Similarly, when mounts 116, 118 are urged away from one another, actuation rod 140 is forced to slide proximally within and relative to tubing 136 to urge the pod member, e.g., into its compact configuration.

As further seen in FIG. 6A, main lumen 40 may be defined through a length of housing 110 to accommodate insertion of the fixation assembly 14 therethrough. The proximal opening 128 of lumen 40 may be gasketed to allow for the insufflation of the hollow body organ using the device as well as to prevent the leakage of bodily fluids and particles. Distal opening 124 may likewise be gasketed and is further configured to accept a proximal end of working body 28. The individual links 126 of one variation of the proximal end of working body 28 are shown in the figure to illustrate an example of the mating between working body 28 and housing 110.

Figure 7:
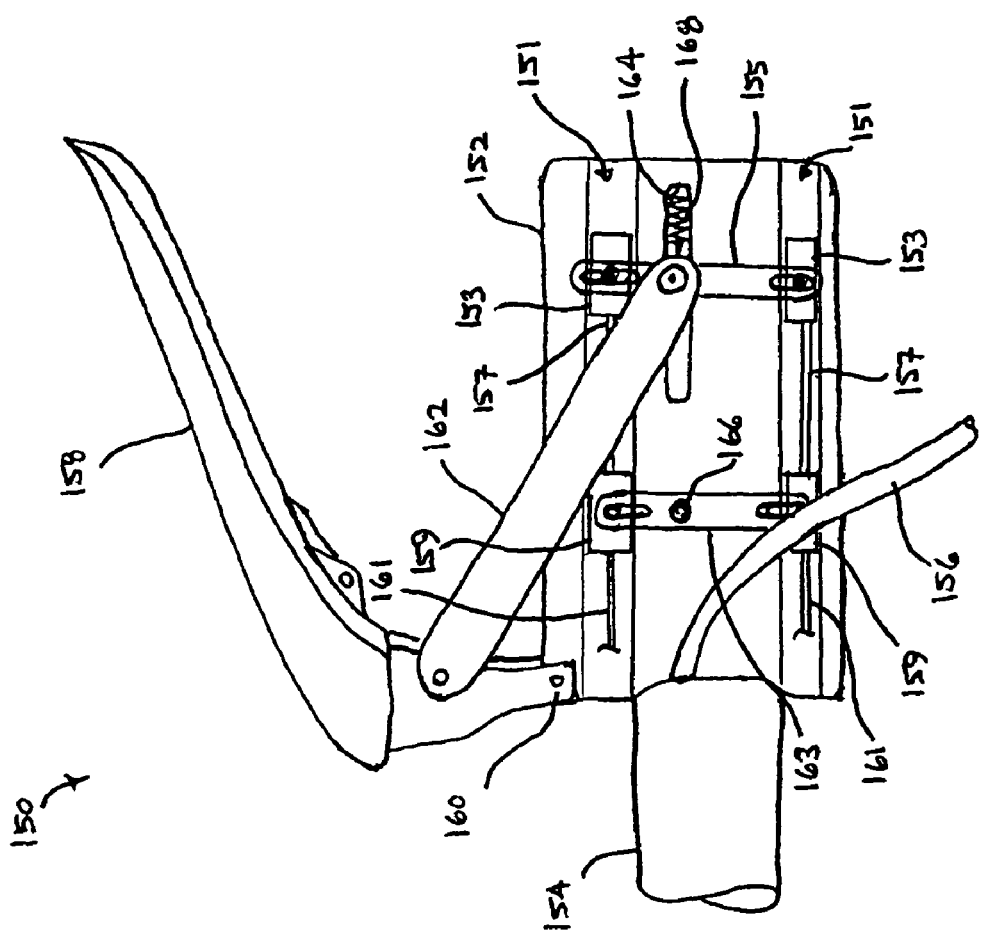
FIG. 7 shows a side view of an alternative variation on a dual actuator folder assembly housing.

An alternative variation on the folder assembly housing is shown in dual actuator assembly 150 in FIG. 7. In this variation, a side view of housing 152 is seen in which a single actuator or lever 158 may be utilized to manipulate both pod members simultaneously. Lever 158 may be configured to rotate about pivot 160 to urge actuation link 162 to translate within actuation slot 164 to simultaneously manipulate both pod members rather than having two or more separate controls. The proximal end of working body 154 may be seen connected to housing 152 and vacuum tube 156 may be seen leading into working body 154 for communication with the folder assembly.

When lever 158 is depressed, actuation link 162 translates proximal linkage 155 within actuation slot 164. Proximal linkage 155 is free to rotate about a pivot during flexure of the working body 154 and actuates proximal blocks 153 to slide longitudinally within channels 151, which are defined through housing 152. A spring or biased element 168 may be positioned within slot 164 to place a biasing force on link 162 and lever 158 such that the assembly maintains a neutral or fixed orientation, if desired. Proximal blocks 153 are connected to actuation rods 157 which may extend distally through distal blocks 159 and further into working body 154. Distal blocks 159 may be pivotally connected to distal linkage 163, which may be pivotally affixed to housing 152 via pivot 166 while allowing distal blocks 159 to translate within channels 151. Tubing members 161 may be configured to allow passage of actuation rods 157 therethrough while remaining connected to distal blocks 159. Although the specific configuration of this variation is shown and described, this is not intended to be limiting and is illustrative of one variation of a handle which allows for single activation and tunable mechanical advantage.

The working body 28, which extends between the handle and the pod assembly located at the distal end of the working body 28, may be comprised of a plurality of links or knuckles generally cylindrical in shape and positioned adjacently to one another, as shown and described above in FIG. 6A. A transition link or knuckle 170 is shown in FIGS. 8A to 8C, which show side, end, and perspective views, respectively, of a link which may serve as a transitional link between the handle and the length of the working body 28. As seen in the side view of FIG. 8A, transition link 170 may have a proximally located cylindrically-shaped flange 172 with a diameter greater than a diameter of the body portion 176. Flange 172 may serve to help anchor the working body 28 to the handle by fitting within a cavity defined in the handle and shaped to receive flange 172. A transition portion 174 may taper a region of the link 170 down to body portion 176. The end view in FIG. 8B shows main lumen 178 defined through the length of link 170. Main lumen 178 may be shaped with parallel sides opposite to one another to allow fixation assembly therethrough in a specified configuration, as described below in further detail.

Although the transition link 170 is shown to be generally cylindrical in shape, it may alternatively be configured in a variety of shapes, e.g., ovular, elliptical, etc. Transition link 170 may also range in diameter, e.g., 0.75 in. (about 1.90 cm), so long as it is wide enough to accommodate the insertion of fixation assembly 14 therethrough yet small enough to be inserted into the body, e.g., through the esophagus. Link 170 may also range in length, e.g., 1.125 in. (about 2.85 cm), depending upon the desired design characteristics. Moreover, transition link 170 may be made from a variety of materials, e.g., metals, plastics, etc., so long as it is biocompatible. For example, transition link 170 may be made from stainless steel, nickel-titanium alloys, or it may be molded from plastics and thermoplastics, e.g., polycarbonate resins such as Makrolon® (Bayer Aktiengesellschaft, Germany).

FIGS. 9A to 9C show side, end, and perspective views, respectively, of an example of a knuckle or link 180 which may be used to form at least part of the working body 28. This link variation 180 may be made from a material similar to that of transition link 170. It may also range in diameter, e.g., 0.69 in. (about 1.75 cm), so long as link 180 is wide enough to accommodate the insertion of fixation assembly 14 therethrough yet small enough to be inserted into the body, as above. Lumen 182 may be configured such that it is keyed to allow fixation assembly 14 to pass through in a specified configuration; thus, in this particular variation, lumen 182 is shown as having straight walls 196, which may be parallel and opposite to one another. Link 180 may also define one or more routing channels 184 around the circumference of the link 180 to allow for the routing of various wires or tubes therethrough along a length of working body 28. Link 180 shows a variation in which two routing channels 184 may be defined on opposing sides around the circumference. As further seen in FIG. 9A, link 180 may further define peripherally located actuator rod lumens 196 and additional routing lumens 188 in link 180 outside of lumen 182. This variation shows at least two of each lumen 186, 188 defined on opposing sides of link 180, although they may be defined elsewhere around link 180 in other variations depending upon the number of lumens desired as well as spacing considerations.

FIG. 9B shows a side view of link 180 having least two protrusions 190 extending from a first surface 192 on either side of the periphery of link 180. Protrusions 190 may extend from first surface 192 at a distance, e.g., 0.040 in. (about 0.10 cm), so that when multiple links are aligned with one another, protrusions 190 abut the second surface 194 of an adjacent link, as shown in FIG. 9C. When multiple links are aligned, lumen 182, as well as actuator rod lumen 186 and additional routing lumen 188 may be aligned with adjacent links to form the overall main lumen 40 and actuator rod lumen, as described above. Alternatively, overall flexibility of the device may be achieved by a single structure that contains axial slots along its length, such as that shown in U.S. Pat. No. 5,685,868, which is incorporated herein by reference in its entirety. Similarly, the working body may be formed of a single piece, flexible component, such as a polymer extrusion and/or multi-lumen co-extruded design, a braid, or other such known materials.

Figure 9D:
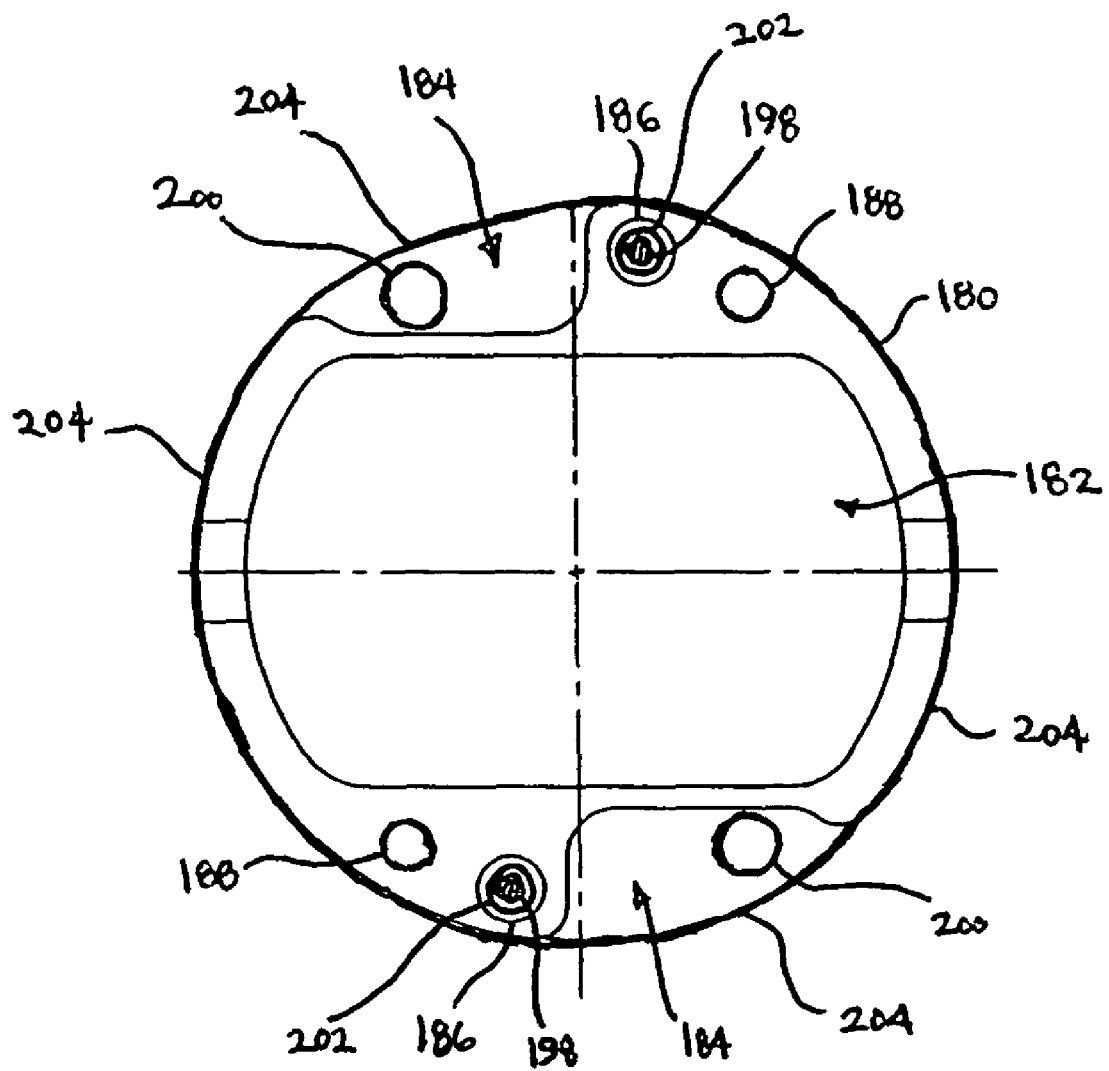
FIG. 9D shows an end view of a link having cross-sections of some of the various internal lumens which may be routed through the working body.

FIG. 9D shows an end view of link 180 in one variation where actuation rod 198 is routed through actuator tubing member 202 and both may be disposed within actuator rod lumen 186 such that both extend through a length of working body 28. Vacuum tubes 200 may also be positioned within routing channels 184 and the entire assembly may be covered by sheath or lining 204, which may extend along at least a portion of working body 28, and preferably over the entire length of working body 28. Sheath or lining 204, as mentioned above, may be used to enhance the lubricity of the working body 28 as well as to maintain the interior of the body 28 clear from body fluids and debris and to provide sealing to enable insufflation of the target area. Various materials may be utilized for sheath 204 including various plastics, elastomers, latex, polyurethane, thermoplastics, e.g., PTFE, silicone, PVC, FEP, Tecoflex®, Pebax®, etc., so long as they are preferably biocompatible. Moreover, sheath 204 may also utilize braided materials integrated throughout to increase tensile, compressive, and/or torsional strengths of sheath 204 as well as to provide for resistance against kinking or pinching between individual links or when working body 28 is flexed.

FIGS. 10A to 10C show side, end, and perspective views, respectively, of one variation of end link 210, which may be utilized as the terminal or final link of working body 28. End link 210, much like links 180, may define a keyed lumen 212, routing lumens 214, and actuator rod lumen 218. Lumen 216 may also be defined and it may be counterbored to accommodate a mechanical fastener for connecting the yoke member. As the terminal link, actuator tubing member 202 may be terminated and attached to end link 210 at lumen 218 while allowing the actuator rod to extend through and beyond lumen 218 for attachment to the pod assembly. Side and perspective views in FIGS. 10B and 10C further show detent 222, which may be defined along the end surface of link 210 for receiving and/or engaging the yoke member. Moreover, end link 210 may be made from the same or similar materials as described above for the other links. However, end link 210 is preferably made from a material such as a metal, e.g., stainless steel, or polycarbonate, which may withstand forces generated during pod and tissue manipulation. The end link 210, or a similar or additional link, may also be used to terminate any covering placed over the working body 28 as heretofor described in FIG. 9D.

Figure 11:
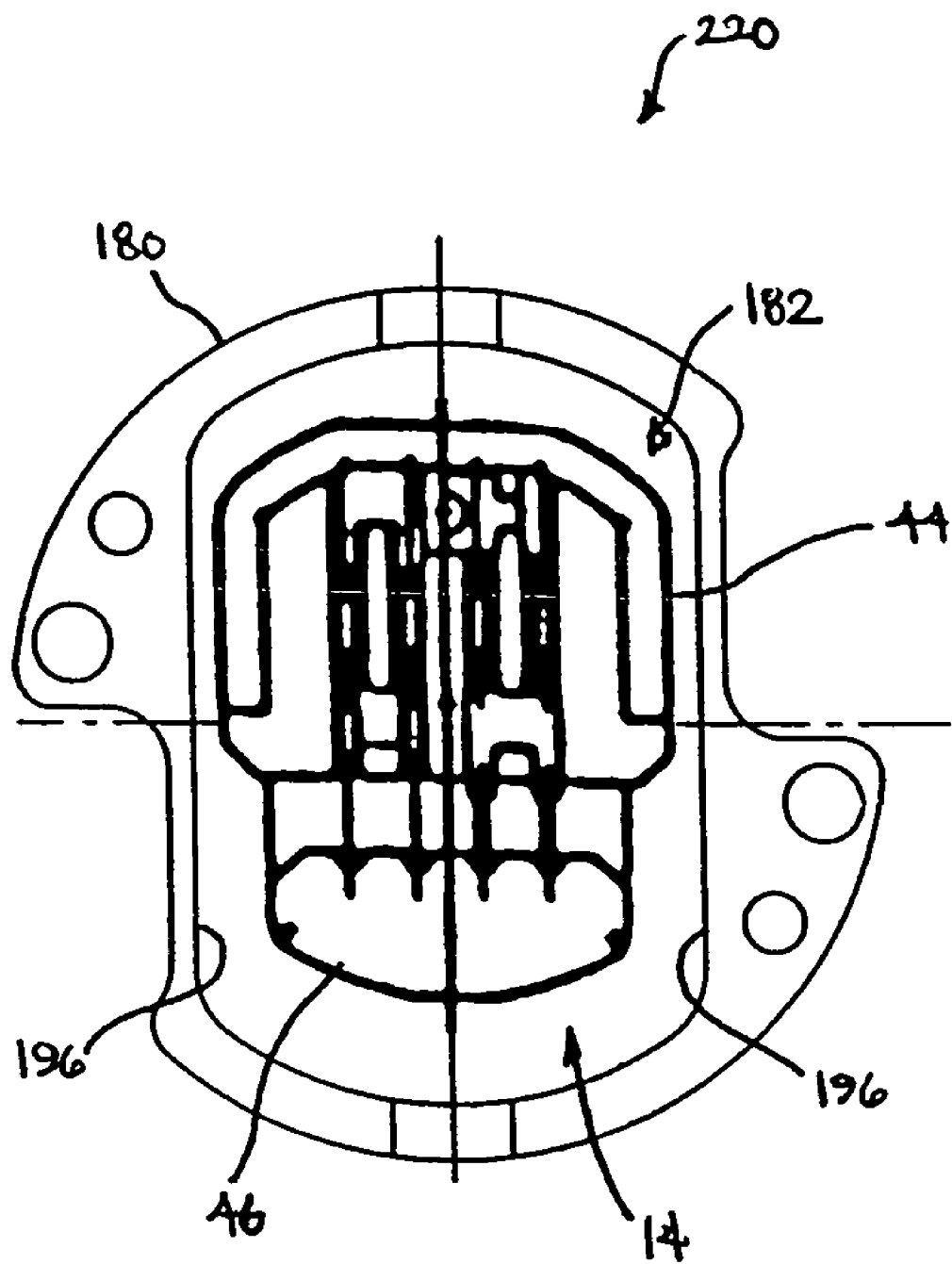
FIG. 11 shows an end view of a link with the fixation assembly positioned within for advancement through the main lumen of the working body while maintaining a consistent orientation.

FIG. 11 shows an end view of link 180 with staple cartridge 44 and anvil 46 of fixation assembly 14 positioned within lumen 182 for advancement through working body 28. As seen, lumen 182 may be configured such that it is keyed to allow fixation assembly 14 to pass through in a specified orientation. Walls 196, which may be parallel and opposite to one another, may thus be sized and configured to prevent fixation assembly 14 from rotating about its own longitudinal axis within lumen 182 during advancement and deployment from the main lumen. Maintaining fixation assembly 14 in a predetermined orientation relative to working body 28 and pod assembly 16 also helps to ensure that when staple cartridge 44 and/or anvil 46 are actuated to open for clamping over folded tissue, a known orientation of fixation assembly 14 relative to the folded tissue is maintained for tissue fixation. Other configurations for keying lumen 182 to fixation assembly 14 may be available in other variations; the shape of lumen 182 and the cross-sectional shape of fixation assembly 14 are not intended to be limiting but are merely illustrative of one possibility of creating and/or configuring a keyed orientation between the two assemblies.

Figure 12B:
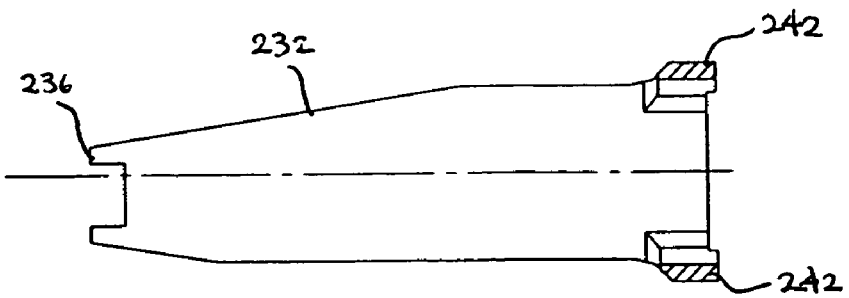
FIGS. 12A to 12C show top, cross-sectional side, and perspective views, respectively, of one variation of a yoke member.
Figure 12A:
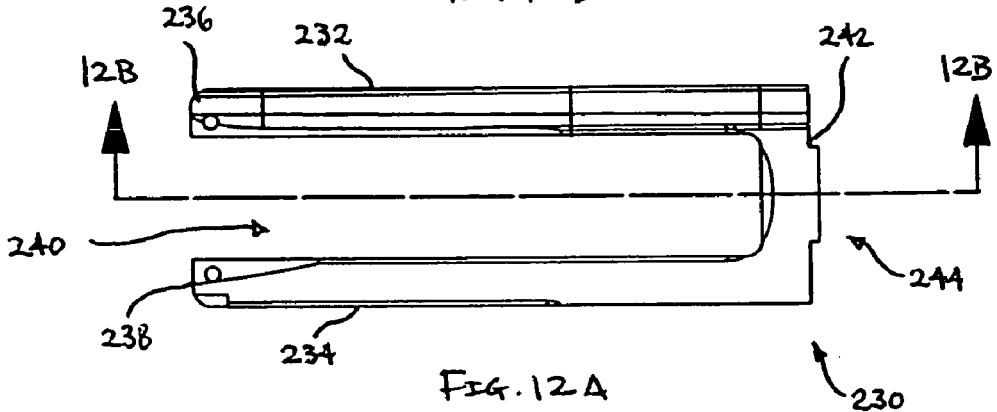
Figure 12C:
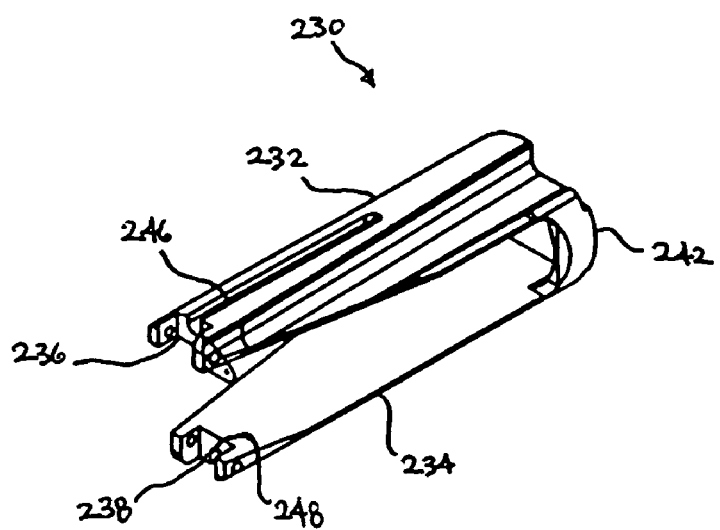

A yoke member may be positioned at the terminal end of working body 28 for holding and maintaining pod assembly 16. FIGS. 12A to 12C show top, cross-sectional side, and perspective views, respectively, of yoke 230. Generally, yoke 230 may be comprised of first arm member 232 and second arm member 234 extending in parallel to one another from a base member 242, which may be attached via proximal surface 244 to end link 210 of working body 28. Yoke 230 may terminate at each arm member 232, 234 in first and second pivot regions 236, 238, respectively, about which the pod assembly 16 may be manipulated. First and second arm members 232, 234 may further extend longitudinally with an overall length of about, e.g., 2 in. (about 5 cm), to create open region 240 between the arm members 232, 234. First and second arm members 232, 234 may also be tapered along their lengths to facilitate insertion of yoke 230 within a tissue region. The opposing sides of each arm member 232, 234, which in part defines open region 240, may be parallel to one another and are spaced apart, e.g., at 0.40 in. (about 1.0 cm), to provide clearance for stapler assembly 42 to be advanced therethrough. Furthermore, the open sides of region 240 may provide adequate clearance for stapler assembly 42 to be opened for advancement over tissue to be affixed while arm members 232, 234 help to maintain the orientation of stapler assembly 42 relative to yoke 230 and working body 28.

Figure 12E:
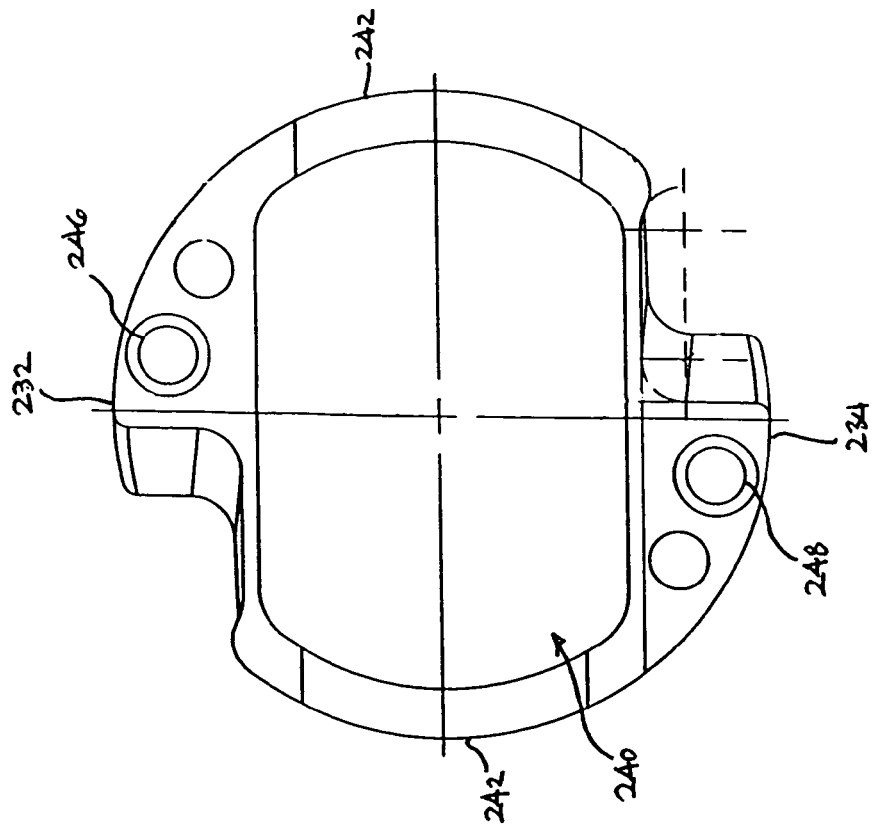
FIGS. 12D and 12E show front and rear end views, respectively, of the yoke member of FIGS. 12A to 12C.
Figure 12D:
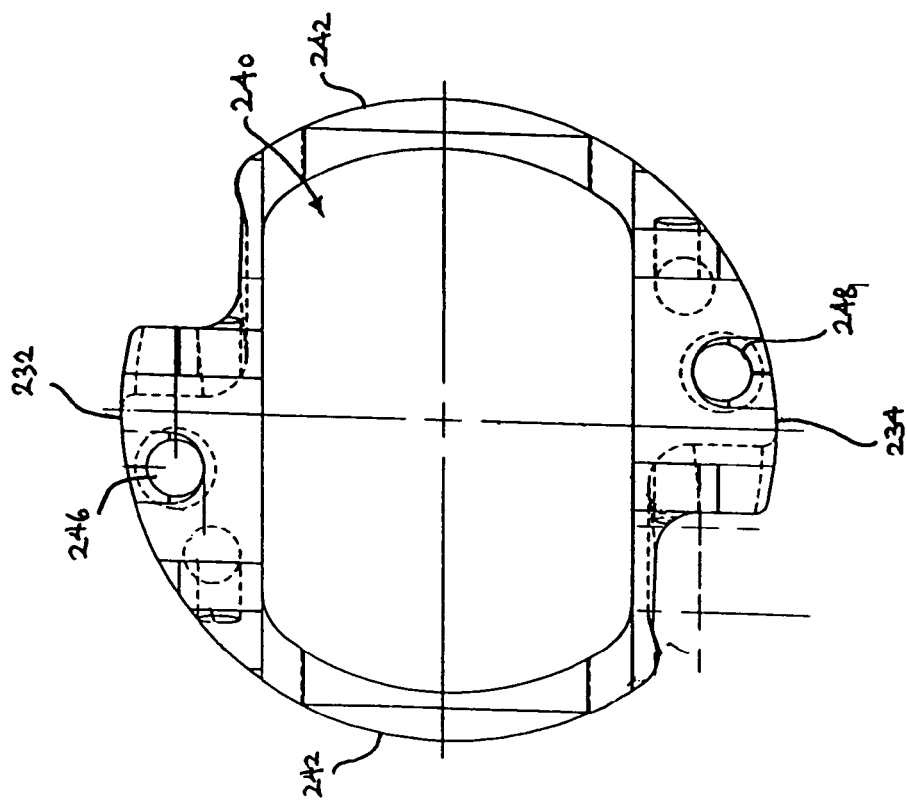

The actuation rods for manipulating pod assembly 16 may extend through yoke 230 via first and second actuation rod channels 246, 248, which may be seen in the perspective view of yoke 230 in FIG. 12C. A portion of actuation rod channels 246, 248 may be slotted or grooved and open along an outer surface of each of arm members 232, 234 to allow actuation rods to extend past the outer surface during pod manipulation. FIGS. 12D and 12E show front and rear end views, respectively, of yoke 230 to provide a detail view of actuation rod channels 246, 248 and open region 240.

Figure 13A:
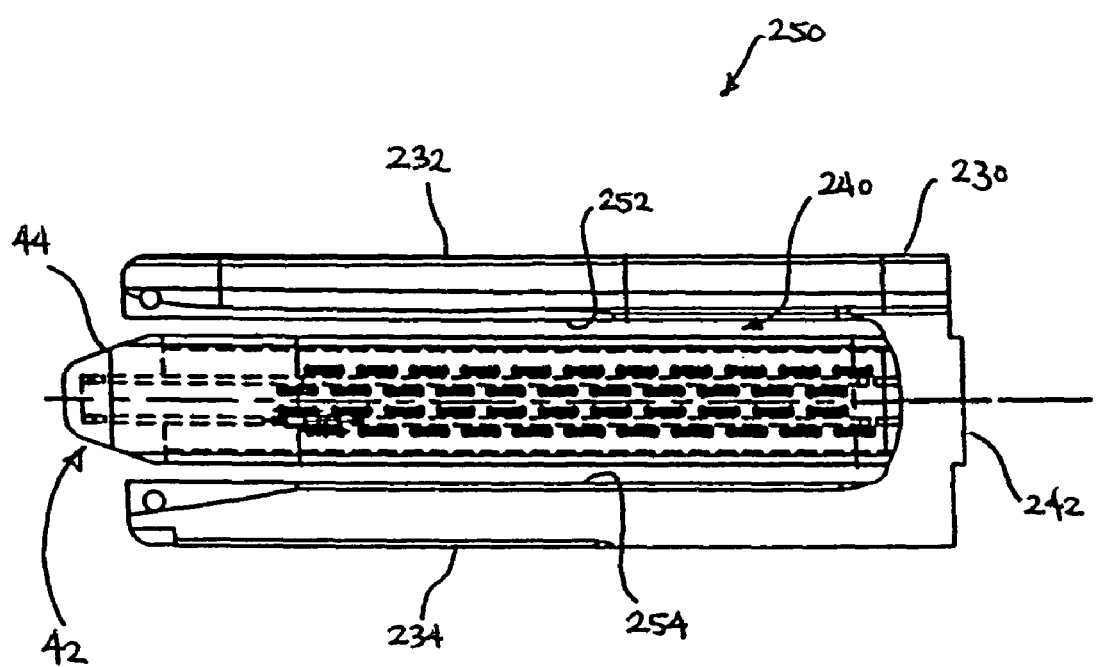
FIG. 13A shows a top view of a stapler cartridge assembly positioned between the arm members of the yoke.
Figure 13B:
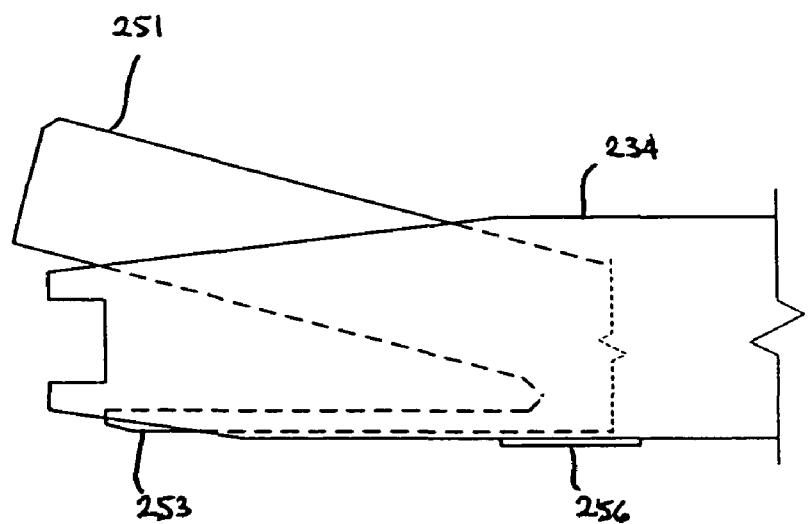
FIGS. 13B and 13C show variations of the stapler assembly positioned between the yoke having varied open regions.
Figure 13C:
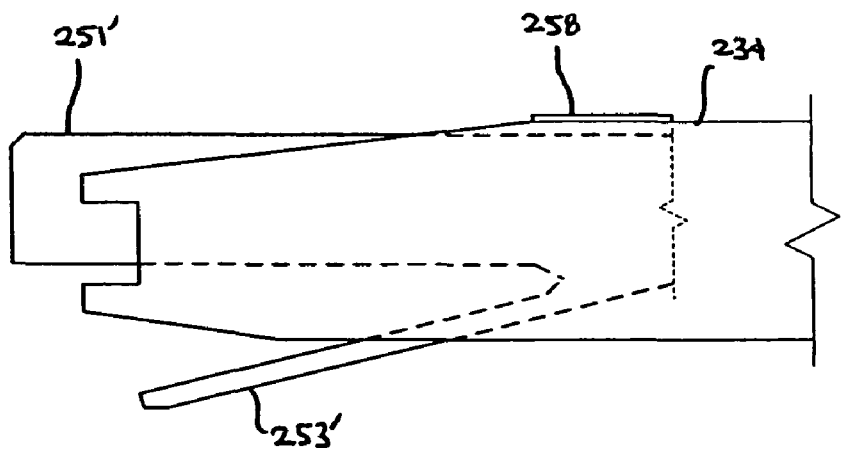

As mentioned above and as shown in the top view of stapler cartridge/yoke assembly 250 in FIG. 13A, each arm member 232, 234 may be parallel to one another and spaced apart to provide clearance for stapler assembly 42 to be advanced therethrough. The arm members 232, 234 may function as guide surfaces 252, 254, respectively, to maintain stapler assembly 42 oriented in a predetermined configuration relative to yoke 230. Furthermore, open region 240 may provide adequate clearance for stapler assembly 42 to be opened prior to advancement over tissue while guide surfaces 252, 254 help to maintain the orientation of stapler assembly 42 relative to yoke 230 and working body 28. Additionally, as shown in FIG. 13A, clearance slots (open region 240) may function to provide clearance for an endoscope or other tool, that can be inserted and advanced or retroflexed to view the working device, as shown below in further detail. To assist in alignment of the stapler assembly 42 to the target tissue, it may be desirable to vary the length of the open region 240. As further shown in FIG. 13B, open region 240 may be configured with a stop, cover, or extension 256 located adjacent to anvil 253 to constrain any transverse or lateral movement of anvil 253 while facilitating movement of cartridge assembly 251. Alternatively, if anvil 253' is configured to move, stop or extension 258 may be configured adjacent to cartridge assembly 251' to constrain any transverse or lateral movement of cartridge assembly 251' while facilitating movement of anvil 253', as shown in FIG. 13C.

Figure 14A:
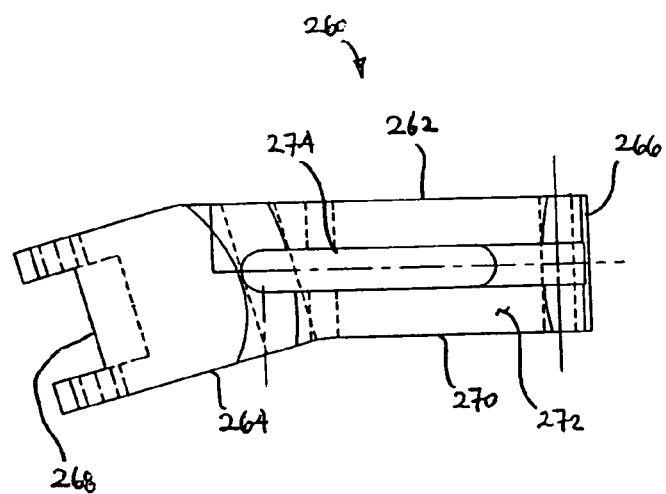
FIGS. 14A to 14C show top, end, and side views, respectively, of an alternative angled hinge member for use with a pod member.
Figure 14B:
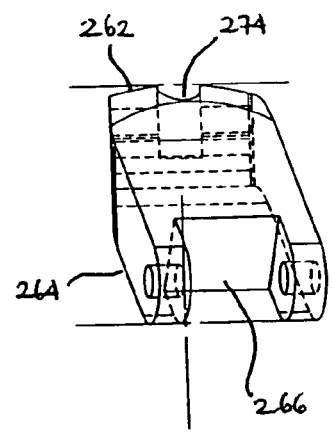
Figure 14C:
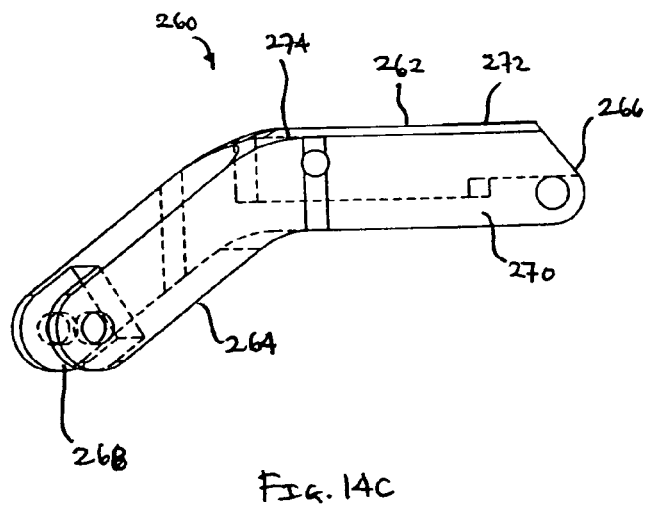

From the distal end of each arm member 232, 234 of yoke member 230, a hinge member may be connected pivotally and extend distally where it may be again pivotally connected to a pod member. An alternative angled hinge member 260 may be seen in FIGS. 14A to 14C, which show top, end, and side views, respectively. Angled hinge 260 may have a proximal portion 262 connected to a distal portion 264, which may be angled with respect to either or both side surface 270 and top surface 272 of proximal portion 262. A yoke-hinge pivot 266 may be defined at a proximal end of proximal portion 262 for pivotal connection to first pivot 236 located on yoke 230. Similarly, a hinge-pod pivot 268 may be defined at a distal end of distal portion 264 for pivotal connection to a pod member. Additionally, actuator rod channel 274 may be optionally defined along at least a portion of proximal portion 262 to provide a opening or space for placement of an actuator rod. A second hinge member, which may mirror the configuration of angled hinge 260, may be configured for connection to second hinge 238 of yoke 230 for connection to a second pod member. Moreover, angled hinge member 260 may be made from any variety of metals or thermoplastics, as described above.

Figure 15A:
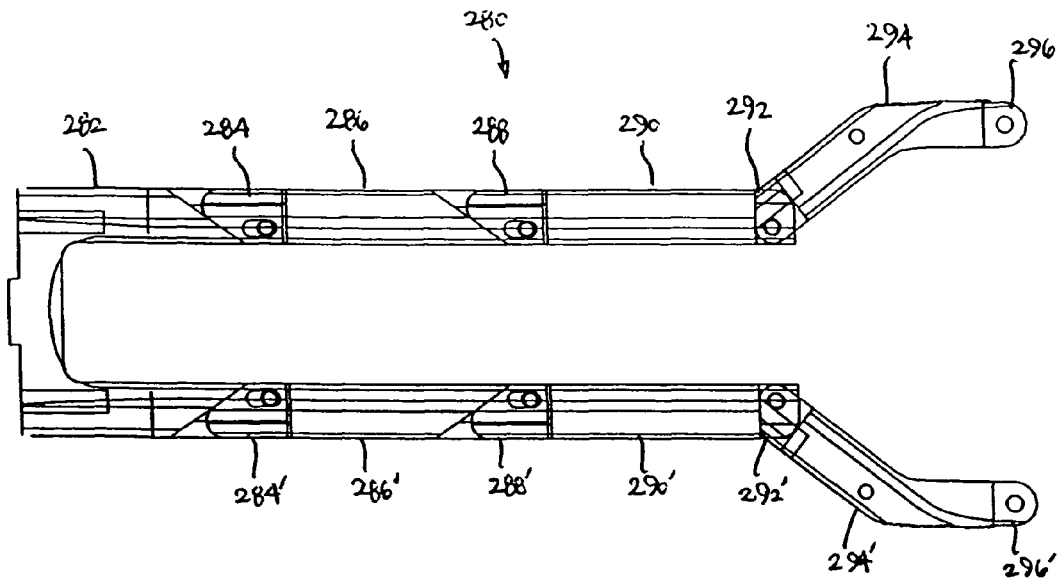
FIGS. 15A to 15C show top and perspective views, respectively, of a variation of a yoke and hinge assembly.
Figure 15B:
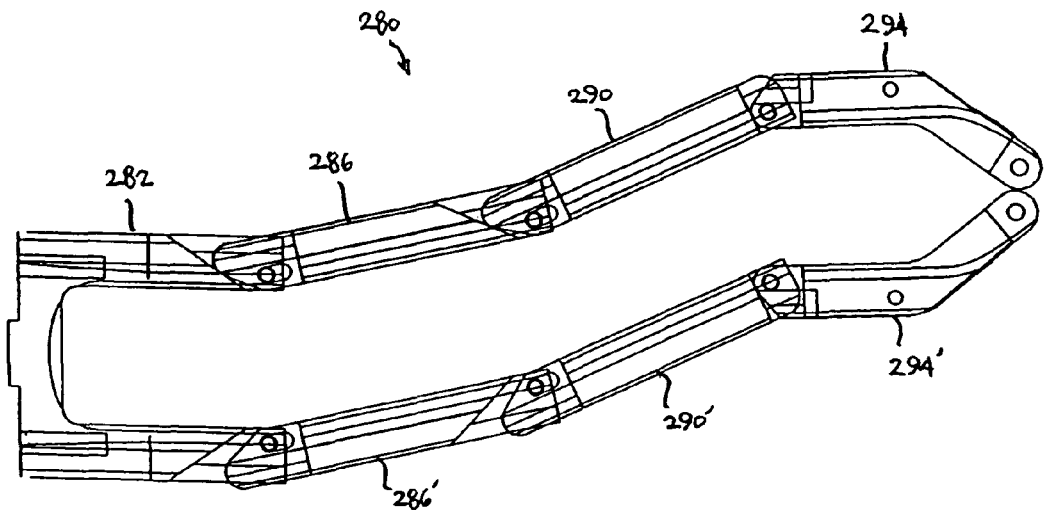

Alternatively, a variation of a yoke/hinge assembly 280 may be utilized, as shown in the top views of FIGS. 15A and 15B. In this variation, yoke/hinge assembly 280 may be configured to flex via one or several additional pivots along its length. Additional ramp members 286, 286', 290, 290', which may be extension members of yoke 282 having pivoted regions at both proximal and distal ends, may be joined via pivots 284, 284', 288, 288', respectively, to one another to form elongated arms. Hinge members 294, 294' may be connected via pivots 292, 292', respectively, to ramp members 290, 290', respectively, and have pivots 296, 296' located at their distal ends for connection to pod members.

Figure 15C:
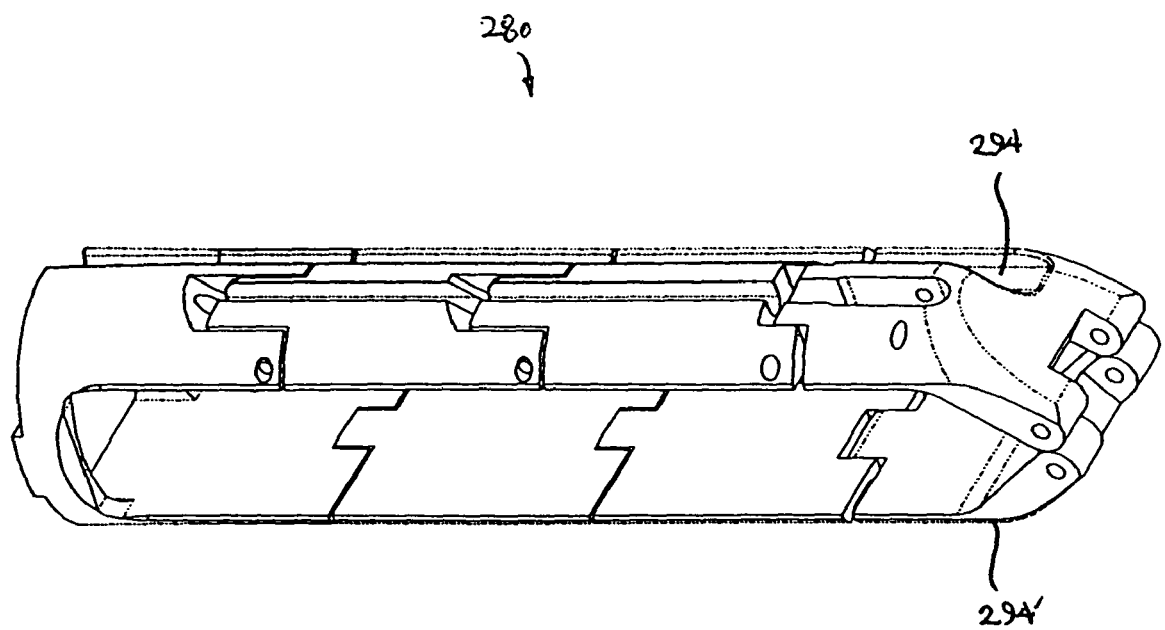

Hinge members 294, 294' may be actuated to an expanded configuration, as shown in FIG. 15A, and yoke/hinge assembly 280 may also be configured to flex via tensioning members (not shown) positioned within a lumen or slot defined along the length of assembly 280 in one or both arms. These tensioning members may be actively manipulated by the user from their proximal ends. Thus, assembly 280 may be flexed to have a bend radius, as shown in the example of FIG. 15B, to allow access to various regions within the hollow body organ as well as to affix various configurations of tissue. Alternatively, assembly 280 may also be passively flexed by contact against tissue or via an external device, such as a mandrel, a gripping tool, or endoscopes configured to flex the assembly 280. FIG. 15C shows an example of a compact configuration of assembly 280 which may be utilized for deployment within a body.

Figure 16A:
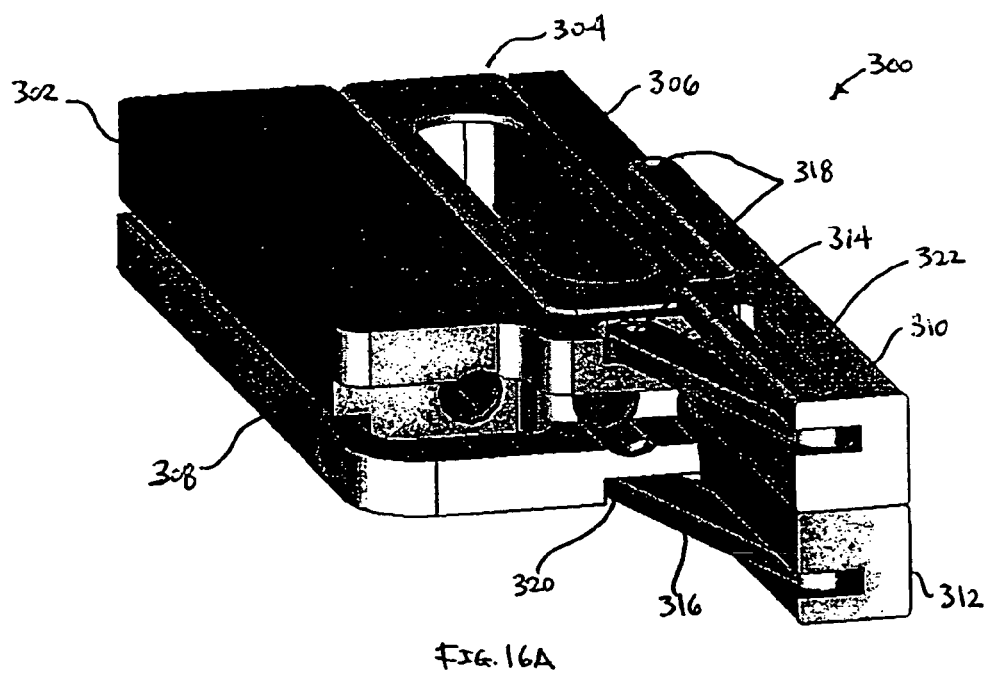
FIGS. 16A to 16C show perspective views of a variation on a hinge device which may be adapted to angle a pod assembly in an offset configuration.
Figure 16B:
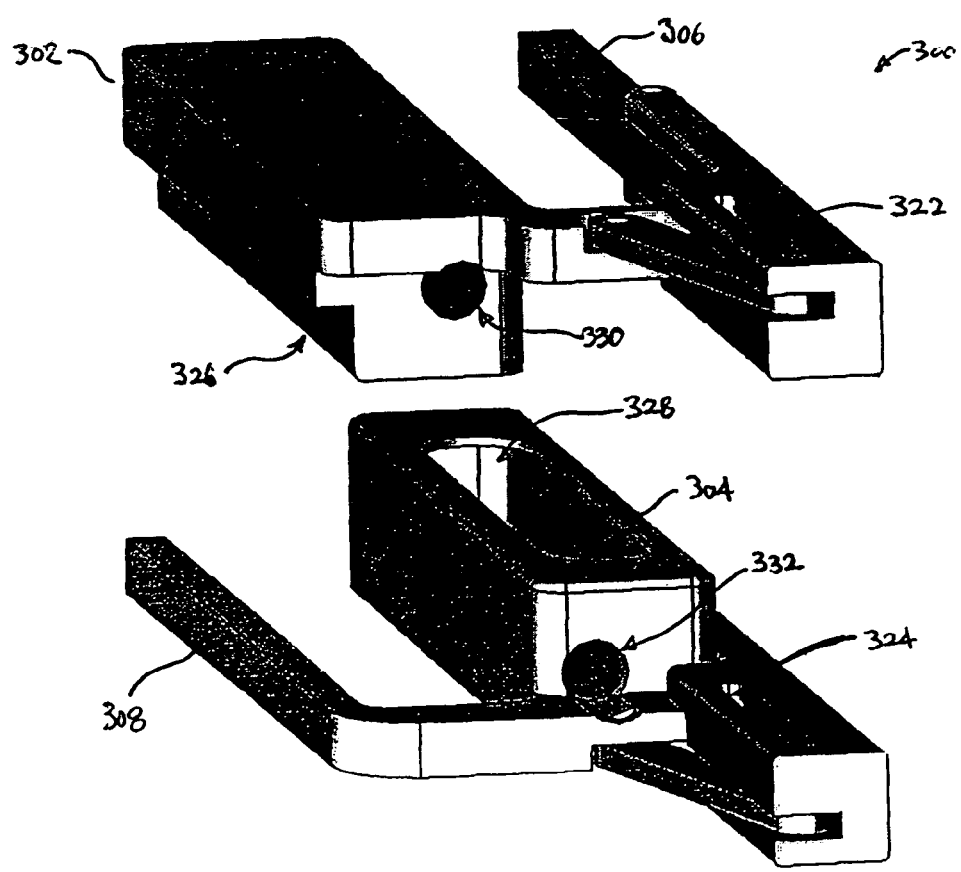
Figure 16C:
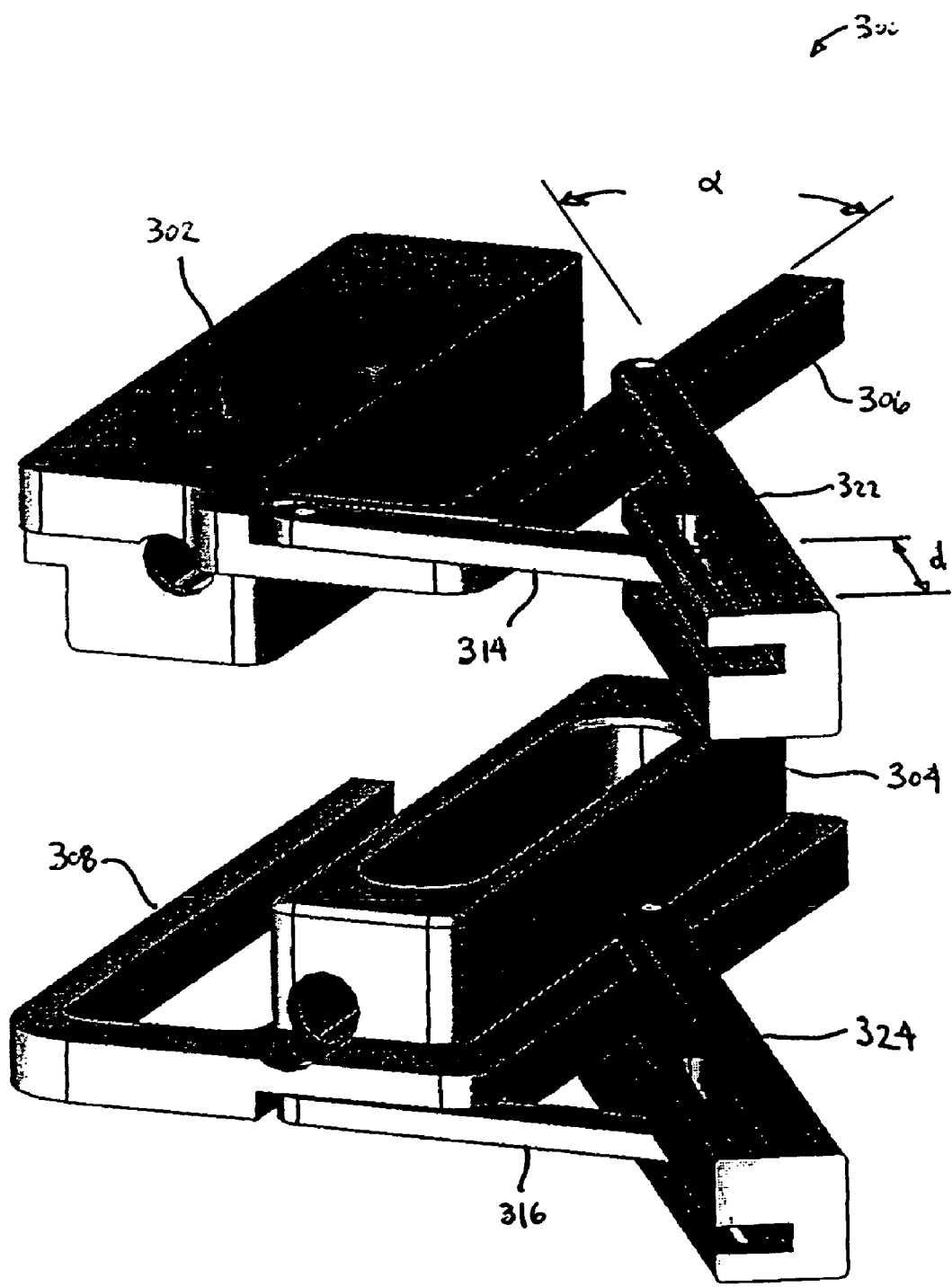

FIGS. 16A to 16C show yet another variation on a hinge device which may be adapted to actively angle the pod assembly in an offset configuration. The working body, as well as vacuum tubes and other features, have been omitted only for the sake of clarity in these views. FIG. 16A shows a perspective view of offset pod assembly 300 in a "straight" configuration where first pod member 302 and second pod member 304 are in a compact or deployment configuration. FIG. 16B shows an example of offset pod assembly 300 in an expanded configuration where first and second pod members 302, 304, respectively, may be actuated to spread apart from one another. First tensioning member or arm 306 may be seen as being part of first pod member 302 and second tensioning member or arm 308 may be seen as being part of second pod member 308.

Offset pod assembly 300 also includes variations on first and second hinge members 310, 312, respectively, which may have respective first and second actuation slots 322, 324 defined longitudinally along a portion of their respective hinge members 310, 312. First actuation linkage 314 may be pivotally connected at its distal end to first pod member 302 and pivotally connected to first hinge member 310 at its proximal end via pivots 318. The proximal end of actuation linkage 314 may also be configured to translate, within first actuation slot 322 when urged. Likewise, second actuation linkage 316 may be pivotally connected at its distal end to second pod member 304 and pivotally connected to second hinge member 312 at its proximal end via pivots 320. Also seen are first and second vacuum openings 326, 328, respectively, for acquiring tissue to be approximated, and first and second vacuum passages 330, 332, respectively.

FIG. 16C shows offset pod assembly 300 having been urged into its offset configuration. As shown, the proximal end of first actuation linkage 314 has been translated distally within first actuation slot 322 and the proximal end of second actuation linkage 316 has also been translated distally within second actuation slot 324. Each linkage 314, 316 may be translated a distance, d, via actuation rods to rotate first and second pod members 302, 304 about their respective pivots such that pod members 302, 304 may be offset at an angle, $\alpha$, relative to a longitudinal axis of the working body. From this offset configuration, tissue may be approximated and affixed at various angles. Alternatively, the pod members 302, 304 may also be configured to be passively flexed by contact against tissue or via an external device, including any of the tools described above. Although both pod members 302, 304 are shown in this illustration as having been offset at similar angles, a single pod member may be alternatively actuated to become offset relative to the other pod member. Furthermore, both pod members may also be offset at various angles depending upon the desired tissue configuration; moreover, each pod member may be also independently offset at its own angle, again depending upon the tissue configuration. These examples are merely intended to be illustrative and are not intended to be limiting.

The pod assembly itself may be seen in greater detail in the perspective view of FIG. 17A. As shown, the pod member may have an elongated vacuum chamber 340. A top cover and an optional basket insert have been removed for clarity. The vacuum chamber 340 may be in fluid communication via vacuum tubes 200 which may be connected to a vacuum pump (not shown) at its proximal end and to vacuum chamber 340 at its distal end. Tensioning member or arm 342 may extend longitudinally adjacent to vacuum chamber 340 while forming a gap between the two through which the tissue may be drawn. The tensioning member 342 may extend along the entire length of the pod member and beyond or it may extend just partially. Alternatively, in other variations, tensioning member 342 may be omitted entirely. In either case, a distal tip of the tensioning member 342 is preferably configured to be atraumatic, e.g., blunted, rounded, or it may have a separate soft tip attached and/or may be shaped or made of a material to conform to the distal esophagus and/or proximal stomach to allow ease of insertion and lessen trauma once in place.

A pivot 344 may be configured at the proximal end of the pod member for attachment to a hinge member. The distal end of the pod member may also have a tapered flexible tip 346 attached thereto. This tip 346 may be configured to have an atraumatic tip 354 to facilitate deployment of the device with minimal damage to the tissue. Flexible tip 346 may be made from any variety of biocompatible polymers and elastomers. Flexible tip 346 may also define a guidewire lumen 348 extending from a distal guidewire opening 350 at atraumatic tip 354 to proximal guidewire opening 352 located proximally on flexible tip 346. As mentioned above, a guidewire may optionally be used to guide the pod members during initial deployment and positioning within the hollow body organ in a manner similar to a rapid-exchange (RX) type catheter. Accordingly, an optional guidewire may be passed through guidewire lumen 348 and subsequently removed, if desired. A flat mating surface 356 may also be defined along the side of flexible tip 346 to allow for a compact configuration when the second pod member is positioned adjacently. Tip 354 may be optionally formed of a radio-opaque material or imbued with radio-opaque capabilities.

Figure 17B:
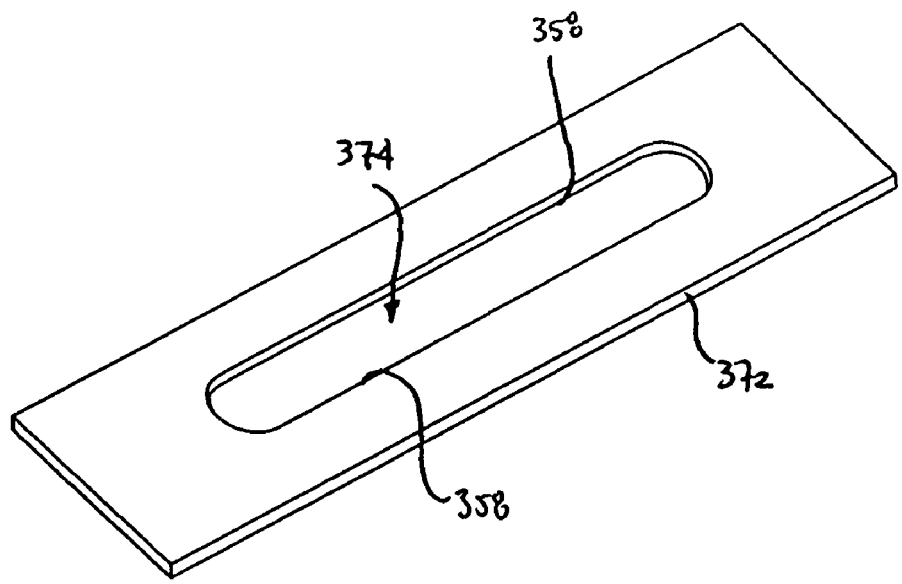
FIG. 17B shows a perspective view of one variation of a top cover which may be used with the pod assembly.

A top cover 372 which defines opening 374, as shown in FIG. 17B, may be secured over vacuum chamber 340. An undercut 358 may be defined around opening 374 to help aid in mechanically adhering any tissue which may be drawn into opening 374. Opening 374 is shown as being slotted; however, it may be formed into an elliptical shape or various other shapes so long as an adequate opening is available for adhering a sufficient amount of tissue therewithin or thereto. Alternatively, rather than a single opening 374, multiple smaller openings may be defined over top cover 372 so long as an adequate area is available for adhering tissue thereto. An optional mesh-like insert may be positioned within vacuum chamber 340 to help prevent the vacuum chamber from becoming clogged by tissue.

Turning to FIGS. 18A to 18D, an optional basket insert 360 is shown in side, end, bottom, and perspective views, respectively. Basket insert 360 may be placed within vacuum chamber 340 to provide for an optimized mesh surface through which a vacuum force may be applied to the tissue. Overall dimensions of basket insert 360 may vary so long as it may be securely positioned within vacuum chamber 340. An example of insert 360 dimensions is 1.3 in. (about 3.3 cm) in length and 0.3 in. (about 0.8 cm) in width. Basket insert 360 may also be made from a variety of materials, e.g., stainless steel, provided that the tensile strength is sufficient to withstand the various forces generated.

Figure 17C:
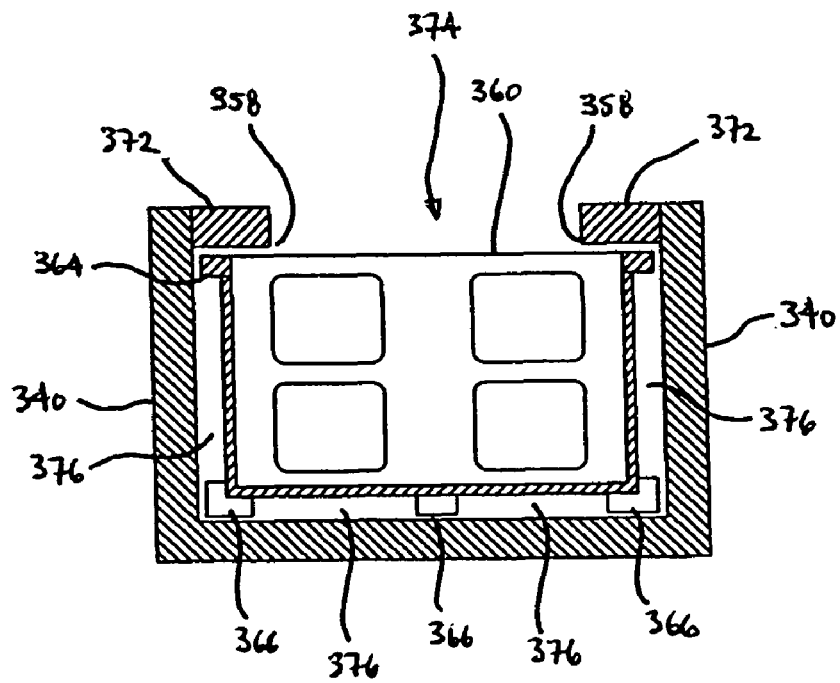
FIG. 17C shows a cross-sectional view of an optional basket insert positioned within a vacuum chamber and a top cover secured over the chamber.

Basket insert 360 may have basket walls 362 forming a mesh-like vacuum chamber 370 with flange 364 surrounding the edges of one open side of insert 360. Each of the basket walls 362 may define a plurality of openings therethrough and the bottom surface of basket walls 362 may also define a plurality of supports 366 positioned in-between openings 368. These supports 366 may be configured to space each of the basket walls 362 away from the walls of vacuum chamber 340, as shown in FIG. 17C, which shows a cross-sectional view of basket insert 360 positioned within vacuum chamber 340 and top cover 372 placed over the chamber 340. Plenum 376 may thus be defined around the entire basket insert 360, or a portion thereof, between basket walls 362 and vacuum chamber 340 via the spacing provided by supports 366 and flange 364. The open plenum 376 allows a vacuum force to be applied to the tissue while preventing the tissue from clogging the vacuum chamber 340.

Alternatively, rather than utilizing a separate basket insert 360 for placement within vacuum chamber 340, the interior surface of vacuum chamber 340 may be textured, channeled, labyrinthed, or interdigitated to increase the surface area for vacuum adherence in the same manner as basket insert 360. Moreover, mechanical tines or teeth may be formed within basket insert 360 or within vacuum chamber 340 to facilitate additional mechanical adherence of tissue within the pod member. Another alternative may utilize a snare-like wire or member positioned within vacuum chamber 340 around opening 374. In such a variation, once tissue has been drawn through opening 374, the snare may be drawn tightly around the adhered tissue.

Figure 17D:
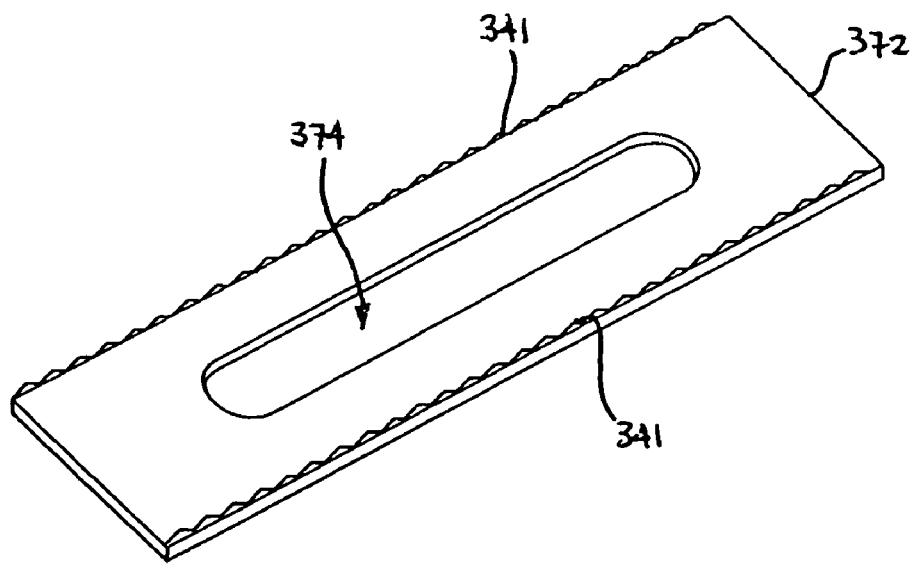
FIGS. 17D and 17E show another variation of FIGS. 17B and 17C, respectively, where the top cover and/or pod member may have serrations.
Figure 17E:
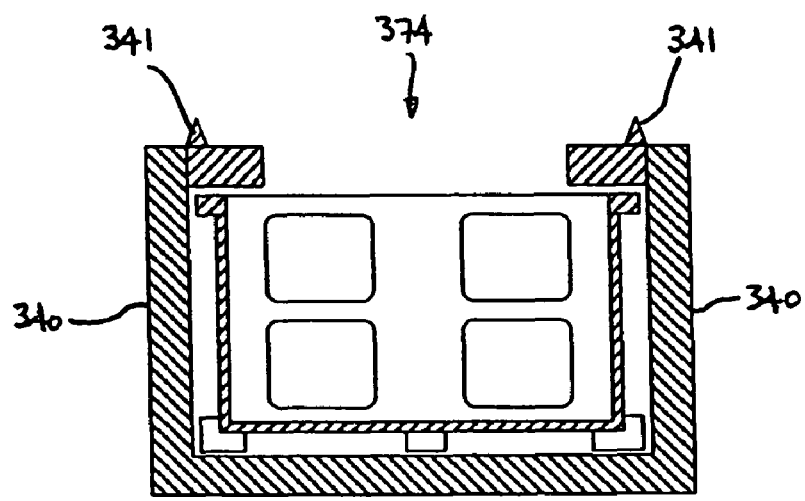
Figure 18A:
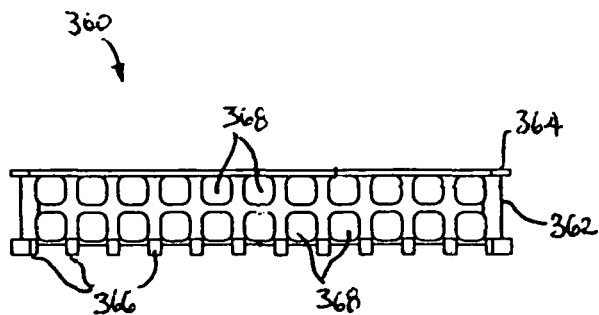
FIGS. 18A to 18D show side, end, bottom, and perspective views, respectively, of an optional basket insert which may be placed within the vacuum chamber of the pod assembly.
Figure 18B:
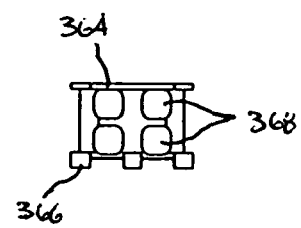
Figure 18C:
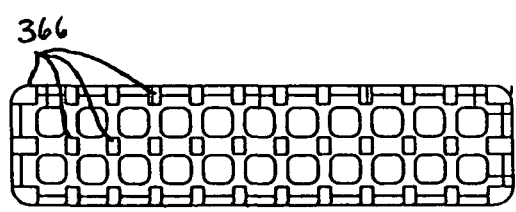
Figure 18D:
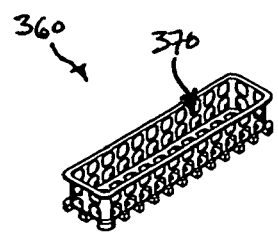

Moreover, one or both pod members may also incorporate a number of other methods to facilitate tissue movement and/or adherence to the respective pod member. For instance, FIGS. 17D and 17E show the top cover 372 and cross-sectional view of basket insert 360, respectively, of FIGS. 17B and 17C with the addition of serrations 341. These serrations 341 are shown as being defined along a length of cover 372; however, they may alternatively be defined around the opening 374 or in a number of various other configurations depending upon the desired results. Furthermore, serrations 341 are illustrated as protrusions but any variations or configurations of serrations 341 may also be utilized in other variations of the device.

Figure 19C:
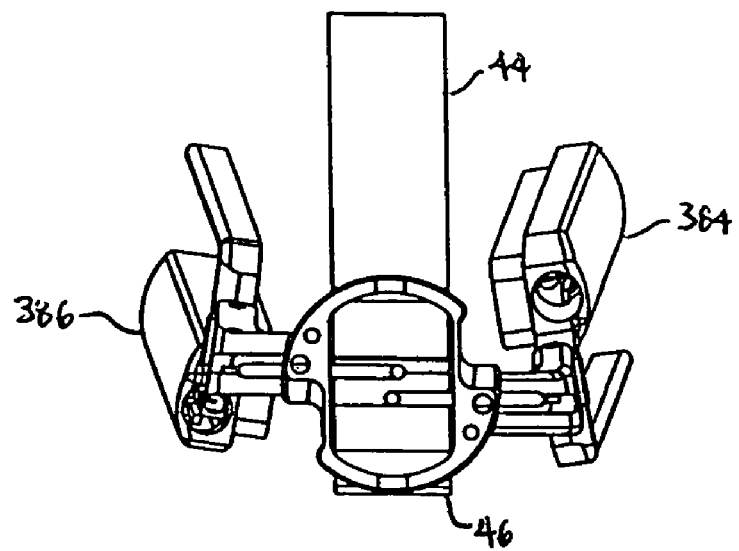
FIGS. 19C and 19D show rear and front views, respectively, of the pod members and the staple assembly of FIGS. 19A and 19B.
Figure 19D:
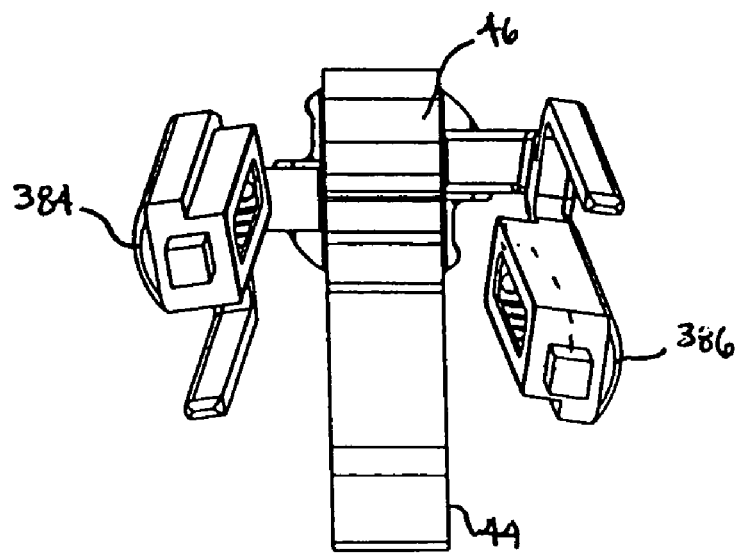

FIGS. 19A and 19B show another variation of the pod assembly where angled pod assembly 380 may be mounted on a distal end of working body 382. As shown, first and second pod members 384, 386, respectively, may be configured to extend angularly via angled hinges 260. Also shown are vacuum tubes 388 extending between pod members 384, 386 and working body 382. The figures also show the positioning of staple cartridge 44 and anvil 46 opened for clamping onto folded tissue, which is not shown for clarity. FIGS. 19C and 19D show rear and front views of pod members 384, 386 and staple cartridge 44 and anvil 46.

Fixation Assembly

Figure 20A:
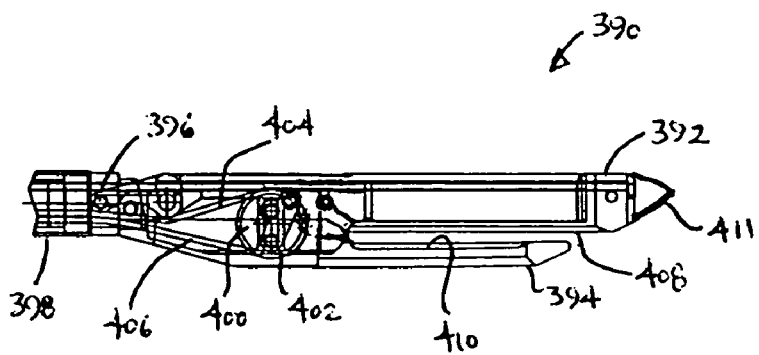
FIGS. 20A and 20B show side views of a variation of the stapler assembly in clamped and opened configurations, respectively.
Figure 21A:
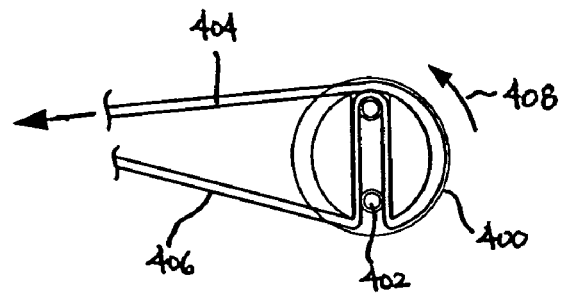
FIGS. 21A and 21B show side views of a variation of a cam member which may be used to urge the stapler assembly open and close.
Figure 20B:
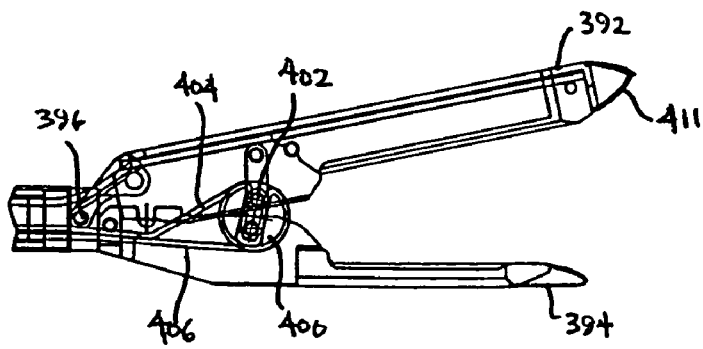
Figure 21B:
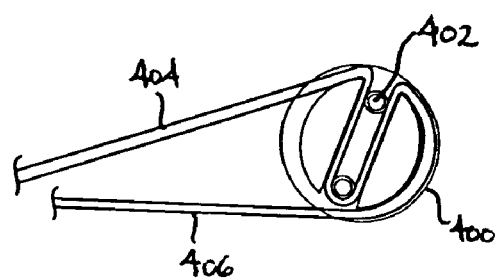

The fixation assembly, as mentioned above, may be delivered through the main lumen of the folder assembly for deployment over tissue which has been approximated into a folded configuration. One variation of a stapler which may be used with the folder assembly described herein is described in detail in U.S. Pat. No. 4,610,383 (Rothfuss et al.), which is incorporated herein by reference in its entirety. Another variation of a stapler assembly 390, which is positioned at the distal end of the fixation assembly, is shown in side views in FIGS. 20A and 20B. Generally, stapler cartridge 392 may be pivotally connected via pivot 396 to the end of flexible shaft 398. Anvil 394 may be configured to remain stationary relative to flexible shaft 398 while stapler cartridge 392 may be manipulatable into an open and closed configuration with respect to flexible shaft 398 and anvil 394. As seen, stapler cartridge 392 and/or anvil 394 may optionally incorporate a tapered end 411 positioned at a distal end of either cartridge 392, anvil 394, or both. Tapered end 411 may be fabricated of any of the polymers or other materials described herein and is preferably atraumatic to facilitate dilation or insertion past tissue. To manipulate stapler cartridge 392 to open and close, a circular or disk-shaped cam 400 may be pivotally attached about rotational pivot 402 located on the side of the proximal end of stapler cartridge 392. As seen in the detail view of cam 400 in FIG. 21A, actuation wires or cables 404, 406 may be wound about cam 400 such that when cable 404 is pulled, cam 400 is urged to rotate about rotational pivot 402 in the direction of arrow 408. Actuation cables 404, 406 may be manipulated from their proximal ends by the user. As cam 400 is rotated in direction 408, a portion of anvil 394 may be engaged by cam 400 thereby forcing stapler cartridge 392 to pivot into an open configuration, as shown in FIG. 20B, when cam 400 is fully rotated, as in FIG. 211B. Cam 400 may be made into other shapes, e.g., oval, elliptical, etc., depending upon the desired design characteristics. One cam 400 may be utilized, as shown; however, an additional cam may also be affixed on the opposite side of stapler cartridge 392 such that dual cams are configured to open and close simultaneously in parallel. Alternatively, in the same device, the location of stapler cartridge 392 and anvil 394 may be reversed (e.g. anvil 394 may be configured to move toward cartridge 392) depending on the location of the desired target and clearance desired.

Detail views of the stapler assembly is shown in FIGS. 22A to 22D. FIGS. 22A to 22C show cross-sectional side, front, and top views, respectively, of stapler assembly 410. Cartridge housing 412 generally houses a plurality of staples 414 which may be aligned adjacently to one another in one or more rows. The distal ends of both cartridge housing 412 and anvil 422 may be configured to be atraumatic, e.g., blunted, rounded, etc., to the tissue to be affixed. Moreover, cartridge housing 412 and anvil 422 may be configured such that their cross-sectional shape is keyed to the main lumen of the folder assembly so that the orientation of the cartridge housing 412 is maintained relative to the folder assembly, as described above.

FIG. 22C shows a top view of cartridge housing 412 wherein four rows of staples 414 may be aligned. Other variations of cartridge housing 412 may utilize fewer or greater than four rows of staples 414. To deploy staples 414 from cartridge housing 412, two wedges 416, 416', which may be offset or staggered from one another, may each be pulled proximally through cartridge housing 412 via staple actuation wire 420. Wedges 416, 416' may be adjacently positioned to one another but are preferably staggered such that the staples are deployed in a sequenced deployment order. Staple actuation wire 420 may be manipulated via its proximal end by the user when staples 414 are to be deployed out of cartridge housing 412 into the tissue.

Staples 414 may be deployed through staple apertures 418 defined over the surface of cartridge housing 412 in apposition to staple closure surface 424 of anvil 422. As the staggered wedges 416, 416' are pulled proximally, each wedge 416, 416' may engage one or more rows of staples and urge them through staple apertures 418, as shown in FIG. 22A, and through the tissue until they are engaged in corresponding staple detents 426, as shown in FIG. 22D. As further shown in FIG. 22D, which shows a top view of staple closure surface 424 of anvil 422, each staple detent 426 preferably corresponds to the distal ends of each staple 414.

Figure 22E:
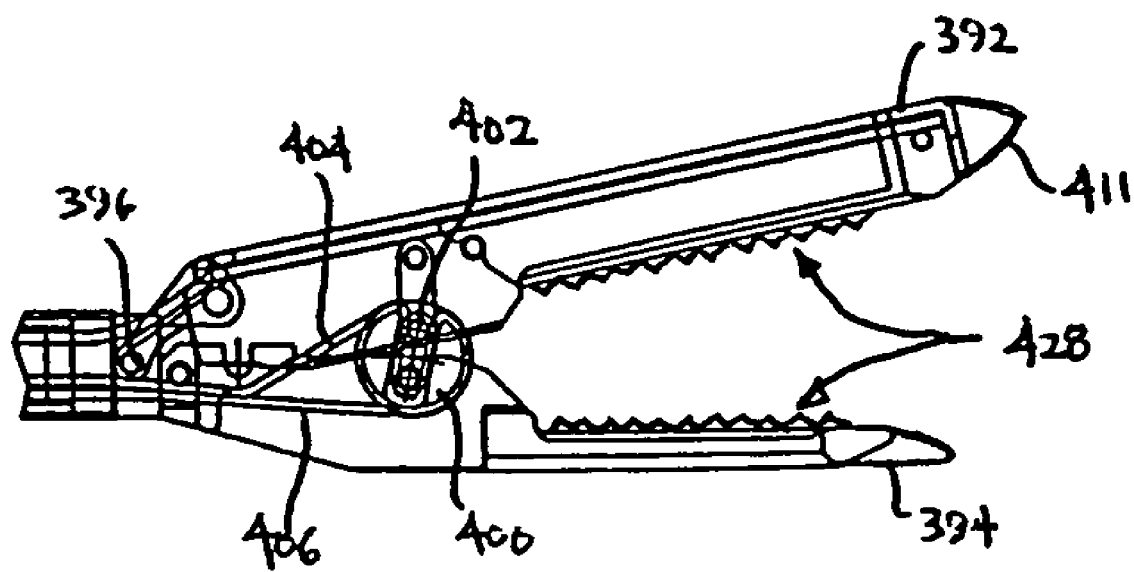
FIG. 22E shows a side view of another variation of a stapler assembly having serrations defined along its clamping surfaces.

As described above, cartridge housing 412 and/or anvil 422 may be configured to be atraumatic, e.g., blunted, rounded, etc.; however, it may be desirable to serrate or otherwise roughen the outside edges of both or either the cartridge 412 and/or anvil 422 to ensure full tissue capture upon clamping of the two surfaces. A variation of the stapler assembly 410 is shown in FIG. 22E, which shows serrations 428 defined along the lengths of cartridge 412 and anvil 422. Serrations 428 may be optionally defined along only one of cartridge 412 or anvil 422 and it may also be defined only partially along the length. Alternatively, other projections or protrusions, such as spears, may be utilized. In yet another alternative, rather than utilizing projections or serrations 428, the surfaces of cartridge 412 and/or anvil 422 in contact with the tissue may simply be roughened or sharpened to facilitate serrating or roughening the contacted tissue or may employ absorptive materials in the form of pads, coatings or covers to facilitate traction. Such pads, covers or coatings may be formed of cotton, Goretex®, polyester, Velcro, etc., and may remain on the surface of the cartridge once staples are delivery, or alternatively may be transmitted with the staples to remain with the tissue affixed thereby.

Figure 23A:
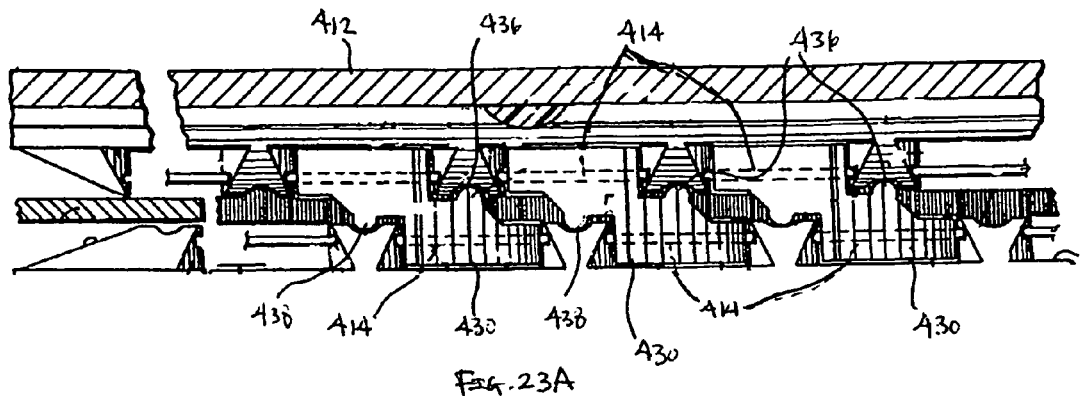
FIG. 23A shows a top view of one variation of staple pushers positioned over corresponding staples.
Figure 23B:
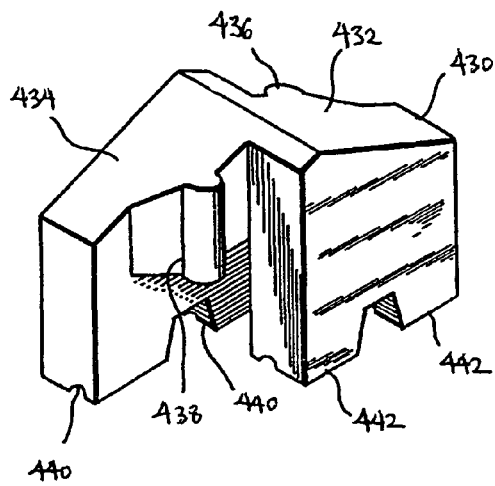
FIG. 23B shows a detailed perspective view of one example of a staple pusher.
Figure 23C:
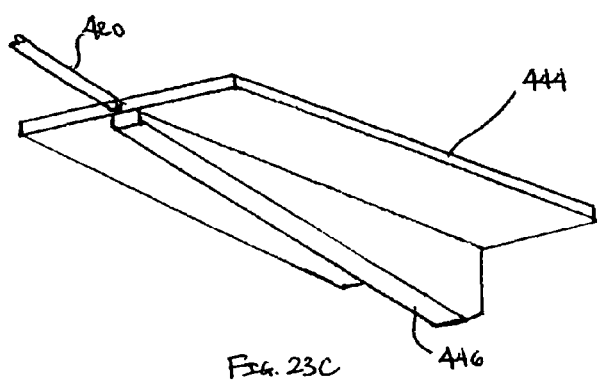
FIG. 23C shows a perspective view of one example of a wedge which may be configured to slide within the cartridge housing.

To facilitate the deployment of the staples 414 as wedges 416, 416' are urged through cartridge housing 412, staple pushers 430 may be utilized. As shown in FIG. 23A, which is a top view of one variation of staple pushers 430 positioned over corresponding staples 414, a single staple pusher 430 may be configured to engage two staples 414 in adjacent rows. When a wedge contacts a staple pusher 430, two adjacent staples 414 may be fired sequentially. FIG. 23B shows a detailed perspective view of one example of a staple pusher 430. In this variation, staple pusher 430 may be comprised of one or more sloped cam surfaces 432, 434 for slidingly engaging a wedge. As a wedge engages a cam surface, it may push staple pusher 430 down towards staples 414 as pusher 430 is guided via one or more guides 436, 438. Staple pusher 430 may then engage a first staple via staple engagement surface 440 and a second staple via staple engagement surface 442. An example of a wedge 446 which may be configured to slide within cartridge housing 412 is shown in the perspective view of wedge platform 444 in FIG. 23C. Although a single wedge 446 is shown in the figure extending from platform 444, two offset wedges may be configured into a single platform or two individual wedges may be utilized adjacent and offset to one another.

Figure 24A:
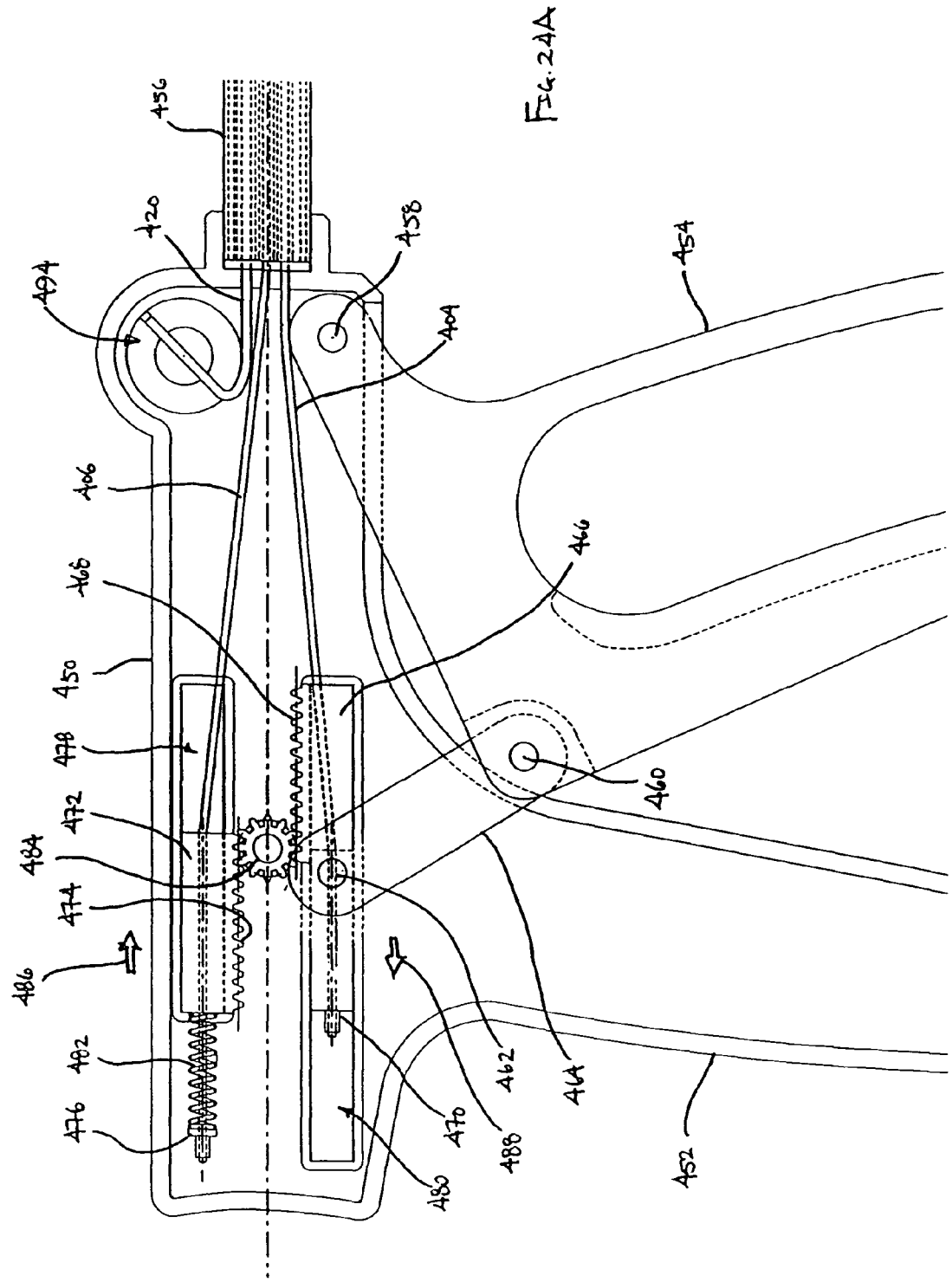
FIGS. 24A and 24B show cross-sectional side views of one variation of a stapler handle and its associated controls.

As mentioned above, cartridge housing 412 may be manipulated into an open and closed position for clamping over the tissue. To control the closure of cartridge housing 412 against anvil 422, a stapler control handle may be used, as shown in the cross-sectional views of the stapler control in FIGS. 24A and 24B. FIG. 24A shows stapler handle housing 450 which may house the tensioning and releasing mechanism for opening and closing cartridge housing 412 relative to anvil 422. Grip 452 may be provided for the user to grasp while manipulating the device during insertion and deployment as well as to help articulate actuation handle 454 for opening and/or closing cartridge housing 412. Actuation handle 454 may be pivotally connected to housing 450 via pivot 458 and to actuation linkage 464 via handle pivot 460. When actuation handle 454 is pulled towards grip 452, handle 44 may rotate about pivot 458 and urge actuation linkage 464 to rotate about handle pivot 460. The opposite end of actuation linkage 464 may be rotatingly connected via pivot 462 to a translating slide block 466 contained within housing 450. Alternatively, it may be desirable to configure the fixation assembly with the staple jaws preferentially biased in an open position by placing tension on actuation cable 404 with a spring placed in device handle (not shown). Upon insertion of the staple jaws into the main lumen, the jaws may be retained in a closed position by the inner diameter of the main lumen. Upon reaching the yoke portion, the jaws would be adapted to bias open into clearance slots 254 (252) to slide onto either side of presented tissue. Once the fixation has occurred, the jaws of the fixation assembly may be directed to a closed position by the yoke, and then the device main lumen as the fixation assembly is withdrawn from the patient.

Slide block 466 may anchor actuation cable 404 thereto via a mechanical anchor 470, e.g., crimps, clamps, adhesives, etc. An upper surface of slide block 466 may comprise rack 468 having a plurality of gear teeth defined thereon. When actuation handle 454 is pulled and actuation linkage 464 is urged proximally, slide block 466 may be forced proximally within travel guide 480, as indicated by arrow 488, to thereby pull actuation cable 404 proximally and thereby force cam 400 to rotate and open the cartridge housing. Simultaneously, while slide block 466 is translated proximally, rack 468 may engage and urge gear 484 to rotate clockwise in the figure, which in turn may force gear 484 to engage and urge rack 474, which is located on a lower surface of complementary slide block 472, to translate distally within travel guide 478, as indicated by arrow 486.

Figure 24B:
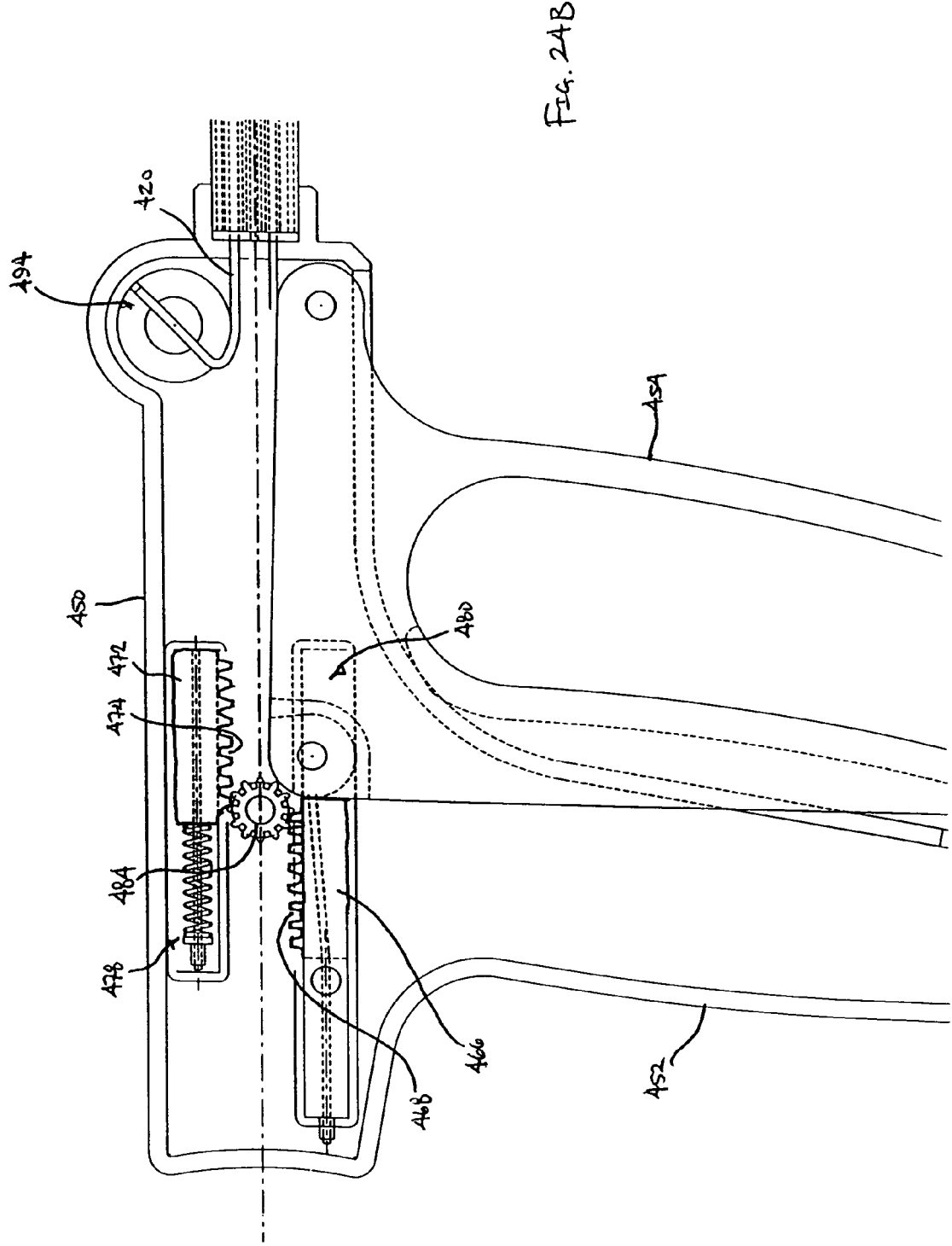

Complementary slide block 472 may anchor actuation cable 406 thereto via anchor 476 in the same or similar manner as anchor 470. Actuation cable 406 may be attached to anchor 476 with a retention spring 482 optionally interposed between anchor 476 and slide block 472 to take up any excess slack in the cable 406. FIG. 24B shows the handle assembly after actuation handle 454 has been actuated and slide blocks 466, 472 have been translated within their respective channels 480, 478 to fully or partially clamp cartridge housing 412 against anvil 422 over the tissue. Once cartridge housing 412 has been clamped over the folded tissue, staple deployment actuator 494 may be rotated or urged to pull staple actuation wires 420 to fire the staples into the tissue. Once staple deployment has been completed, actuation handle 454 may be urged distally to reverse the process described above to open the clamp for removal from the tissue region or for repositioning the staple assembly in another region of the tissue.

The actuation cables 404, 406 as well as staple actuation wires 420 may each be routed through flexible shaft 456, which connects handle 450 to stapler assembly 410. Flexible shaft 456 may be comprised of a tubular member having an outer sheath and an optional inner sheath, either or both of which may be made from any of the polymeric materials described above. The shaft 456 may further utilize braided materials, e.g., superelastic materials such as Nickel-Titanium alloy, integrated throughout to increase column strength and to prevent kinking. Alternatively, shaft 456 may be formed of wire (round or square flat configuration) to enhance compressive and/or tensile strength.

In a further variation, although the tissue approximation device 500 may be configured to be flexible, it may also be desirable to actively or passively curve working body 502 to assist in overall placement of the system within the target organ for optimal presentation of tissue overlap 100 prior to placement of the stapler assembly, as shown in the perspective views of FIGS. 25A and 25B. For passive actuation, a curved stylet (not shown) may be placed alongside the actuation rods in the actuation rod channels, or in another available space within the working body 502, to bias the main body 502 in the curvature provided by the stylet. Working body 502 may be optionally configured to have a bending region 504 located proximally of the pod assembly 512. This optional bending region 504 may be configured to facilitate bending of a portion of the working body 502 in any number of directions or only in a specified direction, depending upon the desired results.

In addition, as depicted in the detail view of FIG. 25C, a distal position control 507 may be adapted to fit onto working body 502 via a connector tube 514. Distal position control 507 may be further adapted to be integrated into handle 34 (as shown in FIG. 1). Distal position control 507 may comprise a base 506, a lever 508 configured to rotate about pivot 510 located on base 506, a linkage mechanism 516, an adjustment assembly 518, and a curvature linkage 519. An optional cap or seal 517 may be placed over a proximal end of the base 506 to seal or cover an opening to the main lumen of the working body. In operation, lever 508 may be pivotally mounted to base 506 via linkage mechanism 516. Depending on the amount of curvature desired in bending region 504, adjustment assembly 518 can be adjusted, e.g., by rotating the mechanism to adjust tension curvature linkage 519 prior to actuation of lever 508. FIG. 25A depicts the assembly 500 in the non-deployed, i.e., a straightened position of working body 502, while FIG. 25B depicts full actuation of lever 508 to impart a curvature to the distal end of working body 28. The curvature of bending region 504 may accordingly be adjusted to any intermediate position depending upon the degree of actuation of lever 508. Furthermore, although the degree of bending of the distal portion of the assembly 500 relative to a longitudinal axis of working body 502 is shown to be about 45° in this example, other variations may be adjusted to have a maximum bend of a lesser or greater degree depending upon the desired bending. Moreover, other variations may allow for bending of the assembly 500 in either a unidirectional manner or in any other direction, again depending upon the desired results. It is further contemplated that the bending region 504 may occur at a variety of locations along the shaft of working body 502, such as in the distal or proximal region of the working body or at any point therebetween.

Figure 25D:
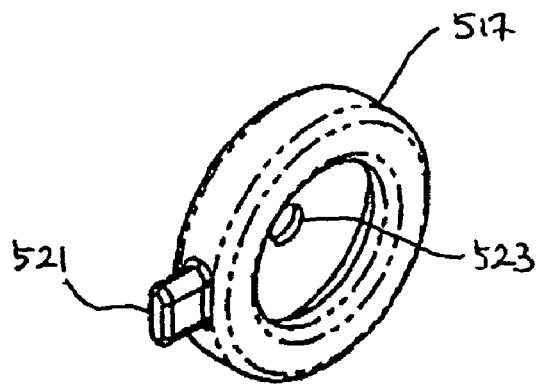
FIGS. 25D and 25E show perspective and end views, respectively, of a variation of an end cap or seal which may be used to cap the handle of FIG. 25C.
Figure 25E:
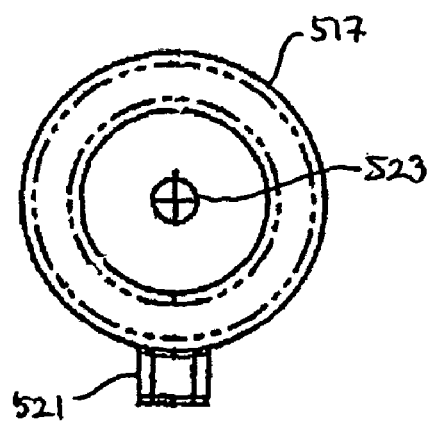

As mentioned above, optional cap or seal 517 may be placed over a proximal end of the base 506 to seal or cover an opening to the main lumen of the working body. FIGS. 25D and 25E show perspective and end views, respectively, of a variation of end cap or seal 517 which may be used to cap the handle of FIG. 25C. End cap 517 may seal the main lumen yet allow passage of devices through the membrane through a small expandable opening 523 covering the main lumen. An optional tab or handle 521 may extend from the cap or seal 517 to facilitate handling of the cover. The cap or seal 517 may be formed from any of the polymeric materials described herein, e.g., silicone.

Figure 26:
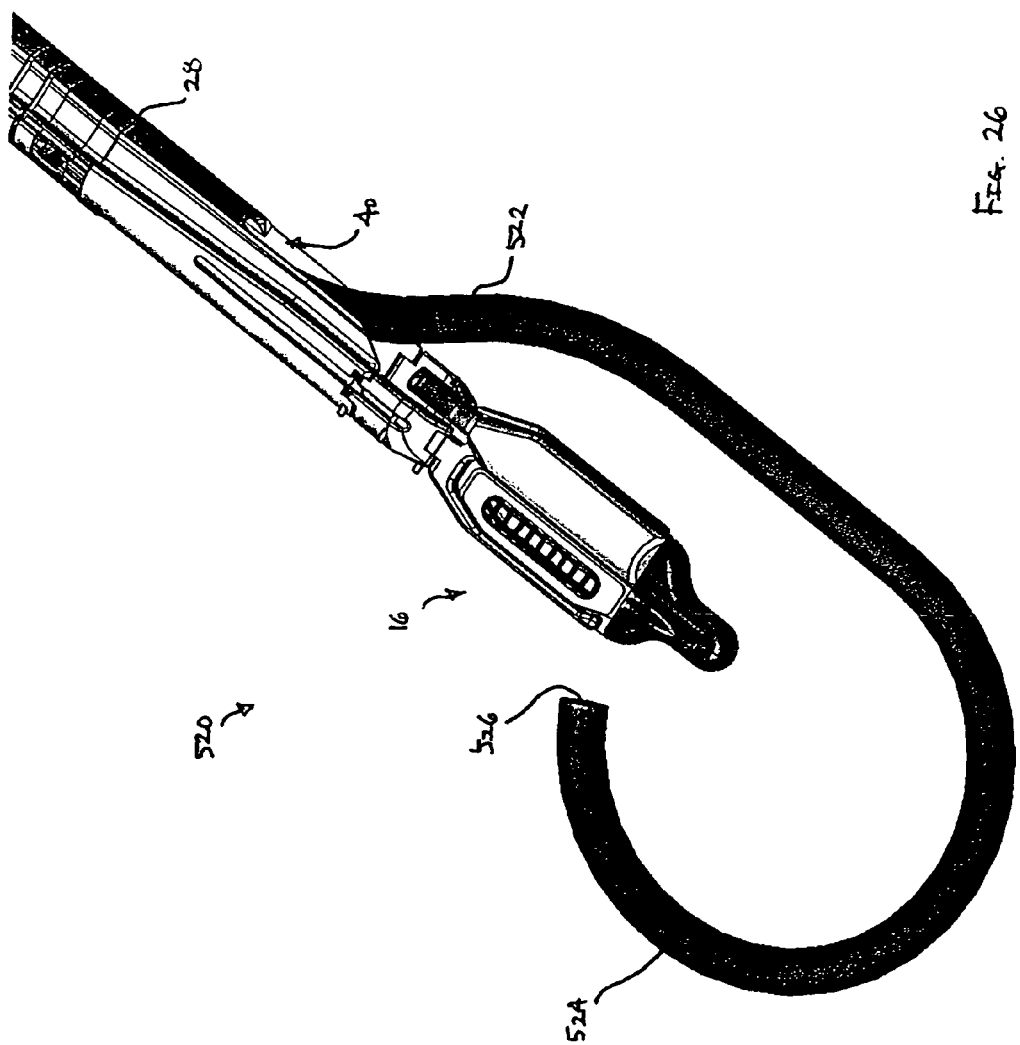
FIG. 26 shows a perspective view of one variation in which an endoscope can be retroflexed to view the results or progress of the tissue approximation and/or fixation.

FIG. 26 shows a variation 520 of how the tissue approximation assembly may be utilized with other devices such as an endoscope 522. In this example, clearance slots (open region 240) may function to provide clearance for an endoscope 522, or other tool, that can be inserted into and advanced through the main lumen 40 of working body 28. During tissue approximation, endoscope 522 may be advanced distally out of main lumen 40 and advanced past pod assembly 16. A bending region 524 of endoscope 522 may then be retroflexed to view the results or progress of the tissue approximation and/or fixation using an imaging system 526, e.g., optical fibers, CCD or CMOS imaging system, etc., positioned within a distal end of the endoscope 522.

Figure 27:
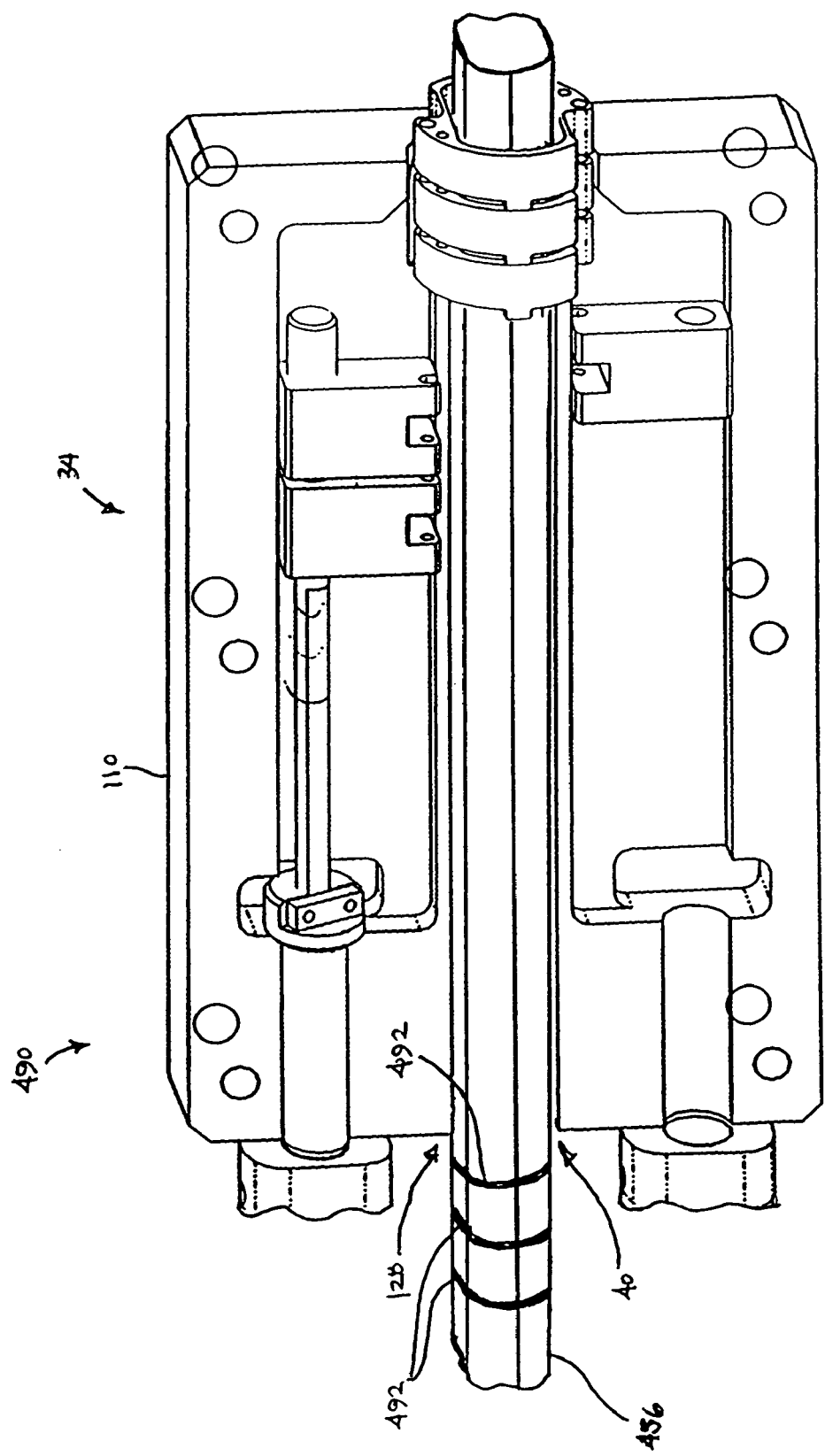
FIG. 27 shows a portion of a flexible shaft of a stapler assembly with several insertion indicators positioned through the main lumen of the handle of the folder assembly.

FIG. 27 shows a portion of flexible shaft 456 of the fixation assembly inserted through main lumen 40 of handle 110 in assembly 490. Handle 110 is partially shown for clarity. As mentioned above, one or several insertion indicators 492 may be defined along a portion of flexible shaft 456 at predetermined positions. These indicators are preferably located near a proximal end of shaft 456 to indicate information to the user. For instance, when shaft 456 is aligned against handle 110 at one particular indicator, this may notify the user when it is safe for stapler assembly 410 to be opened in a patient body, e.g., when cartridge housing 412 is positioned proximally of the tissue between the yoke members. A second indicator defined along shaft 456 may indicate to the user when the second indicator is aligned against handle 110 that it is safe to clamp stapler assembly 410 over the tissue, e.g., when stapler assembly 410 is positioned fully over the approximated and folded tissue thereby indicating that the cartridge housing 412 may be clamped against anvil 422 and the tissue for staple deployment. Additional indicators may be defined along shaft 456 to indicate various other information, e.g., positional information such as how deep stapler assembly has been inserted relative to the folder assembly. These examples are merely intended to be illustrative and are not limiting in how indicators defined along the shaft 456 may be utilized.

Once the tissue has been affixed, stapler assembly 410 may be removed from the main lumen of the folder assembly and an endoscopic device may be optionally inserted within the main lumen. The endoscopic device may be outfitted with a visual imaging system, e.g., fiberoptic, CCD, CMOS, etc., to view the tissue region. If necessary, stapler assembly 410, or some other tool, may be subsequently inserted through the main lumen to perform additional aspects of the procedure, or to complete the procedure with the placement of additional fixation elements.

In describing the system and its components, certain terms have been used for understanding, brevity, and clarity. They are primarily used for descriptive purposes and are intended to be used broadly and construed in the same manner. Having now described the invention and its method of use, it should be appreciated that reasonable mechanical and operational equivalents would be apparent to those skilled in this art. Those variations are considered to be within the equivalence of the claims appended to the specification.

What is claimed is:

1. A tissue acquisition and fixation system, comprising:
 a tissue acquisition device having a flexible, elongate main body comprising a plurality of links, each link having a central aperture defining a main lumen therethrough the flexible, elongate body, each link further defining a passage cooperating with adjacent passages in adjoining links to define a routing channel, wherein a distal end of the acquisition device includes a first pod member including a vacuum source adapted to acquire tissue from within a hollow body organ, and a second pod member including a vacuum source adapted to acquire tissue from within the hollow body organ, the first and second pod members adapted to separate apart and separate in an offset condition such that the acquired tissue is adjacent and forms and at least one overlap region such that four layers of tissue are positioned in an adjacent configuration; and
 a tissue fixation device having an articulatable cartridge assembly adapted to be advanced through the main lumen while maintaining a fixed orientation relative to the main lumen and adapted to staple the four layers of tissue positioned by the first and second pod members together while the pod members are in the apart and offset condition.

2. The system of claim 1, wherein the tissue acquisition device further comprises at least two opposing members longitudinally positioned relative to one another at a distal end of the main lumen such that the cartridge assembly is stabilized from lateral movement between the at least two opposing members.

3. The system of claim 1, wherein the tissue acquisition device further comprises an atraumatic distal tip.

4. The system of claim 3, wherein the distal tip is tapered.

5. The system of claim 1, wherein the elongate main body of the tissue acquisition device is configured to be curved.

6. The system of claim 1, further comprising a handle connected to a proximal end of the main body.

7. The system of claim 6, wherein the handle further comprises at least one actuation mechanism adapted to articulate the distal end of the acquisition device.

* * * * *